(12) United States Patent
Austad et al.

(10) Patent No.: US 8,703,448 B2
(45) Date of Patent: Apr. 22, 2014

(54) ENZYMATIC TRANSAMINATION OF CYCLOPAMINE ANALOGS

(75) Inventors: Brian C. Austad, Tewksbury, MA (US); Adilah Bahadoor, Stittsville (CA); Jitendra D. Belani, Newtonville, MA (US); Somarajannair Janardanannair, Woburn, MA (US); Charles W. Johannes, Singapore (SG); Gregg F. Keaney, Lexington, MA (US); Priscilla L. White, Malden, MA (US); Sheldon L. Wallerstein, Chesterfield, MO (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 135 days.

(21) Appl. No.: 13/175,053

(22) Filed: Jul. 1, 2011

(65) Prior Publication Data

US 2012/0083607 A1 Apr. 5, 2012

Related U.S. Application Data

(63) Continuation of application No. PCT/US2010/044597, filed on Aug. 5, 2010.

(60) Provisional application No. 61/231,439, filed on Aug. 5, 2009.

(51) Int. Cl.
*C12P 17/18* (2006.01)

(52) U.S. Cl.
USPC .............................. 435/119; 435/193; 546/15

(58) Field of Classification Search
USPC .................................... 435/119, 193; 546/15
See application file for complete search history.

(56) References Cited

U.S. PATENT DOCUMENTS

| | | | |
|---|---|---|---|
| 5,169,780 A * | 12/1992 | Stirling et al. | ................ 435/280 |
| 7,230,004 B2 | 6/2007 | Adams et al. | |
| 7,407,967 B2 | 8/2008 | Adams et al. | |
| 7,648,994 B2 | 1/2010 | Castro et al. | |
| 7,812,164 B2 | 10/2010 | Austad et al. | |
| 7,875,628 B2 | 1/2011 | Adams et al. | |
| 7,964,590 B2 | 6/2011 | Castro et al. | |
| 7,994,191 B2 | 8/2011 | Castro et al. | |
| 8,017,648 B2 | 9/2011 | Castro et al. | |
| 2008/0293754 A1 | 11/2008 | Austad et al. | |
| 2009/0012109 A1 | 1/2009 | Austad et al. | |
| 2009/0216022 A1 | 8/2009 | Austad et al. | |
| 2011/0166353 A1 | 7/2011 | Adams et al. | |
| 2011/0230509 A1 | 9/2011 | Castro et al. | |

OTHER PUBLICATIONS

Koszelewski, D. et al., "Trends in Biotechnology", vol. 28, (2010), pp. 324-332.
Tremblay, M. R. et al., Discovery of a Potent and Orally Active Hedgehog Pathway Antagonist (IPI-926), Journal of Medicinal Chemistry, (2009), pp. 4400-4418.
Yun, H. et al., "ω-Amino Acid: Pyruvate Transaminase from Alcaligenes denitrificans Y2k-2: a New Catalyst for Kinetic Resolution of β-Amino Acids and Amines", Applied and Environmental Microbiology, vol. 70, No. 4, (2004), pp. 2529-2534.
Yun, H. et al., "Simultaneous synthesis of enantiomerically pure (R)-1-phenylethanol and (R)-α-methylbenzylamine from racemic α-methylbenzylamine using co-transaminase/alcohol dehydrogenase/glucose dehydrogenase coupling reaction", Biotechnology Letters, vol. 25, (2003), pp. 809-814.
International Search Report and Written Opinion of the International Searching Authority in corresponding PCT/US2010/44597, mailed Oct. 1, 2010, 11 pages.

* cited by examiner

*Primary Examiner* — Susan Hanley
(74) *Attorney, Agent, or Firm* — Fish & Richardson P.C.

(57) ABSTRACT

The invention relates to the preparation of amino-cyclopamines by the enzymatic transamination of a corresponding keto-cyclopamines in the presence of a cofactor and an amino donor.

37 Claims, 2 Drawing Sheets

ENZYMATIC TRANSAMINATION OF CYCLOPAMINE ANALOGS

This application is a continuation of International Application No. PCT/US2010/044597, filed Aug. 5, 2010, which claims the benefit of U.S. Provisional Application No. 61/231,439, filed on Aug. 5, 2009, each of these prior applications is incorporated herein by reference in its entirety.

BACKGROUND

Cyclopamine, a natural product isolated from *Veratrum californicum*, has emerged as a significant pharmacological tool to validate the Hedgehog (Hh) pathway in cancer. Cyclopamine directly acts on SMO and inhibits tumor growth in several murine models of pancreatic, medulloblastoma, prostate, small cell lung, and digestive tract cancer's. However, the clinical development of cyclopamine as a therapeutic in cancer is hampered by its poor solubility, acid sensitivity, and weak potency relative to other reported small-molecule Hh antagonists.

There has been considerable focus on the development of novel cyclopamine analogues with improved potency, and improved pharmacokinetic and pharmaceutical properties relative to cyclopamine (see, for example, U.S. Pat. Nos. 7,230,004 and 7,407,967, incorporated herein by reference). From that effort, a seven-membered D-ring sulfonamide analogue of cyclopamine, IPI-926, emerged as a clinical development candidate (see Tremblay et al., "Discovery of a Potent and Orally Active Hedgehog Pathway Antagonist (IPI-926)" *J. Med. Chem.* (2009) 52:4400-4418, incorporated herein by reference). Large quantities of IPI-926 are required for clinical development. Moreover, other promising amino analogues can be synthesized following routes similar to that used to generate IPI-926.

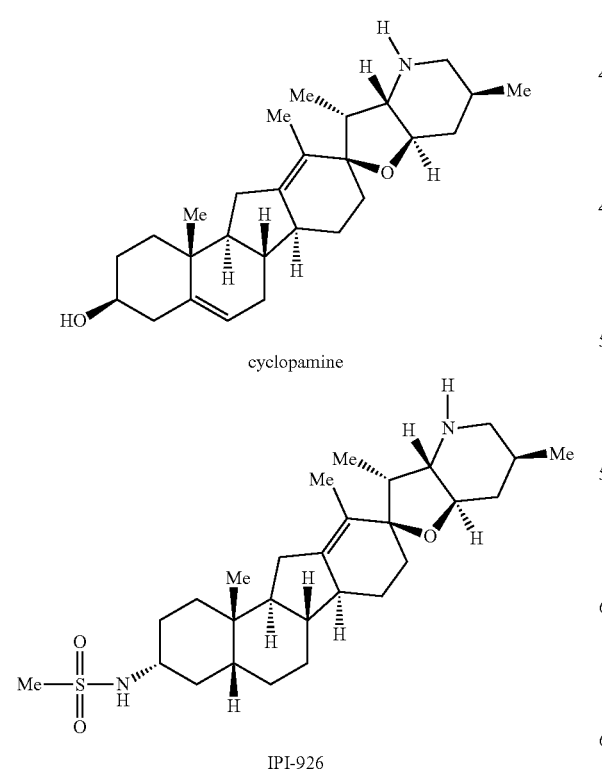

cyclopamine

IPI-926

SUMMARY

Provided are novel processes for the synthesis of amino analogues, such as IPI-926, from ketone starting materials.

For example, in one aspect, provided is a process for preparing a compound of formula (II):

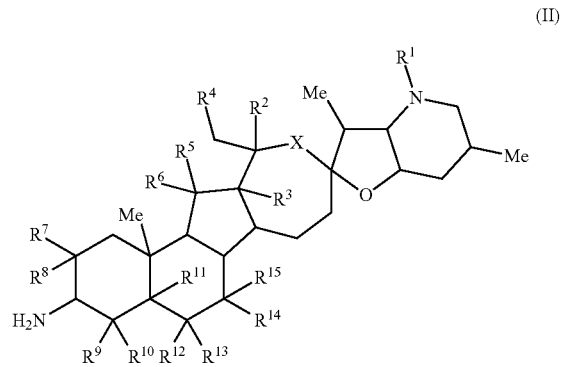

or a salt thereof;
from a compound of formula (I):

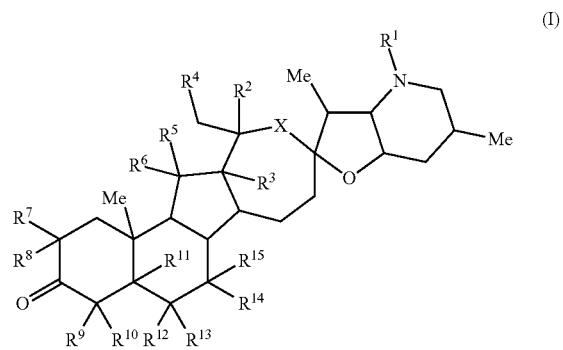

or a salt thereof;
wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and X are as defined herein, the process comprising contacting a compound of formula (I) or a salt thereof, an amino donor molecule, and an amine transaminase enzyme in a solution to provide a compound of formula (II) or a salt thereof.

In certain embodiments, the process further comprises adding a co-factor to the solution.

In certain embodiments, the co-factor is pyridoxal phosphate (PLP).

In certain embodiments, the co-factor is a co-enzyme. In certain embodiments, the co-enzyme is selected from L-alanine dehydrogenase (LADH), lactate dehydrogenase (LDH), nicotinamide adenine dinucleotide phosphate (NADPH), nicotinamide adenine dinucleotide (NAD), formate dehydrogenase (FDH), and glucose dehydrogenase (GDH).

In certain embodiments, process further comprises adding a pyruvate reductase mix to the solution. As used herein, the term "pyruvate reductase mix" refers to a combination that includes an enzyme that is capable of mediating the reduction of pyruvate and one or more (e.g., 1, 2, 3, 4, 5, or 6, e.g., 2, 3 or 4, e.g., 2 or 3) additional agents (e.g., an enzyme, a co-enzyme or co-factor, a reducing agent as well as combinations thereof).

In embodiments, the enzyme that is capable of mediating the reduction of pyruvate is LDH.

In embodiments, the combination includes an agent (e.g., an enzyme) that is capable of regenerating a co-enzyme or co-factor that mediates pyruvate reduction. In certain embodiments, the combination can include an enzyme that is capable of regenerating NADPH. Such enzymes can include, without limitation, GDH and FDH.

In embodiments, the combination includes a reducing agent. Reducing agents can include, without limitation, glucose or formate.

In embodiments, the combination includes a co-enzyme or co-factor. Co-enzymes or co-factors can include, without limitation, NAD.

In embodiments, the combination includes an agent (e.g., an enzyme) that is capable of regenerating a co-enzyme or co-factor that mediates pyruvate reduction as defined anywhere herein; and one or more additional agents (e.g., 2 or 3 additional agents). For example, the combination can include an agent (e.g., an enzyme) that is capable of regenerating a co-enzyme or co-factor that mediates pyruvate reduction as defined anywhere herein; and one or both of the following: a reducing agent and a co-enzyme or co-factor.

In embodiments, a pyruvate reductase mix includes LDH, an agent (e.g., an enzyme) that is capable of regenerating a co-enzyme or co-factor that mediates pyruvate reduction as defined anywhere herein; and one or more additional agents (e.g., 2 or 3 additional agents); e.g., one or both of the following; a reducing agent and a co-enzyme or co-factor. For example, a pyruvate reductase mix can include LDH, GDH, and glucose and can further include NAD, e.g., PRM-102 (Codexis), which includes LDH, GDH, glucose, and NAD$^+$. As another example, a pyruvate reductase mix can include LDH, FDH, and formate and can further include NAD.

In certain embodiments, when pyruvate is generated during the course of the processes described herein, the pyruvate can be removed, chemically converted to another product and optionally further removed; or recycled (or combinations thereof). Methods describing such operations are described in, e.g., Koszelewski, D., et al., *Trends in Biotechnology* 2010, 28, 324-332, which is incorporated herein by reference in its entirety.

In certain embodiments, the enzyme preferentially generates a compound of formula (II), or a salt thereof, wherein the newly-formed amino group has (R) or (S) stereochemistry.

In certain embodiments, the enzyme is an omega amine transaminase, a broad-range transaminase, a glutamate-pyruvate transaminase or a glutamate-oxaloacetic transaminase.

In certain embodiments, the enzyme is an omega amine transaminase.

In certain embodiments, the omega amine transaminase is selected from the group consisting of ATA-101, ATA-102, ATA-103, ATA-104, ATA-105, ATA-106, ATA-107, ATA-108, ATA-109, ATA-110, ATA-113, ATA-114, ATA-115, ATA-116, ATA-117, ATA-124, an omega amine transaminase from *Chromobacterium violaceum*, an omega amine transaminase from *Alcaligenes denitrificans*, an omega amine transaminase from *Arthrobactercitreus*, an omega amine transaminase from *Klebsiella pneumoniae*, an omega amine transaminase from *Bacillus thuringiensis*, an omega amine transaminase from *Bacillus cereus*, and an omega amine transaminase from *Vibrio fluvialis*.

In certain embodiments, the amino donor molecule is an amine or a salt thereof. In embodiments, the amine is selected from pyridoxamine, methylbenzylamine, 2-aminobutane, propyl amine, isopropyl amine, 1,1,1-trifluoropropan-2-amine, 1,1,1,3,3,3-hexafluoropropan-2-amine, benzyl amine, 2-amino-1-butanol, 1-amino-1-phenylethane, 1-amino-1-(2-methoxy-5-fluorophenyl)ethane, 1-amino-1-phenylpropane, 1-amino-1-(4-hydroxyphenyl)propane, 1-amino-1-(4-bromophenyl)propane, nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, dimethoxy-4-methylphenyl)-2-aminobutane, 1-phenyl-3-aminobutane, 1-(4-hydroxyphenyl)-3-aminobutane, 1-amino-1-(2-naphthyl)ethane, cis-2-methylcyclopentanamine, trans-2-methylcyclopentanamine, cis-3-methylcyclopentanamine, trans-3-methylcyclopentanamine, cis-2-ethylcyclopentanamine, trans-2-ethylcyclopentanamine, cis-3-ethylcyclopentanamine, trans-3-ethylcyclopentanamine, cis-2-methylcyclohexanamine, trans-2-methylcyclohexanamine, cis-3-methylcyclohexanamine, trans-3-methylcyclohexanamine, cis-2-ethylcyclohexanamine, trans-2-ethylcyclohexanamine, cis-3-ethylcyclohexanamine, trans-3-ethylcyclohexanamine, 1-aminotetralin, 2-aminotetralin, 2-amino-5-methoxytetralin, 1-aminoindane, 2-aminoindane, 2-amino-1-propanol, cis-1-amino-2-indanol, trans-1-amino-2-indanol, 1-amino-6-hydroxyindanamine, taurine, or a salt thereof.

In certain embodiments, the amino donor molecule is a chiral amino donor molecule. In certain embodiments, the chiral amino donor molecule is a chiral amine or salt thereof, e.g., an amine containing at least one asymmetric center. Exemplary chiral amines include, but are not limited to, (R)-methylbenzylamine, (S)-methylbenzylamine, (S)-2-aminobutane, (R)-2-aminobutane, (S)-1-aminoindane, (R)-1-aminoindane, (R)-1,1,1-trifluoropropan-2-amine, (S)-1,1,1-trifluoropropan-2-amine, (R)-2-amino-1-propanol, (S)-2-amino-1-propanol, (1R,2S)-cis-1-amino-2-indanol, (1R,2R)-trans-1-amino-2-indanol, 1-(R)-amino-6-hydroxyindanamine, 1-(S)-amino-6-hydroxyindanamine, (R)-2-amino-1-butanol, (S)-2-amino-1-butanol, (R)-1-amino-1-phenylethane, (S)-1-amino-1-phenylethane, (R)-1-amino-1-(2-methoxy-5-fluorophenyl)ethane, (S)-1-amino-1-(2-methoxy-5-fluorophenyl)ethane, (R)-1-amino-1-phenylpropane, (S)-1-amino-1-phenylpropane, (R)-1-amino-1-(4-hydroxyphenyl)-propane, (S)-1-amino-1-(4-hydroxyphenyl)-propane, (R)-1-amino-1-(4-bromophenyl)propane, (S)-1-amino-1-(4-bromophenyl)propane, (R)-1-amino-1-(4-nitrophenyl)propane, (S)-1-amino-1-(4-nitrophenyl)propane, (R)-1-phenyl-2-aminopropane, (S)-1-phenyl-2-aminopropane, (R)-1-(3-trifluoromethylphenyl)-2-aminopropane, (S)-1-(3-trifluoromethylphenyl)-2-aminopropane (R)-1-amino-1-phenylbutane, (S)-1-amino-1-phenylbutane, (R)-1-phenyl-2-aminobutane, (S)-1-phenyl-2-aminobutane, (R)-1-(2,5-di-methoxy-4-methylphenyl)-2-aminobutane, (S)-1-(2,5-di-methoxy-4-methylphenyl)-2-aminobutane, (R)-1-phenyl-3-aminobutane, (S)-1-phenyl-3-aminobutane, (R)-1-(4-hydroxyphenyl)-3-aminobutane, (S)-1-(4-hydroxyphenyl)-3-aminobutane, (R)-1-amino-1-(2-naphthyl)ethane, (S)-1-amino-1-(2-naphthyl)ethane (R)-1-aminotetralin, (S)-1-aminotetralin, (R)-2-aminotetralin, (S)-2-aminotetralin, (R)-2-amino-5-methoxytetralin, (S)-2-amino-5-methoxytetralin, (1R,2S)-cis-2-methylcyclopentanamine, (1S,2R)-cis-2-methylcyclopentanamine, (1R,2R)-trans-2-methylcyclopentanamine, (1S,2S)-trans-2-methylcyclopentanamine, (1R,3S)-cis-3-methylcyclopentanamine, (1S,3R)-cis-3-methylcyclopentanamine, (1R,3R)-trans-3-methylcyclopentanamine, (1S,3S)-trans-3-methylcyclopentanamine, (1R,2S)-cis-2-ethylcyclopentanamine, (1S,2R)-cis-2-ethylcyclopentanamine, (1R,2R)-trans-2- ethylcyclopentanamine, (1S,2S)-trans-2-ethylcyclopentanamine, (1R,3S)-cis-3-ethylcyclopentanamine, (1S,3R)-cis-3-ethylcyclopentanamine, (1R,3R)-trans-3-ethylcyclopentanamine, (1S,3S)-trans-3-ethylcyclopentanamine, (1R,2S)-cis-2-methylcyclohexanamine, (1S,2R)-cis-2-methylcyclohexanamine, (1R,2R)-trans-2-methylcyclohexanamine, (1S,2S)-trans-2-methylcyclohexanamine, (1R,3S)-cis-3-methylcyclohexanamine, (1S,3R)-cis-3-methylcyclohexanamine, (1R,3R)-trans-3-methylcyclohexanamine, (1S,3S)-trans-3-methylcyclohexanamine, (1R,2S)-cis-2-ethylcyclohexanamine, (1S,2R)-cis-2-ethylcyclohexanamine, (1R,2R)-trans-2-ethylcyclohexanamine, (1S,2S)-trans-2-ethylcyclohexanamine, (1R,3S)-cis-3-ethylcyclohexanamine, (1S,3R)-cis-3-ethylcyclohexanamine, (1R,3R)-trans-3-ethylcyclohexanamine, (1S,3S)-trans-3-ethylcyclohexanamine, or a salt thereof.

In certain embodiments, the amino donor molecule is an amino acid or a polypeptide thereof and/or salt thereof. In certain embodiments, the amino acid is selected from glycine, alanine, aspartic acid, phenylalanine, 2-aminopentanedioic acid, 3-aminobutyrate, γ-aminobutyrate, β-alanine, asparagine, cysteine, glutamic acid, glutamine, proline, selenocysteine, serine, tyrosine, arginine, histidine, ornithine, isoleucine, leucine, lysine, methionine, threonine, tryptophan, valine, and polypeptides thereof and/or salts thereof.

In certain embodiments, the chiral amino donor molecule is a chiral amino acid or a polypeptide thereof and/or a salt thereof, e.g., containing at least one asymmetric center. Exemplary chiral amino acids include, but are not limited to, (L)-alanine, (D)-alanine, (L)-aspartic acid, (D)-aspartic acid, (L) phenylalanine, (D)-phenylalanine, (2S)-2-aminopentanedioic acid, (L)-asparagine, (D)-asparagine, (L)-cysteine, (D)-cysteine, (L)-glutamine, (D)-glutamine, (L)-glutamic acid, (D)-glutamic acid, (L)-proline, (D)-proline, (L)-selenocysteine, (D)-selenocysteine, (L)-serine, (D)-serine, (L)-tyrosine, (D)-tyrosine, (L)-arginine, (D)-arginine, (L)-histidine, (D)-histidine, (L)-isoleucine, (D)-isoleucine, (L)-leucine, (D)-leucine, (L)-lysine, (D)-lysine, (L)-methionine, (D)-methionine, (L)-threonine, (D)-threonine, (L)-tryptophan, (D)-tryptophan, (L)-valine, (D)-valine, (L)-ornithine, (D)-ornithine, (3R)-aminobutyrate, (3S)-aminobutyrate and polypeptides thereof and/or salts thereof.

In certain embodiments, the solution is a buffered solution. In certain embodiments, the buffered solution is a sodium phosphate buffered solution.

In certain embodiments, the pH of the solution is between about 5 and about 9, between about 5 and about 8, between about 6 and about 8, between about 7 and about, 8, between about 7 and about 7.5, or between about 7.5 and about 8.

In certain embodiments, the pH is of the solution is less than about 9, less than about 8.5, or less than about 8. In certain embodiments, the pH of the solution is about 7. In certain embodiments, the pH of the solution is about 7.5. In certain embodiments, the pH of the solution is about 8.

In certain embodiments, the compound of formula (I) or a salt thereof and a compound of formula (II) or a salt thereof are selected from any set of compounds provided in Tables 1, 2, 3, 4 or 5.

In certain embodiments, the process further comprises contacting a compound of formula (II) or a salt thereof with a sulfonylating agent to provide a compound of formula (III):

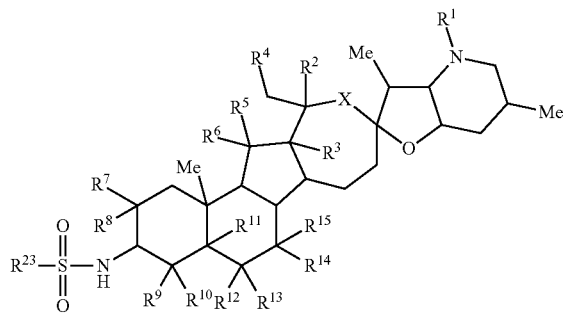

(III)

or a salt thereof,
wherein $R^{23}$ is alkyl or aryl.

In certain embodiments, the sulfonylating agent is selected from benzenesulfonyl chloride, benzenesulfonyl anhydride, p-toluenesulfonyl chloride, p-toluenesulfonyl anhydride, methanesulfonyl chloride, and methanesulfonyl anhydride. In certain embodiments, the sulfonylating agent is methanesulfonyl chloride or methanesulfonyl anhydride, and $R^{23}$ is —$CH_3$.

The details of additional or alternative embodiments are set forth in the accompanying Detailed Description and Examples as described below. Other features, objects, and advantages of the invention will be apparent from this description and from the claims.

DEFINITIONS

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987, each of which is incorporated herein by reference.

Certain compounds of the present invention comprise one or more asymmetric centers, and thus can exist in various isomeric forms, e.g., enantiomers and/or diastereomers. The compounds provided herein can be in the form of an individual enantiomer, diastereomer or geometric isomer, or can be in the form of a mixture of stereoisomers, including racemic mixtures and mixtures enriched in one or more stereoisomer. In certain embodiments, the compounds of the invention are enantiopure compounds. In certain other embodiments, mixtures of stereoisomers are provided.

Furthermore, certain compounds, as described herein may have one or more double bonds that can exist as either the cis or trans, or the E or Z isomer, unless otherwise indicated. The invention additionally encompasses the compounds as individual isomers substantially free of other isomers, and alternatively, as mixtures of various isomers, e.g., racemic mixtures of E/Z isomers or mixtures enriched in one E/Z isomer.

The terms "enantiomerically enriched," "enantiomerically pure" and "non-racemic," as used interchangeably herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, more preferably at least 75% by weight, and even more preferably at least 80% by weight. In some embodiments, the enrichment can be much greater than 80% by weight, providing a "substantially enantiomerically enriched," "substantially enantiomerically pure" or a "substantially non-racemic" preparation, which refers to preparations of compositions which have at least 85% by weight of one enantiomer relative to other enantiomer, more preferably at least 90% by weight, and even more preferably at least 95% by weight. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972), each of which is incorporated herein by reference.

Carbon atoms, unless otherwise specified, may optionally be substituted with one or more substituents. The number of substituents is typically limited by the number of available valences on the carbon atom, and may be substituted by replacement of one or more of the hydrogen atoms that would be available on the unsubstituted group. Suitable substituents are known in the art and include, but are not limited to, alkyl, alkenyl, alkynyl, alkoxy, alkoxy, alkylthio, aryl, aryloxy, arylthio, aralkyl, heteroaryl, heteroaralkyl, cycloalkyl, heterocyclyl, halo, azido, hydroxyl, thio, amino, nitro, nitrile, imido, amido, carboxylic acid, aldehyde, carbonyl, ester, silyl, haloalkyl, haloalkoxy (e.g., perfluoroalkoxy such as —$OCF_3$), =O, =S, and the like.

When a range of values is listed, it is intended to encompass each value and sub-range within the range. For example, an alkyl group containing 1-6 carbon atoms ($C_{1-6}$ alkyl) is intended to encompass, $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1\ 4}$, $C_{2\ 4}$, $C_{3\ 4}$, $C_{1\ 3}$, $C_{2\ 3}$, and $C_{1\ 2}$ alkyl.

The term "alkyl," as used herein, refers to saturated, straight- or branched-chain hydrocarbon radical containing between one and thirty carbon atoms. In certain embodiments, the alkyl group contains 1-20 carbon atoms. Alkyl groups, unless otherwise specified, may optionally be substituted with one or more substituents. In certain embodiments, the alkyl group contains 1-10 carbon atoms. In certain embodiments, the alkyl group contains 1-6 carbon atoms. In certain embodiments, the alkyl group contains 1-5 carbon atoms. In certain embodiments, the alkyl group contains 1-4 carbon atoms. In certain embodiments, the alkyl group contains 1-3 carbon atoms. In certain embodiments, the alkyl group contains 1-2 carbon atoms. In certain embodiments, the alkyl group contains 1 carbon atom. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a straight- or branched-chain hydrocarbon radical having at least one carbon-carbon double bond by the removal of a single hydrogen atom, and containing between two and thirty carbon atoms. Alkenyl groups, unless otherwise specified, may optionally be substituted with one or more substituents. In certain embodiments, the alkenyl group contains 2-20 carbon atoms. In certain embodiments, the alkenyl group contains 2-10 carbon atoms. In certain embodiments, the alkenyl group contains 2-6 carbon atoms. In certain embodiments, the alkenyl group contains 2-5 carbon atoms. In certain embodiments, the alkenyl group contains 2-4 carbon atoms. In certain embodiment, the alkenyl group contains 2-3 carbon atoms. In certain embodiments, the alkenyl group contains 2 carbon atoms. Alkenyl groups include, for example, ethenyl, propenyl, butenyl, 1-methyl-2-buten-1-yl, and the like.

The term "alkynyl," as used herein, denotes a straight- or branched-chain hydrocarbon radical having at least one carbon-carbon triple bond by the removal of a single hydrogen atom, and containing between two and thirty carbon atoms. Alkynyl groups, unless otherwise specified, may optionally be substituted with one or more substituents. In certain embodiments, the alkynyl group contains 2-20 carbon atoms. In certain embodiments, the alkynyl group contains 2-10 carbon atoms. In certain embodiments, the alkynyl group contains 2-6 carbon atoms. In certain embodiments, the alkynyl group contains 2-5 carbon atoms. In certain embodiments, the alkynyl group contains 2-4 carbon atoms. In certain embodiments, the alkynyl group contains 2-3 carbon atoms. In certain embodiments, the alkynyl group contains 2 carbon atoms. Representative alkynyl groups include, but are not limited to, ethynyl, 2-propynyl (propargyl), 1-propynyl, and the like.

The terms "cycloalkyl", used alone or as part of a larger moiety, refer to a saturated monocyclic or bicyclic hydrocarbon ring system having from 3-15 carbon ring members. Cycloalkyl groups, unless otherwise specified, may optionally be substituted with one or more substituents. In certain embodiments, cycloalkyl groups contain 3-10 carbon ring members. In certain embodiments, cycloalkyl groups contain 3-9 carbon ring members. In certain embodiments, cycloalkyl groups contain 3-8 carbon ring members. In certain embodiments, cycloalkyl groups contain 3-7 carbon ring members. In certain embodiments, cycloalkyl groups contain 3-6 carbon ring members. In certain embodiments, cycloalkyl groups contain 3-5 carbon ring members. Cycloalkyl groups include, without limitation, cyclopropyl, cyclobutyl, cyclopentyl, cyclohexyl, cycloheptyl, and cyclooctyl. The term "cycloalkyl" also includes saturated hydrocarbon ring systems that are fused to one or more aryl or heteroaryl rings, such as decahydronaphthyl or tetrahydronaphthyl, where the point of attachment is on the saturated hydrocarbon ring.

The term "aryl" used alone or as part of a larger moiety (as in "aralkyl"), refers to an aromatic monocyclic and bicyclic hydrocarbon ring system having a total of 6-10 carbon ring members. Aryl groups, unless otherwise specified, may optionally be substituted with one or more substituents. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aryl ring is fused to one or more non-aromatic rings, such as indanyl, phthalimidyl or tetrahydronaphthalyl, and the like, where the point of attachment is on the aryl ring.

The term "aralkyl" refers to an alkyl group, as defined herein, substituted by aryl group, as defined herein, wherein the point of attachment is on the alkyl group.

The term "heteroatom" refers to boron, phosphorus, selenium, nitrogen, oxygen, or sulfur, and includes any oxidized form of nitrogen or sulfur, and any quaternized form of abasic nitrogen.

The terms "heteroaryl" used alone or as part of a larger moiety, e.g., "heteroaralkyl", refer to an aromatic monocyclic or bicyclic hydrocarbon ring system having 5-10 ring atoms wherein the ring atoms comprise, in addition to carbon atoms, from one to five heteroatoms. Heteroaryl groups, unless otherwise specified, may optionally be substituted with one or more substituents. When used in reference to a ring atom of a heteroaryl group, the term "nitrogen" includes a substituted nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaryl ring is fused to one or more aryl, cycloalkyl or heterocycloalkyl rings, wherein the point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl.

The term "heteroaralkyl" refers to an alkyl group, as defined herein, substituted by a heteroaryl group, as defined herein, wherein the point of attachment is on the alkyl group.

As used herein, the terms "heterocycloalkyl" or "heterocyclyl" refer to a stable non-aromatic 5-7 membered monocyclic hydrocarbon or stable non-aromatic 7-10 membered bicyclic hydrocarbon that is either saturated or partially unsaturated, and having, in addition to carbon atoms, one or more heteroatoms. Heterocycloalkyl or heterocyclyl groups, unless otherwise specified, may optionally be substituted with one or more substituents. When used in reference to a ring atom of a heterocycloalkyl group, the term "nitrogen" includes a substituted nitrogen. The point of attachment of a heterocycloalkyl group may be at any of its heteroatom or carbon ring atoms that results in a stable structure. Examples of heterocycloalkyl groups include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. "Heterocycloalkyl" also include groups in which the heterocycloalkyl ring is fused to one or more aryl, heteroaryl or cycloalkyl rings, such as indolinyl, chromanyl, phenanthridinyl, or tetrahydroquinolinyl, where the radical or point of attachment is on the heterocycloalkyl ring.

The term "unsaturated", as used herein, means that a moiety has one or more double or triple bonds.

As used herein, the term "partially unsaturated" refers to a ring moiety that includes at least one double or triple bond. The term "partially unsaturated" is intended to encompass rings having multiple sites of unsaturation, but is not intended to include aromatic groups, such as aryl or heteroaryl moieties, as defined herein.

The term "diradical" as used herein refers to an alkyl, alkenyl, alkynyl, aryl, cycloalkyl, heterocycloalkyl, aralkyl, heteroaryl, and heteroaralkyl groups, as described herein, wherein 2 hydrogen atoms are removed to form a divalent moiety. Diradicals are typically end with a suffix of "-ene". For example, alkyl diradicals are referred to as alkylenes (for example:

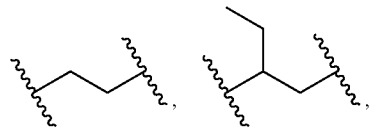

and —(CR'$_2$)$_x$— wherein R' is hydrogen or other substituent and x is 1, 2, 3, 4, 5 or 6); alkenyl diradicals are referred to as "alkenylenes"; alkynyl diradicals are referred to as "alkynylenes"; aryl and aralkyl diradicals are referred to as "arylenes" and "aralkylenes", respectively (for example:

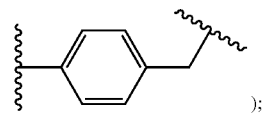

heteroaryl and heteroaralkyl diradicals are referred to as "heteroarylenes" and "heteroaralkylenes", respectively (for example:

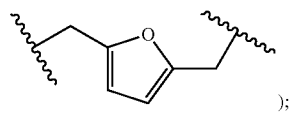 [SMILES: *Cc1ccc(C*)o1]

cycloalkyl diradicals are referred to as "cycloalkylenes"; heterocycloalkyl diradicals are referred to as "heterocycloalkylenes"; and the like.

The terms "halo" and "halogen" as used herein refer to an atom selected from fluorine (fluoro, —F), chlorine (chloro, —Cl), bromine (bromo, —Br), and iodine (iodo, —I).

As used herein, the term "haloalkyl" refers to an alkyl group, as described herein, wherein one or more of the hydrogen atoms of the alkyl group is replaced with one or more halogen atoms. In certain embodiments, the haloalkyl group is a perhaloalkyl group, that is, having all of the hydrogen atoms of the alkyl group replaced with halogens (e.g., such as the perfluoroalkyl group —CF$_3$).

As used herein, the term "azido" refers to the group —N$_3$.

As used herein, the term "nitrile" refers to the group —CN.

As used herein, the term "nitro" refers to the group —NO$_2$.

As used herein, the term "hydroxyl" or "hydroxy" refers to the group —OH.

As used herein, the term "thiol" or "thio" refers to the group —SH.

As used herein, the term "carboxylic acid" refers to the group —CO$_2$H.

As used herein, the term "aldehyde" refers to the group —CHO.

As used herein, the term "alkoxy" refers to the group —OR', wherein R' is an alkyl, alkenyl or alkynyl group, as defined herein.

As used herein, the term "aryloxy" refers to the group —OR', wherein each R' is an aryl or heteroaryl group, as defined herein.

As used herein, the term "alkylthio" or "alkylthiooxy" refers to the group —SR', wherein each R' is, independently, a carbon moiety, such as, for example, an alkyl, alkenyl, or alkynyl group, as defined herein.

As used herein, the term "arylthio" refers to the group —SR', wherein each R' is an aryl or heteroaryl group, as defined herein.

As used herein, the term "amino" refers to the group —NR'$_2$, wherein each R' is, independently, hydrogen, a carbon moiety, such as, for example, an alkyl, alkenyl, alkynyl, aryl or heteroaryl group, as defined herein, or two R' groups together with the nitrogen atom to which they are bound form a 5-8 membered ring.

As used herein, the term "carbonyl" refers to the group —C(=O)R', wherein R' is, independently, a carbon moiety, such as, for example, an alkyl, alkenyl, alkynyl, aryl or heteroaryl group, as defined herein.

As used herein, the term "ester" refers to the group —C(=O)OR' or —OC(=O)R' wherein each R' is, independently, a carbon moiety, such as, for example, an alkyl, alkenyl, alkynyl, aryl or heteroaryl group, as defined herein.

As used herein, the term "amide" or "amido" refers to the group —C(=O)N(R')$_2$ or —NR'C(=O)R' wherein each R' is, independently, hydrogen or a carbon moiety, such as, for example, an alkyl, alkenyl, alkynyl, aryl or heteroaryl group, as defined herein, or two R' groups together with the nitrogen atom to which they are bound form a 5-8 membered ring.

As used herein, the term "imide" or "imido" refers to the group —C(=NR')N(R')$_2$ or —NR'C(=NR')R' wherein each R' is, independently, hydrogen or a carbon moiety, such as, for example, an alkyl, alkenyl, alkynyl, aryl or heteroaryl group, as defined herein, or wherein two R' groups together with the nitrogen atom to which they are bound form a 5-8 membered ring.

As used herein "silyl" refers to the group —Si(R')$_3$ wherein R' is a carbon moiety, such as, for example, an alkyl, alkenyl, alkynyl, aryl or heteroaryl group.

The term "salt" refers to inorganic and organic acid addition salts of compounds of the present invention. Non-limiting examples of representative salts include salts derived from suitable inorganic and organic acids, e.g., hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other acid addition salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like (see, for example, Berge et al. (1977) "Pharmaceutical Salts", *J. Pharm. Sci.* 66:119, incorporated herein by reference).

BRIEF DESCRIPTION OF THE DRAWINGS

FIG. 2a depicts the L-alanine dehydrogenase (LADH)/formate dehydrogenase (FDH) promoted transamination. FIG. 2b depicts the lactate dehydrogenase (LDH)/Glucose dehydrogenase (GDH) promoted transamination.

DETAILED DESCRIPTION

Figure 1:
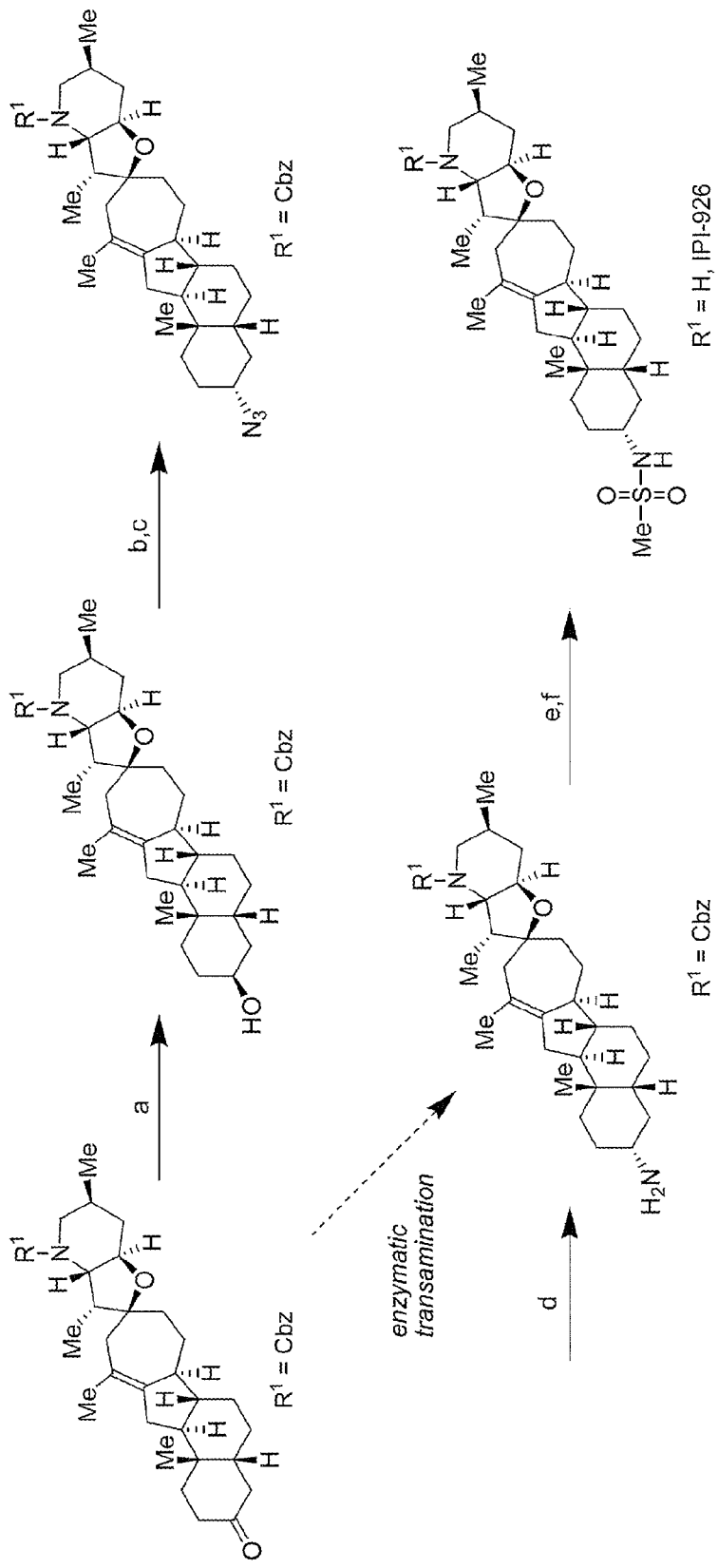
FIG. 1 depicts the chemical synthesis of IPI-926 in six steps from a ketone starting material as described in Tremblay et. al., "Discovery of a Potent and Orally Active Hedgehog Pathway Antagonist (IPI-926)" *J. Med. Chem.* (2009) 52:4400-4418. The inventive transamination method shortens this route by at least three steps.
Figure 2:
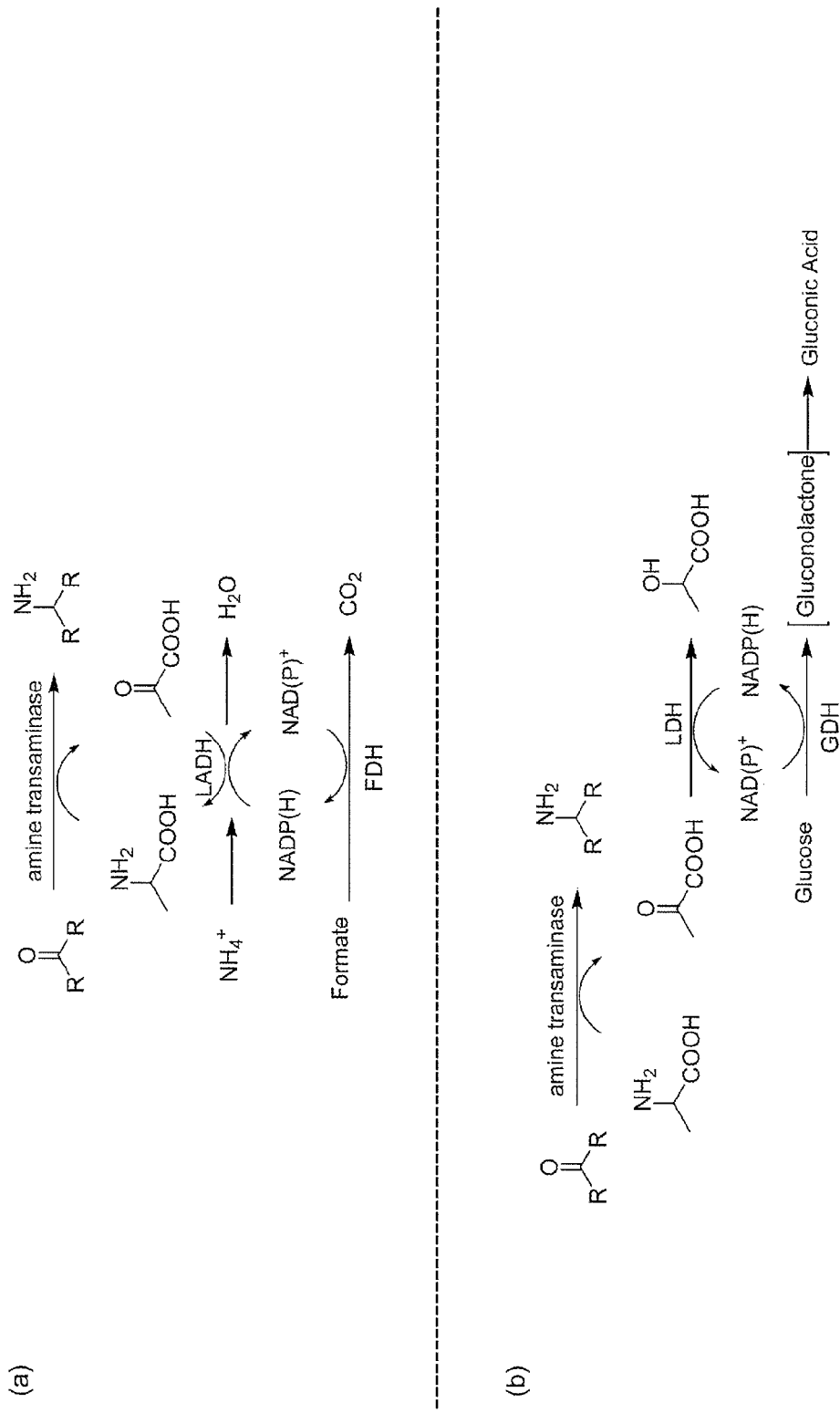
FIG. 2 depicts two types of enzymatic transaminations.

Provided is a process for preparing a compound of formula (II):

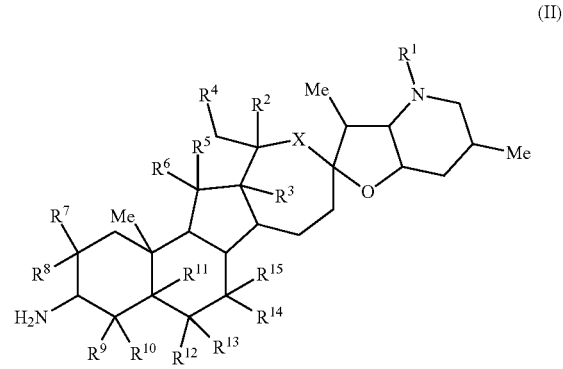

(II)

or a salt thereof;
from a compound of formula (I):

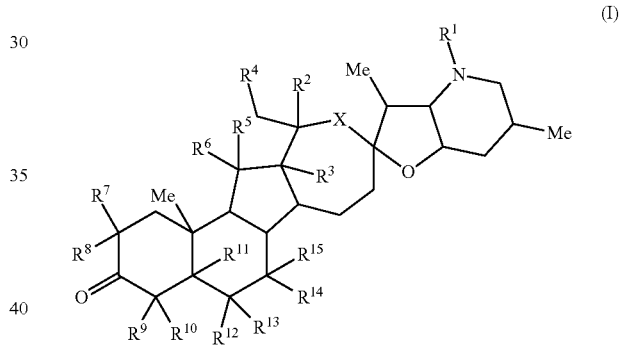

(I)

or a salt thereof;
wherein:
R$^1$ is H, alkyl, alkenyl, alkynyl, aryl, cycloalkyl, heterocycloalkyl, aralkyl, heteroaryl, heteroaralkyl, haloalkyl, —OR$^{16}$, —C(O)R$^{16}$, —CO$_2$R$^{16}$, —SO$_2$R$^{16}$, —C(O)N(R$^{17}$)(R$^{17}$), —[C(R$^{16}$)$_2$]$_q$—, R$^{16}$, —[(W)—N(R$^{17}$)C(O)]$_q$R$^{16}$, —[(W)—C(O)]$_q$R$^{16}$, —[(W)—C(O)]$_q$R$^{16}$, —[(W)—OC(O)]$_q$R$^{16}$, —[(W)—SO$_2$]$_q$R$^{16}$, —[(W)—N(R$^{17}$)SO$_2$]$_q$R$^{16}$, —[(W)—C(O)N(R$^{17}$)]$_q$R$^{17}$, —[(W)—O]$_q$R$^{16}$, —[(W)—N(R$^{17}$)]$_q$R$^{16}$, or —[(W)—S]$_q$R$^{16}$; wherein W is a diradical and q is 1, 2, 3, 4, 5, or 6;

each R$^2$ and R$^3$ is, independently, H, alkyl, alkenyl, alkynyl, aryl, cycloalkyl, heterocycloalkyl, aralkyl, heteroaryl, heteroaralkyl, haloalkyl, halo, —OR$^{16}$, —OR$^{16}$, —N(R$^{17}$)$_2$, or —SR$^{16}$, or R$^2$ and R$^3$ taken together form a double bond or form a group

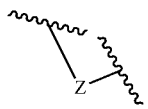

wherein Z is NR$^{17}$, O, or C(R$^{18}$)$_2$;
R$^4$ is independently H, halo, —OR$^{16}$, —N(R$^{17}$)$_2$, or —SR$^{16}$;

each $R^5$ and $R^6$, is, independently, H, alkyl, alkenyl, alkynyl, aryl, cycloalkyl, heterocycloalkyl, aralkyl, heteroaryl, heteroaralkyl, halo, —$OR^{16}$, —$N(R^{17})_2$, or —$SR^{16}$;

or $R^5$ and $R^6$ taken together with the carbon to which they are bonded, form C=O, C=S, C=N—$OR^{17}$, C=N—$R^{17}$, C=N—$N(R^{17})_2$, or form an optionally substituted 3-8 membered ring;

each $R^7$, $R^8$, $R^9$, $R^{10}$, $R^{11}$, $R^{12}$ and $R^{13}$ is, independently, H, alkyl, alkenyl, alkynyl, aryl, cycloalkyl, heterocycloalkyl, aralkyl, heteroaryl, heteroaralkyl, halo, —$OR^{16}$, —$N(R^{17})_2$, or —$SR^{16}$;

or $R^{10}$ and $R^{11}$ taken together, or $R^{11}$ and $R^{12}$ taken together, form a double bond or form a group

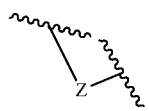

wherein Z is $NR^{17}$, O, or $C(R^{18})_2$;

each $R^{14}$ and $R^{15}$ is, independently, H, halo, —$OR^{16}$, —$N(R^{17})_2$, or —$SR^{16}$;

or $R^{14}$ and $R^{15}$ taken together with the carbon to which they are bonded, form C=O or C=S;

X is a bond or the group —$C(R^{19})_2$—; wherein each $R^{19}$ is, independently, H, alkyl, aralkyl, halo, —CN, —$OR^{16}$, or —$N(R^{17})_2$;

$R^{16}$ is H, alkyl, alkenyl, alkynyl, aryl, cycloalkyl, heterocycloalkyl, aralkyl, heteroaryl, heteroaralkyl or —$[C(R^{20})_2]_q$—$R^{21}$ wherein p is 0-6; or any two occurrences of $R^{16}$ on the same substituent are taken together to form a 4-8 membered optionally substituted ring;

$R^{17}$ is H, alkyl, alkenyl, alkynyl, aryl, cycloalkyl, heterocycloalkyl, aralkyl, heteroaryl, heteroaralkyl, —C(=O)$R^{20}$, —C(=O)O$R^{20}$, —SO$_2R^{20}$, —C(=O)N($R^{20}$)$_2$, or —[C($R^{20}$)$_2$]$_p$—$R^{21}$ wherein p is 0-6; or any two occurrences of $R^{17}$ on the same substituent are taken together to form a 4-8 membered optionally substituted ring;

$R^{18}$ is H, alkyl, alkenyl, alkynyl, aryl, cycloalkyl, heterocycloalkyl, aralkyl, heteroaryl, heteroaralkyl, halo, —CN, —$OR^{20}$, —OSi($R^{20}$)$_3$, —C(=O)$R^{20}$, —C(=O)O$R^{20}$, —SO$_2R^{20}$, or —C(=O)N($R^{20}$)$_2$;

$R^{20}$ is H, alkyl, alkenyl, alkynyl, aryl, cycloalkyl, heterocycloalkyl, aralkyl, heteroaryl, or heteroaralkyl; or any two occurrences of $R^{20}$ on the same substituent are taken together to form a 4-8 membered optionally substituted ring;

$R^{21}$ is —$OR^{22}$, —N($R^{22}$)C(=O)$R^{22}$, —N($R^{22}$)C(=O)O$R^{22}$, —N($R^{22}$)SO$_2$($R^{22}$), —C(=O)$R^{22}$N($R^{22}$)$_2$, —OC(=O)$R^{22}$N($R^{22}$)($R^{22}$), —SO$_2$N($R^{22}$)($R^{22}$), —N($R^{22}$)($R^{22}$), —C(=O)O$R^{22}$, —C(=O)N(OH)($R^{22}$), —OS(O)$_2$O$R^{22}$, —S(O)$_2$O$R^{22}$, —OP(=O)(O$R^{22}$)(O$R^{22}$), —N($R^{22}$)P(O)(O$R^{22}$)(O$R^{22}$), or —P(=O)(O$R^{22}$)(O$R^{22}$); and $R^{22}$ is H, alkyl, alkenyl, alkynyl, aryl, cycloalkyl, heterocycloalkyl, aralkyl, heteroaryl, heteroaralkyl; or any two occurrences of $R^{22}$ on the same substituent are taken together to form a 4-8 membered optionally substituted ring;

the process comprising contacting a compound of formula (I) or a salt thereof, an amino donor molecule, and an amine transaminase enzyme in a solution to provide a compound of formula (II) or a salt thereof.

In certain embodiments, $R^1$ is H, alkyl, alkenyl, alkynyl, aryl, cycloalkyl, heterocycloalkyl, aralkyl, heteroaryl, heteroaralkyl, haloalkyl, —$OR^{16}$, —C(O)$R^{16}$, —CO$_2R^{16}$, —SO$_2R^{16}$, —C(O)N($R^{17}$)($R^{17}$), or —[C($R^{16}$)$_2$]$_q$—$R^{16}$. In certain embodiments, $R^1$ is H, aralkyl, —C(O)$R^{16}$, —CO$_2R^{16}$, —SO$_2R^{16}$ or —C(O)N($R^{17}$)($R^{17}$). In certain embodiments, $R^1$ is H, aralkyl or —CO$_2R^{16}$.

In certain embodiments, $R^1$ is H.

In certain embodiments, $R^1$ is aralkyl.

In certain embodiments, $R^1$ is —CO$_2R^{16}$. In certain embodiments, $R^1$ is —CO$_2R^{16}$ and $R^{16}$ is alkyl, alkenyl, alkynyl, aryl, cycloalkyl, heterocycloalkyl, aralkyl, heteroaryl or heteroaralkyl. In certain embodiments, $R^1$ is a -Boc group (e.g., wherein $R^1$ is —CO$_2R^{16}$ and $R^{16}$ is t-butyl). In certain embodiments, $R^1$ is a -CBz group (e.g., wherein $R^1$ is —CO$_2R^{16}$ and $R^{16}$ is benzyl).

In certain embodiments, $R^2$ and $R^3$ taken together form a double bond.

In certain embodiments, $R^2$ and $R^3$ form a group:

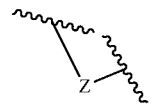

wherein Z is —$NR^{17}$—, —O—, or —$C(R^{18})_2$—. In certain embodiments, Z is —$C(R^{18})_2$—. In certain embodiments, Z is —CH$_2$—.

In certain embodiments, X is a bond. For example, in certain embodiments, wherein $R^2$ and $R^3$ are taken together form a double bond, or wherein $R^2$ and $R^3$ form a group:

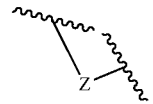

and Z is —$NR^{17}$—, —O—, or —$C(R^{18})_2$—, then X is a bond.

In certain embodiments, X is the group —$C(R^{19})_2$—. In certain embodiments, $R^{19}$ is H, e.g., wherein X is —CH$_2$—.

In certain embodiments, wherein $R^2$ and $R^3$ are taken together form a double bond, then X is the group —$C(R^{19})_2$—. In certain embodiments, wherein $R^2$ and $R^3$ are taken together form a double bond, then X is the group —CH$_2$—.

In certain embodiments, $R^4$ is H.

In certain embodiments, each $R^5$ and $R^6$, is, independently, H, or $R^5$ and $R^6$ taken together, along with the carbon to which they are bonded, form C=O. In certain embodiments, each of $R^5$ and $R^6$ is independently H. In certain embodiments, $R^5$ and $R^6$ taken together with the carbon to which they are bonded form C=O.

In certain embodiments, $R^7$ and $R^8$ are each H.

In certain embodiments, $R^9$ and $R^{10}$ are each H.

In certain embodiments, $R^{11}$ is a H.

In certain embodiments, $R^{12}$ and $R^{13}$ are each H.

In certain embodiments, $R^{14}$ and $R^{15}$ are each H.

In certain embodiments, each of $R^7$, $R^8$, $R^9$, $R^{10}$, $R^{11}$, $R^{12}$, $R^{13}$, $R^{14}$ and $R^{15}$ is H.

In certain embodiments, $R^9$ is H and $R^{10}$ and $R^{11}$ taken together form a double bond.

In certain embodiments, $R^{13}$ is H, and $R^{11}$ and $R^{12}$ taken together form a double bond.

In certain embodiments, the compound of formula (I) is a compound of the formula (I-AA):

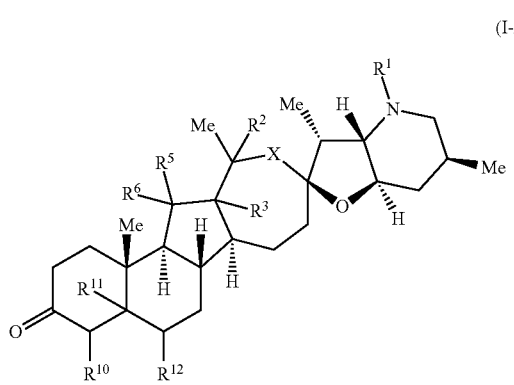

(I-AA)

or salt thereof, and the compound of formula (II) is a compound of the formula (II-AA):

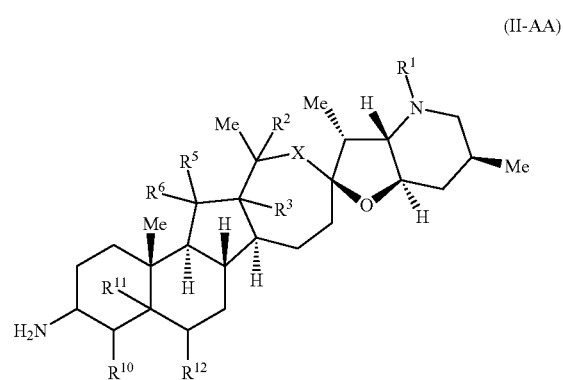

(II-AA)

or salt thereof, wherein $R^1$, $R^2$, $R^3$, $R^5$, $R^6$, $R^{10}$, $R^{11}$, $R^{12}$ and X are as defined herein.

In certain embodiments, the compound of formula (I) is a compound of the formula (I-BB):

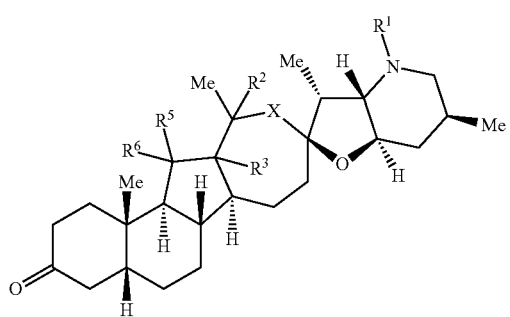

(I-BB)

or salt thereof, and the compound of formula (II) is a compound of the formula (II-BB):

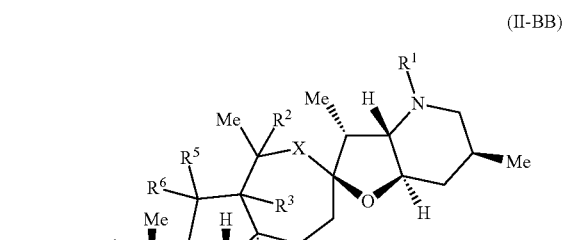

(II-BB)

or salt thereof, wherein $R^1$, $R^2$, $R^3$, $R^5$, $R^6$ and X are as defined herein.

In certain embodiments, the compound of formula (I) is a compound of the formula (I-CC):

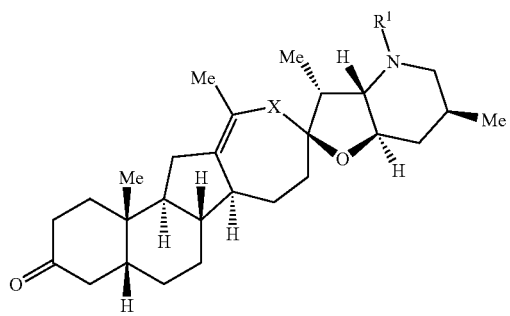

(I-CC)

or salt thereof, and the compound of formula (II) is a compound of the formula (II-CC):

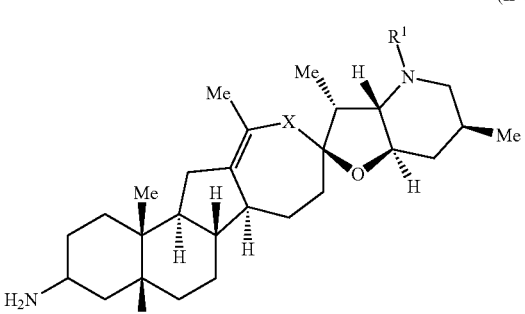

(II-CC)

or salt thereof, wherein $R^1$ and X are as defined herein.

Exemplary compounds of formula (I) are provided in U.S. Pat. No. 7,230,004, U.S. Pat. No. 7,407,967, U.S. Publication No. 20080293754, and U.S. Publication No. 20090012109, each of which is incorporated herein by reference in their entirety.

In certain embodiments, the compound of formula (I) or a salt thereof, and a compound of formula (II) or a salt thereof, are selected from the set of compounds, or salts thereof, provided in Tables 1, 2, 3 and 4, and wherein $R^1$ is as defined above and herein:

TABLE 1
Compound of formula (I)
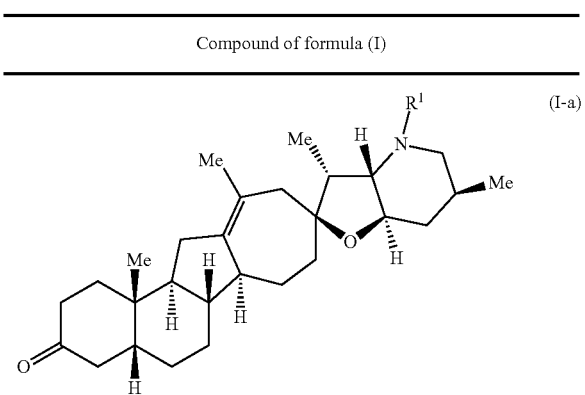
(I-a)
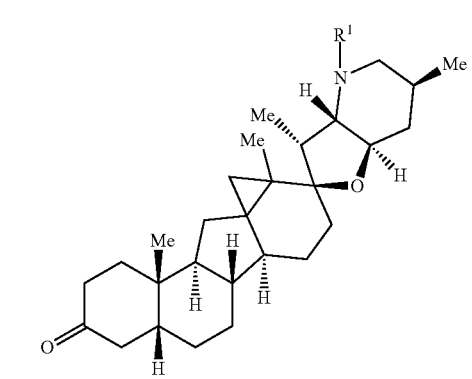
(I-b)
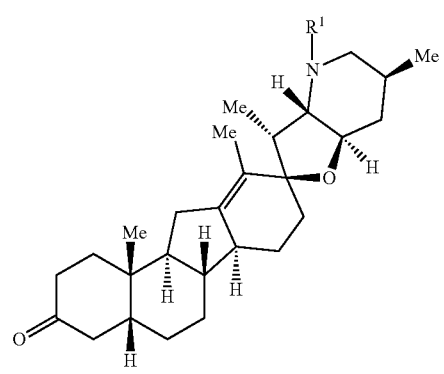
(I-c)
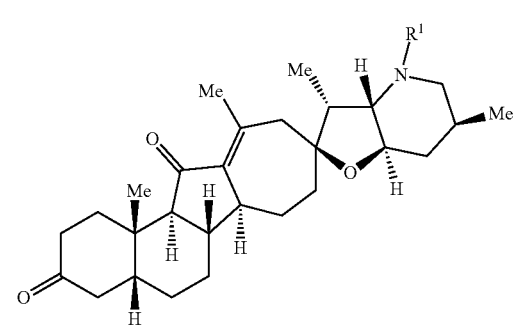
(I-d)
TABLE 1-continued
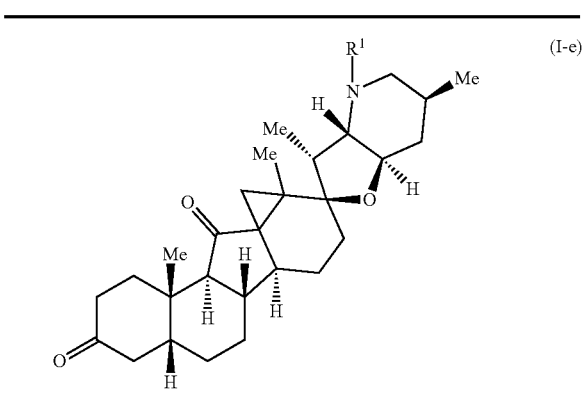
(I-e)
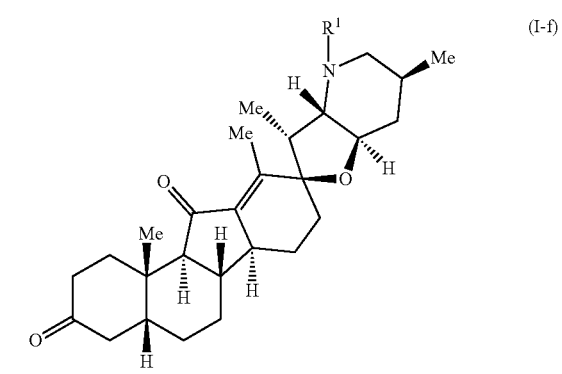
(I-f)
Compound of formula (II)
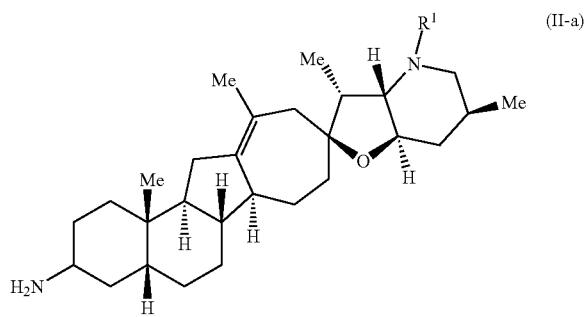
(II-a)
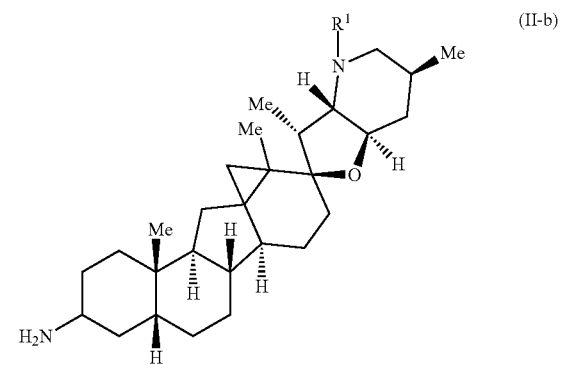
(II-b)

TABLE 1-continued
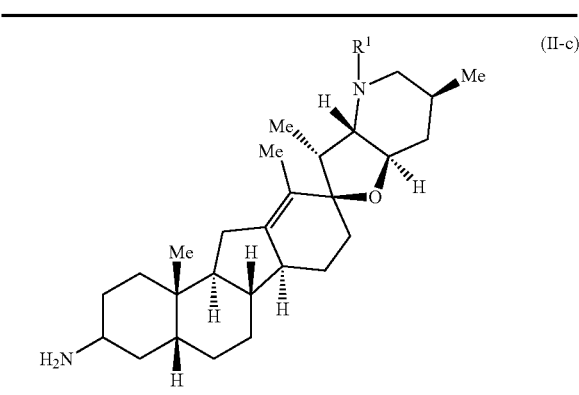
(II-c)
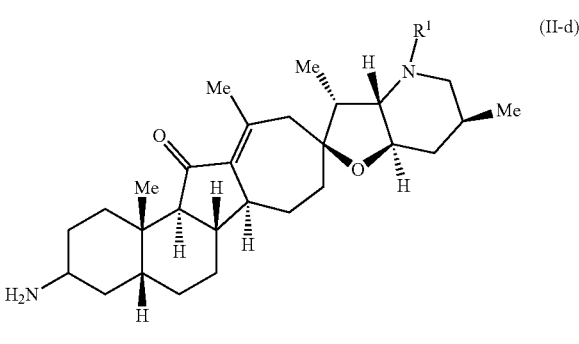
(II-d)
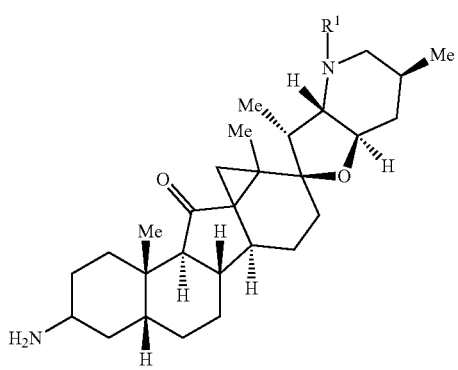
(II-e)
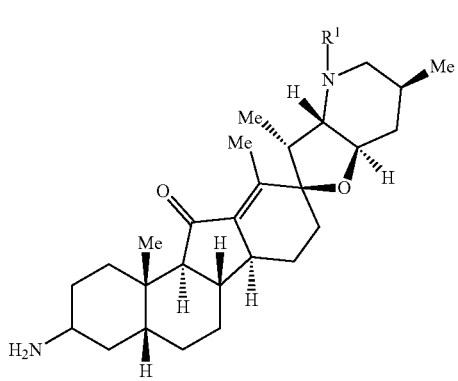
(II-f)
TABLE 2
Compound of formula (I)
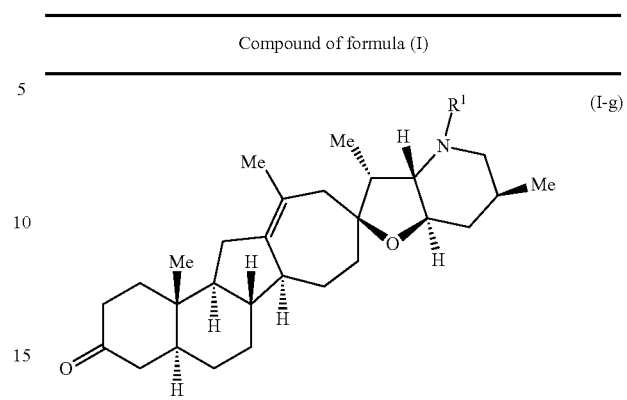
(I-g)
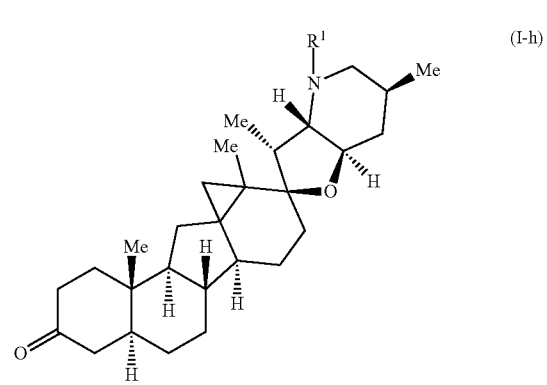
(I-h)
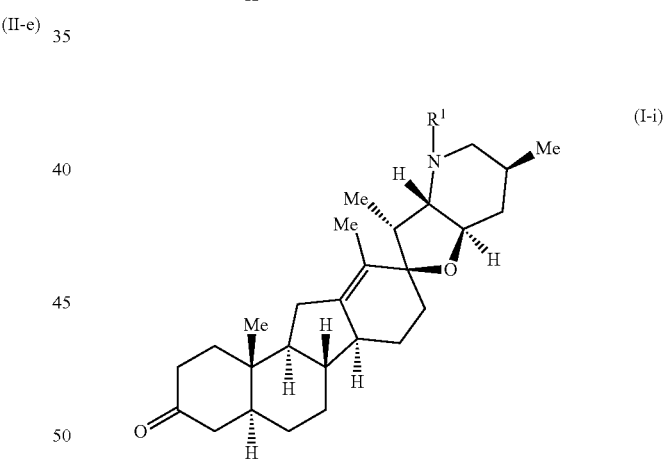
(I-i)
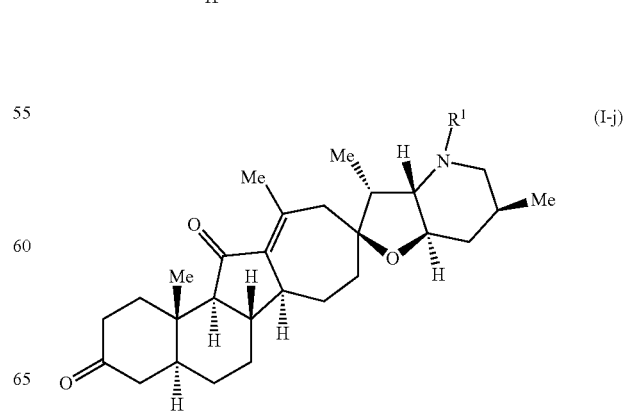
(I-j)

TABLE 2-continued
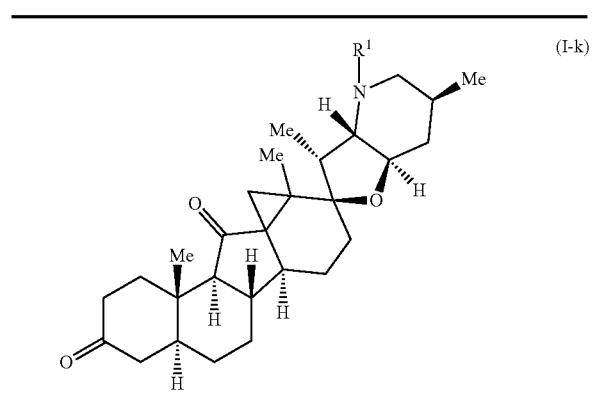
(I-k)
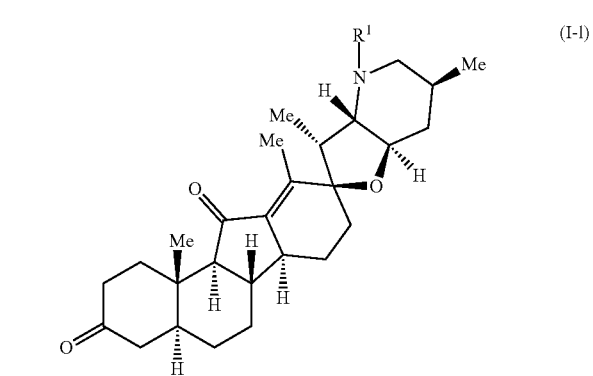
(I-l)
Compound of formula (II)
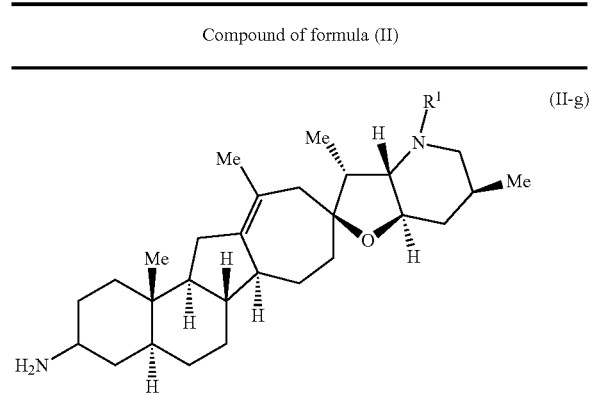
(II-g)
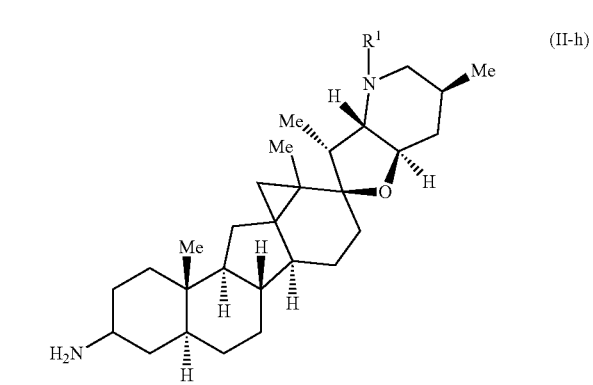
(II-h)
TABLE 2-continued
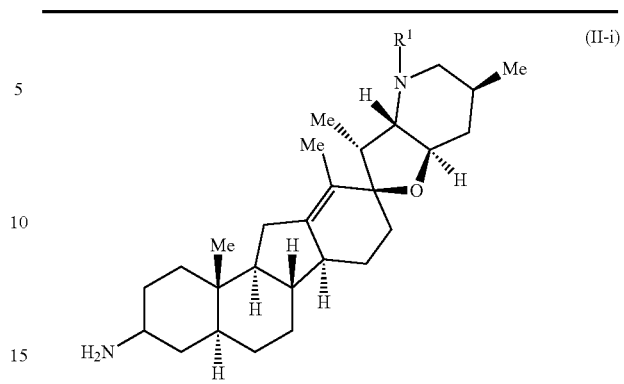
(II-i)
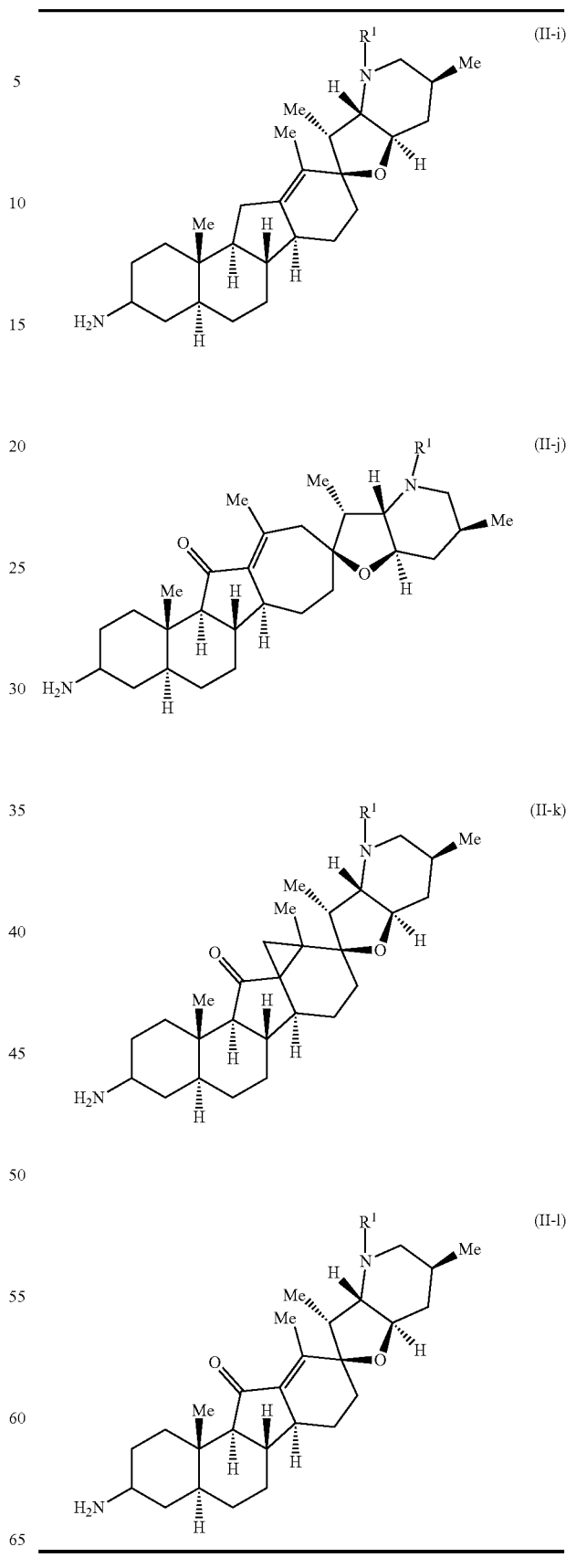
(II-j)
(II-k)
(II-l)

TABLE 3
Compound of formula (I)
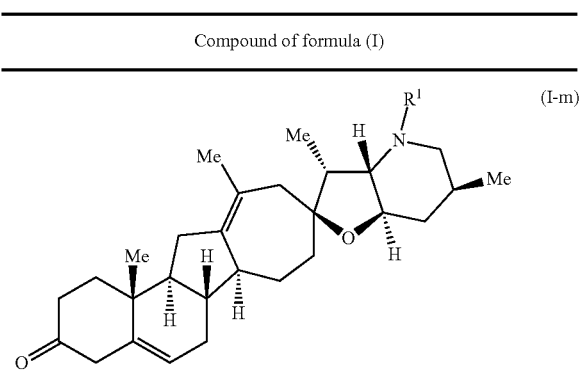
(I-m)
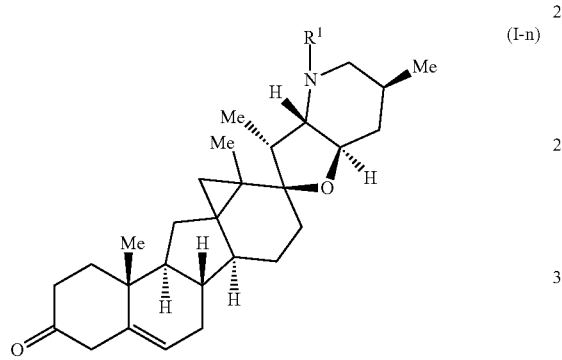
(I-n)
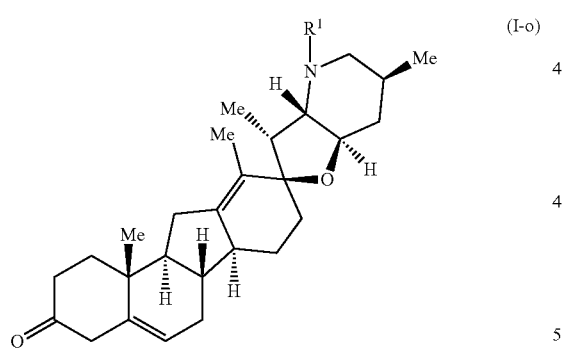
(I-o)
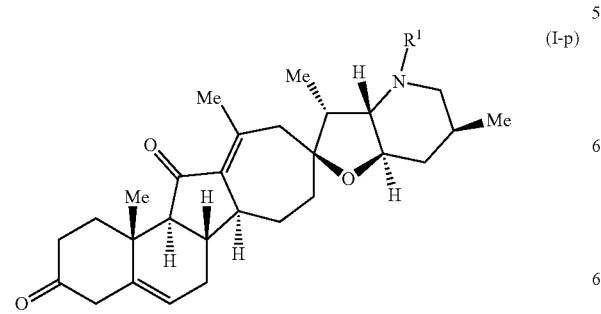
(I-p)
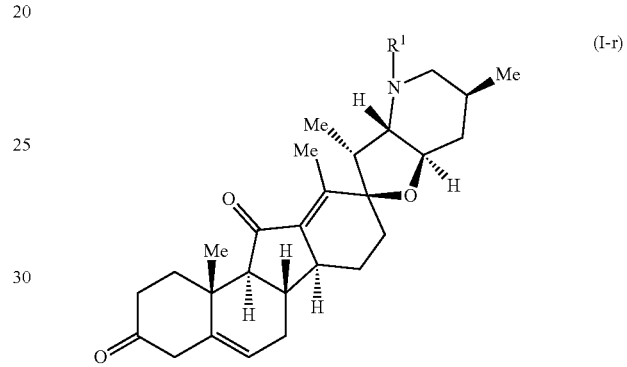
(I-q)
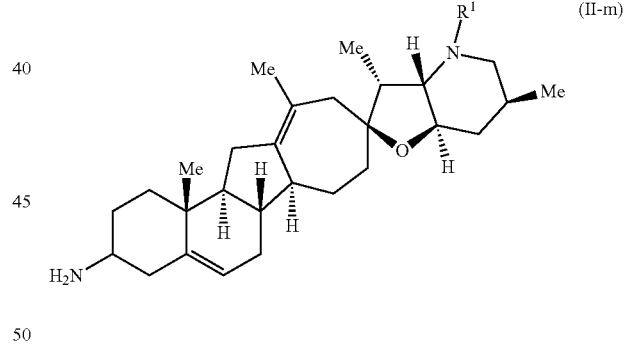
(I-r)
Compound of formula (II)
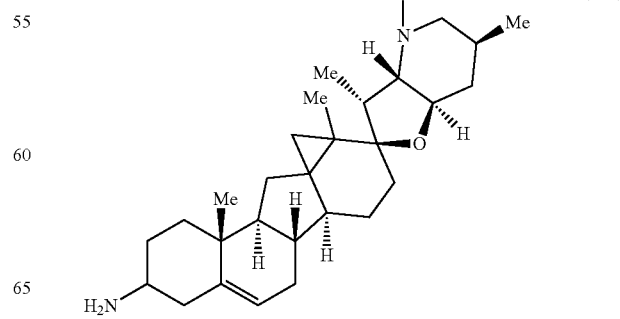
(II-m)
(II-n)

TABLE 3-continued
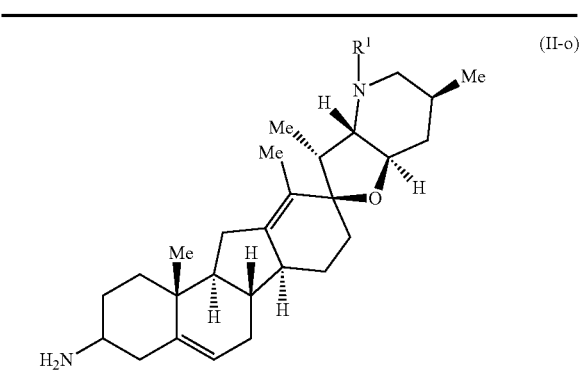
(II-o)
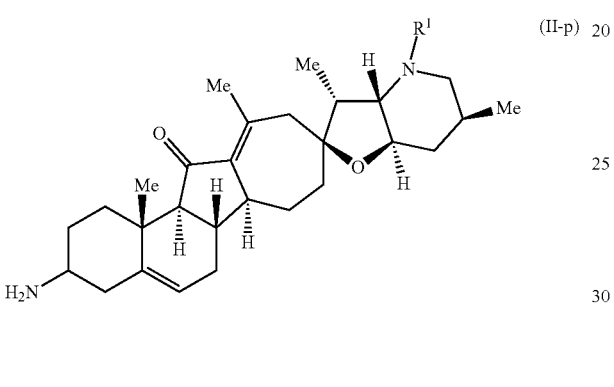
(II-p)
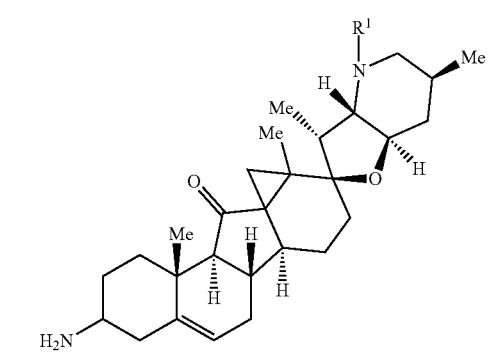
(II-q)
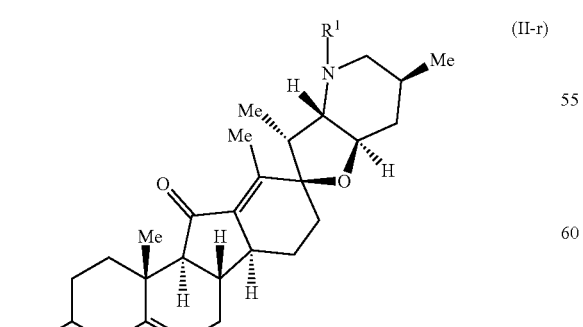
(II-r)
TABLE 4
Compound of formula (I)
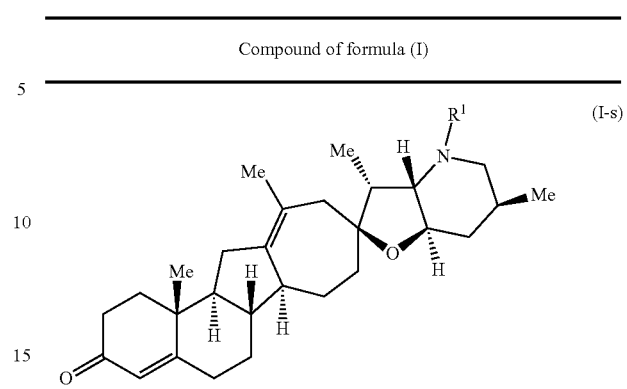
(I-s)
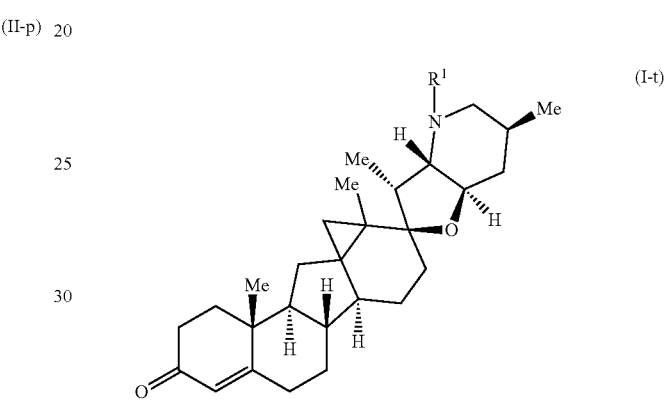
(I-t)
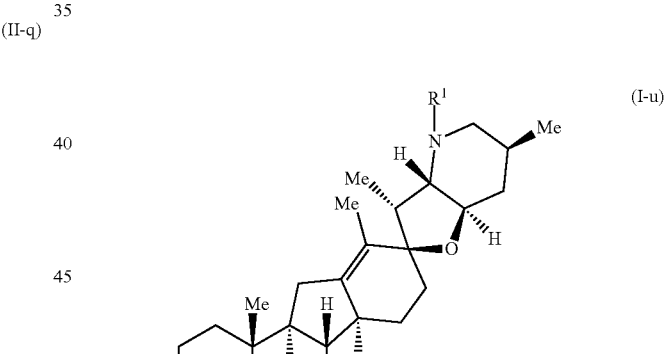
(I-u)
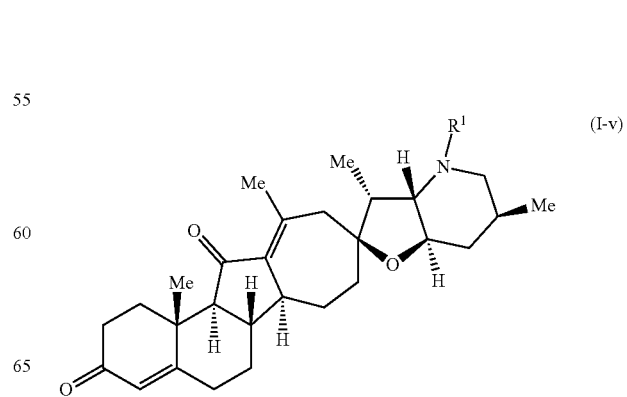
(I-v)

TABLE 4-continued

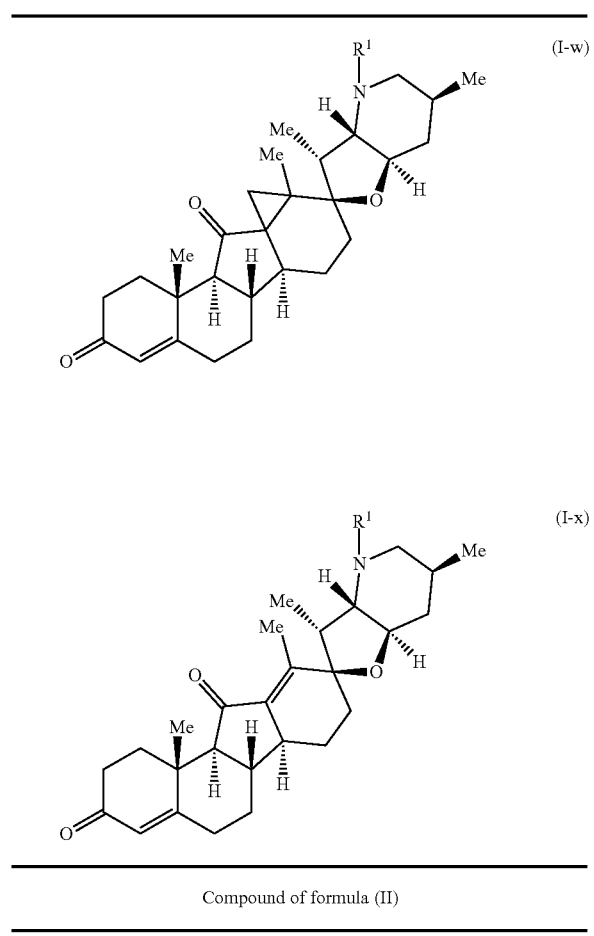

Compound of formula (II)

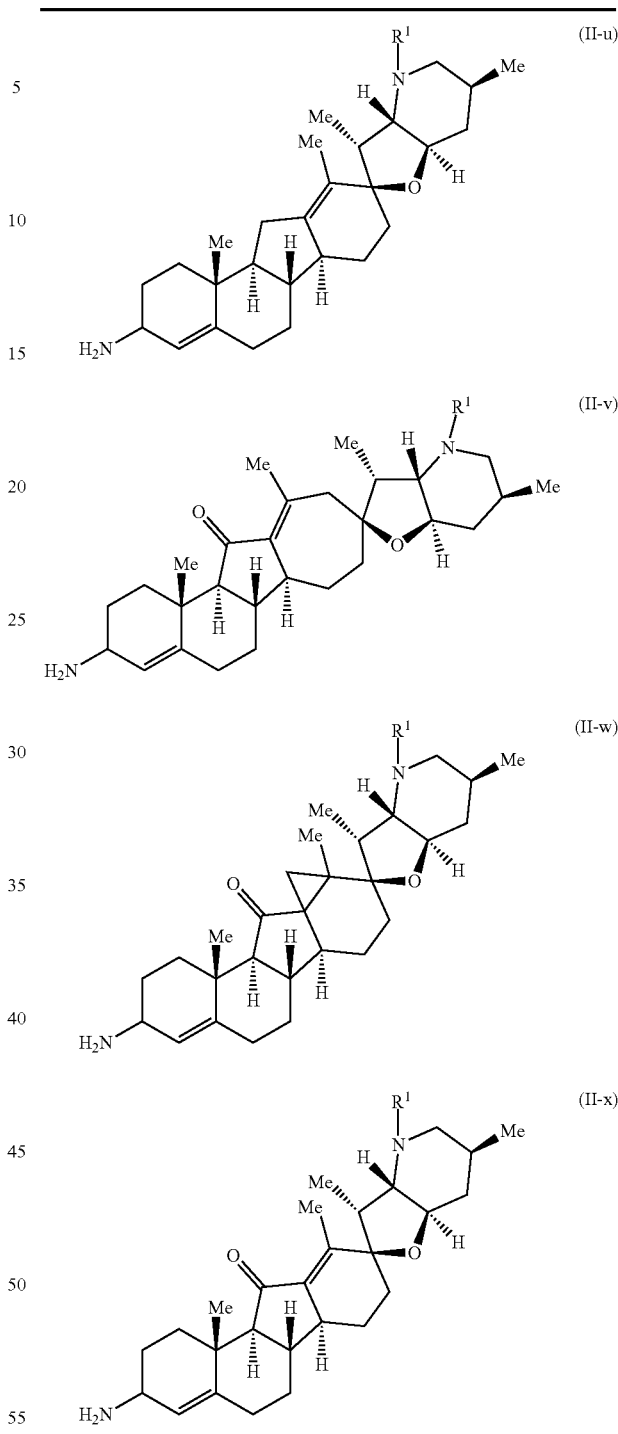

In certain embodiments, $R^1$ is H.

In certain embodiments, $R^1$ is aralkyl.

In certain embodiments, $R^1$ is $-CO_2R^{16}$. In certain embodiments, $R^1$ is $-CO_2R^{16}$ and $R^{16}$ is alkyl, alkenyl, alkynyl, aryl, cycloalkyl, heterocycloalkyl, aralkyl, heteroaryl or heteroaralkyl. In certain embodiments, $R^1$ is a -Boc group (e.g., wherein $R^1$ is $-CO_2R^{16}$ and $R^{16}$ is t-butyl). In certain embodiments, $R^1$ is a -CBz group (e.g., wherein $R^1$ is $-CO_2R^{16}$ and $R^{16}$ is benzyl).

In certain embodiments, the process preferentially generates a compound of formula (II), or a salt thereof, from a compound of formula (I), or salt thereof, wherein the newly-formed amino group provided in formula (II) has (R) or (S) stereochemistry.

For example, in certain embodiments, the process preferentially generates a compound of formula (II), or salt thereof, wherein the newly-formed amino group has (S) stereochemistry, e.g., a compound of the formula (S)-(II):

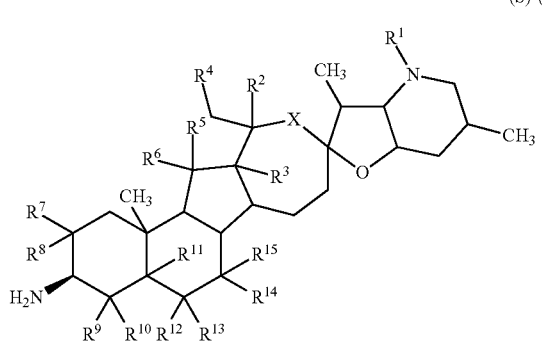

(S)-(II)

or a salt thereof,
wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and X are as defined herein.

In certain embodiments, the process preferentially generates a compound of formula (II), or salt thereof, wherein the newly-formed amino group has (R) stereochemistry, e.g., a compound of the formula (R)-(II):

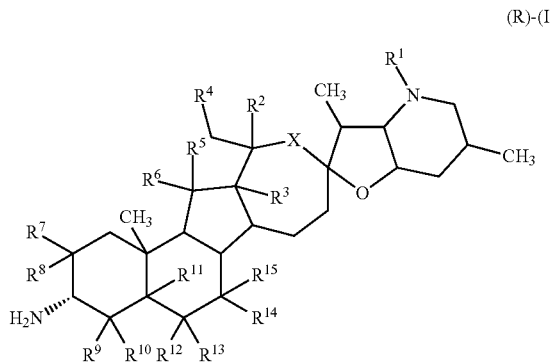

(R)-(II)

or a salt thereof,
wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and X are as defined herein.

As used herein, "preferentially generates" refers to the production of one stereoisomer of a compound of formula (II) in excess over the other stereoisomer. In certain embodiments, the process preferentially generates a compound of formula (II), or a salt thereof, wherein the newly-formed amino group has (R) or (S) stereochemistry, in greater than 40% diastereomeric excess (de), greater than 50% de, greater than 60% de, greater than 70% de, greater than 75% de, greater than 80% de, greater than 85% de, greater than 90% de, greater than 95% de, greater than 98% de, or greater than 99% de, as determined by HPLC.

In a preferred embodiment, the process preferentially generates a compound of formula (II), or salt thereof, wherein the newly-formed amino group has (R) stereochemistry.

For example, in certain embodiments, the compound of formula (I) is of the formula (I-AA):

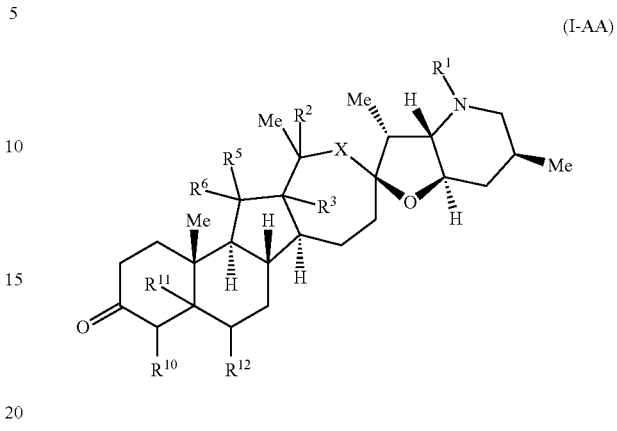

(I-AA)

or salt thereof,
and the compound of formula (II) is of the formula (R)-(II-AA):

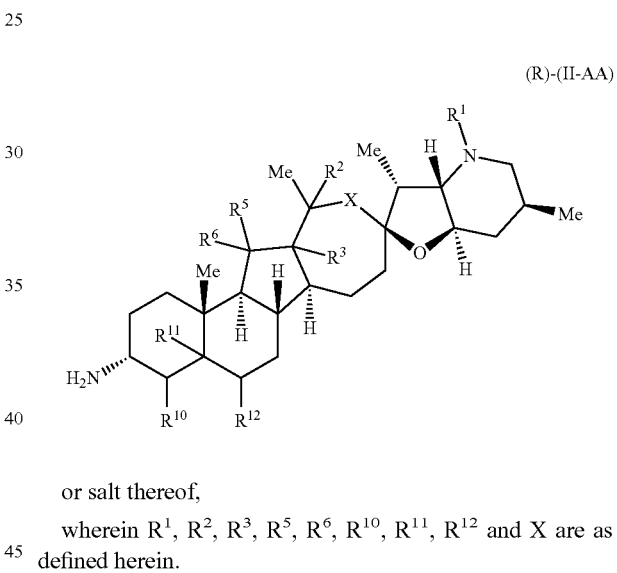

(R)-(II-AA)

or salt thereof,
wherein $R^1$, $R^2$, $R^3$, $R^5$, $R^6$, $R^{10}$, $R^{11}$, $R^{12}$ and X are as defined herein.

In certain embodiments, the compound of formula (I) is of the formula (I-BB):

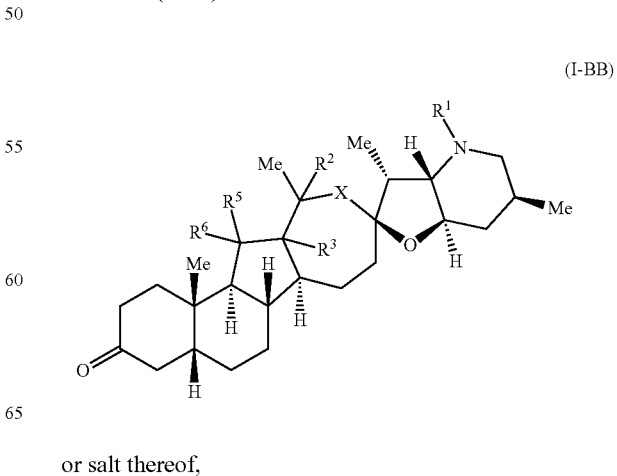

(I-BB)

or salt thereof, and the compound of formula (II) is of the formula (R)-(II-BB):

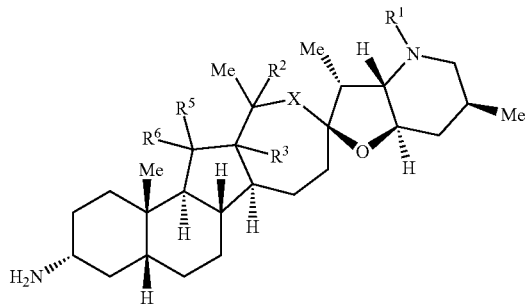

(R)-(II-BB)

or salt thereof,
wherein $R^1$, $R^2$, $R^3$, $R^5$, $R^6$ and X are as defined herein.

In certain embodiments, the compound of formula (I) is of the formula (I-CC):

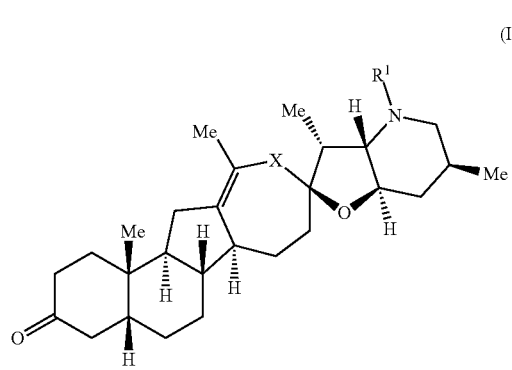

(I-CC)

or salt thereof,
and the compound of formula (II) is of the formula (R)-(II-CC):

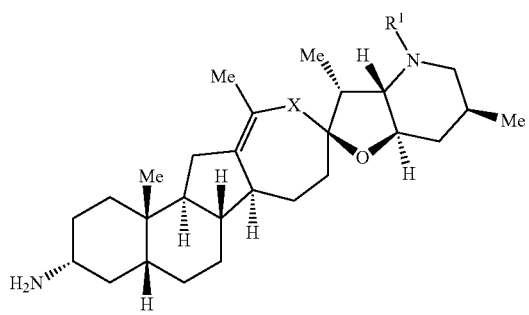

(R)-(II-CC)

or salt thereof,
wherein $R^1$ and X are as defined herein.

In another preferred embodiment, the compound of formulae (I) and (II) are selected from the set of compounds, or salts thereof, provided in Table 1.

In certain preferred embodiments, the process preferentially generates a compound of formula (II) of Table 1, or salt thereof, wherein the newly-formed amino group has (R) stereochemistry.

For example, in certain embodiments, the compound of formulae (I) and (II) are selected from a set of compounds, or salts thereof, provided in Table 5, wherein the newly-formed amino group of the compound of formula (II) has (R) stereochemistry:

TABLE 5

| Compound of formula (I) |
|---|

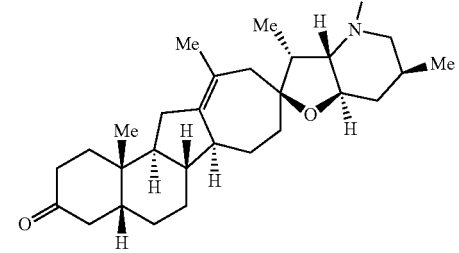

(I-a)

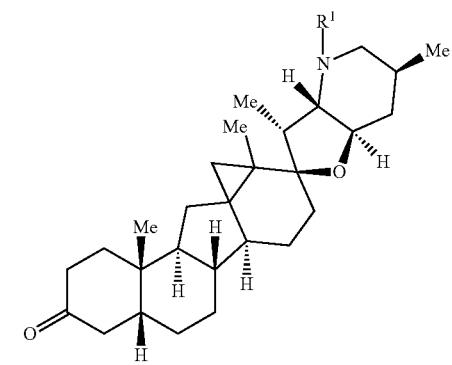

(I-b)

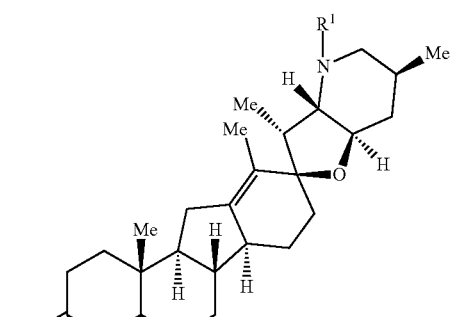

(I-c)

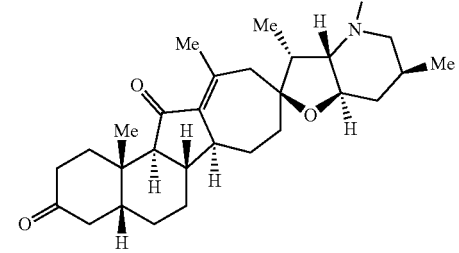

(I-d)

TABLE 5-continued
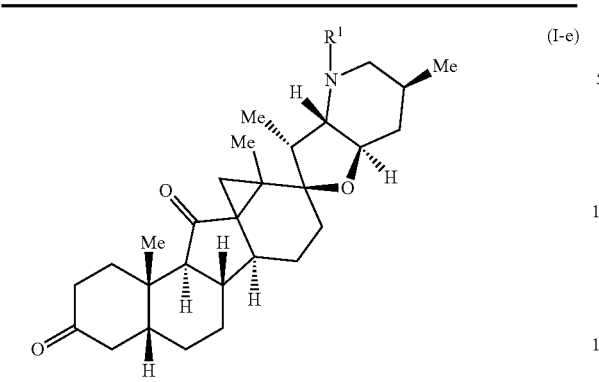
(I-e)
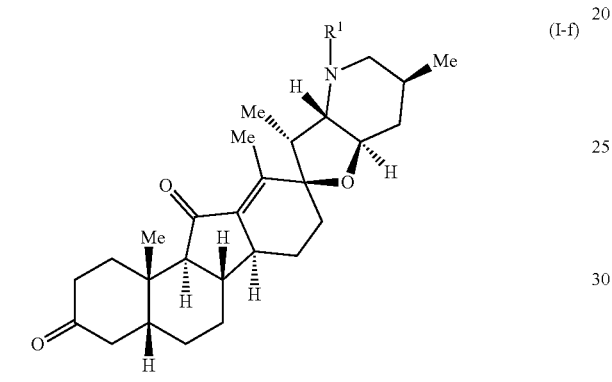
(I-f)
Compound of formula (II)
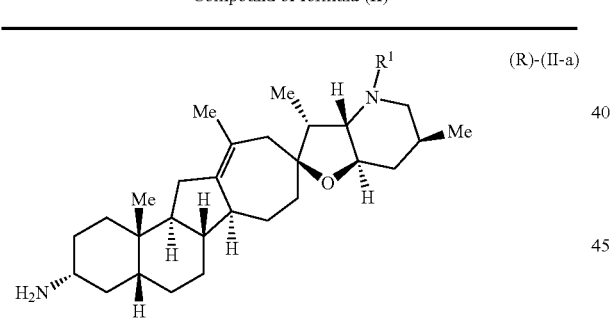
(R)-(II-a)
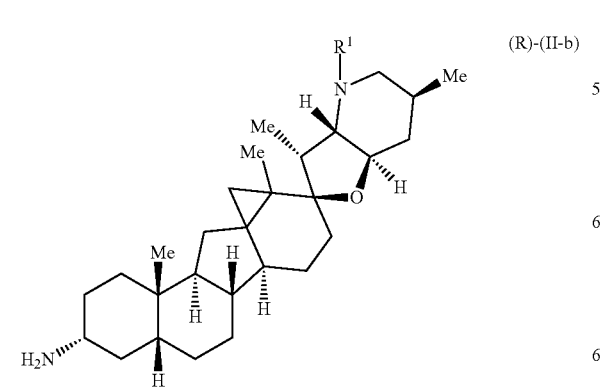
(R)-(II-b)
TABLE 5-continued
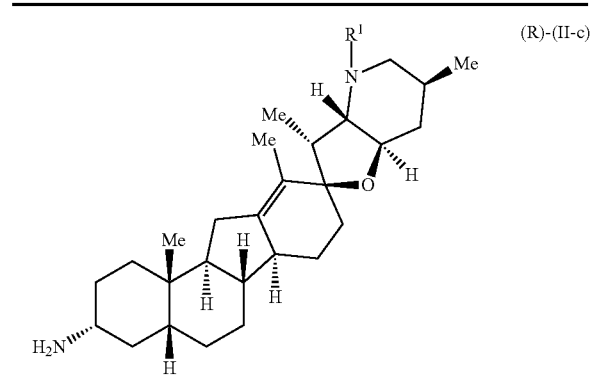
(R)-(II-c)
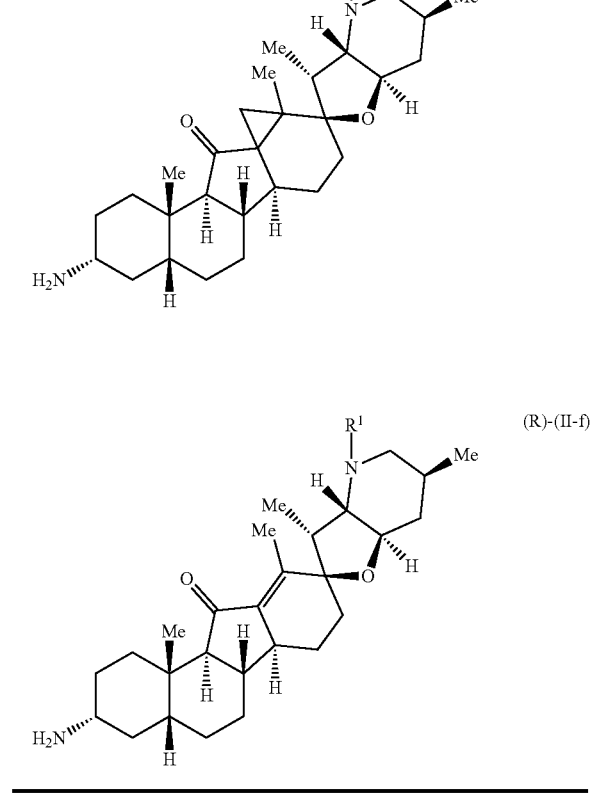
(R)-(II-d)
(R)-(II-e)
(R)-(II-f)

In certain embodiments, the compound of formula (I) is a compound of formula (I-a):

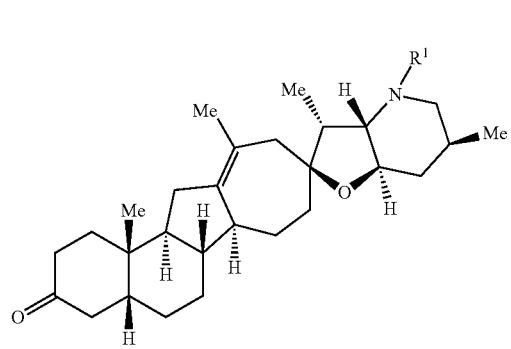

(I-a)

or salt thereof,
and the compound of formula (II) is a compound of formula (R)-(II-a):

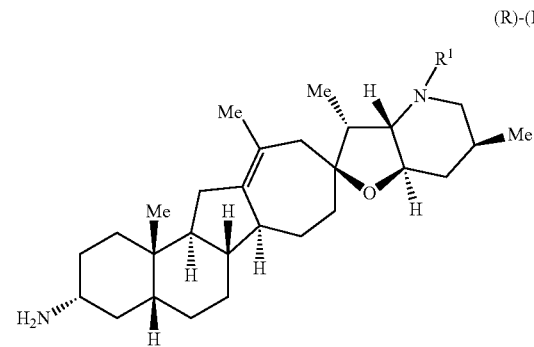

(R)-(II-a)

or a salt thereof;
wherein $R^1$ is as defined herein.

In certain embodiments, $R^1$ is H.

In certain embodiments, $R^1$ is aralkyl.

In certain embodiments, $R^1$ is —$CO_2R^{16}$. In certain embodiments, $R^1$ is —$CO_2R^{16}$ and $R^{16}$ is alkyl, alkenyl, alkynyl, aryl, cycloalkyl, heterocycloalkyl, aralkyl, heteroaryl or heteroaralkyl. In certain embodiments, $R^1$ is a -Boc group (e.g., wherein $R^1$ is —$CO_2R^{16}$ and $R^{16}$ is t-butyl). In certain embodiments, $R^1$ is a -CBz group (e.g., wherein $R^1$ is —$CO_2R^{16}$ and $R^{16}$ is benzyl).

Masked Ketones

In certain embodiments, the compound of formula (I) is a masked ketone. In this context, a "masked ketone" refers to a chemically modified compound of formula (I) or salt thereof containing a functional group which is transformed in situ (e.g., by hydrolysis) to the ketone.

Exemplary masked ketones include, but are not limited to, aminals and hemiaminals (see, for example, Vogel et al., *J. Org. Chem.* (2004) 69:4487-4491; Reeder and Meyers, *Tetrahedron Letters* (1999) 40:3115-3118, each of which is incorporated herein by reference), acetals and hemiacetals (see, for example, Boyce et al., *Bioorg. Med. Chem. Lett.* (2008) 18:5771-5773, incorporated herein by reference), hydrates (see, for example, Silverman et al., *J. Med. Chem.* (1987) 31:1566-1570, incorporated herein by reference), imines (see, for example, Hine et al., *J. Am. Chem. Soc.* (1970) 92:5194-5199, incorporated herein by reference), oximes (see, for example, Sha et al., *J. Am. Chem. Soc.* (2006) 128: 9687-9692, incorporated herein by reference), thiocarbonyls (see, for example, Kalm, *J. Chem. Soc.* (1961) 2925-2929, incorporated herein by reference), thioacetals and thiohemiacetals (see, for example Ogura et al., *Tetrahedron Letters* (1986) 27:3665-3668, incorporated herein by reference), enol ethers (see for example, Manis and Rathke, *J. Org. Chem.* (1981) 46:5348-5351, incorporated herein by reference), and salts thereof.

For example, provided is a process for preparing a compound of formula (II):

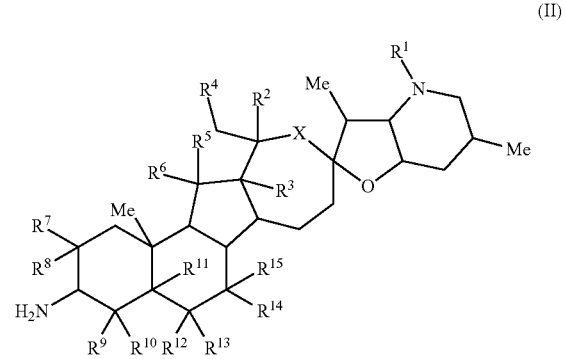

(II)

or a salt thereof;
from a masked ketone of a compound of formula (I):

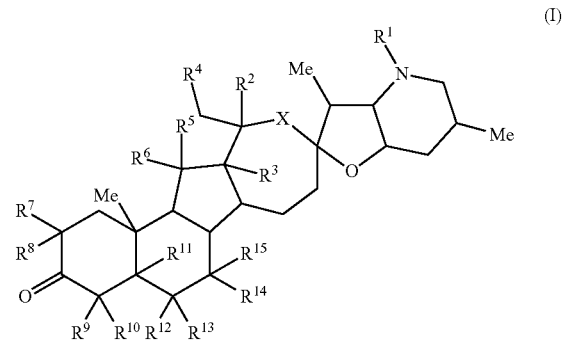

(I)

or salt thereof;
wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and X are as defined herein;

the process comprising contacting a masked ketone of a compound of formula (I) or a salt thereof, an amino donor molecule, and an amine transaminase enzyme in a solution to provide a compound of formula (II) or a salt thereof.

In certain embodiments, a compound of formula (I) is a masked ketone having the formula (I-DD):

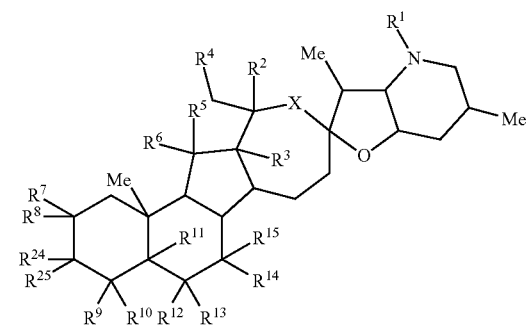

(I-DD)

or a salt thereof,
wherein:
$R^{24}$ and $R^{25}$ are selected from —$OR^{26}$, —$SR^{26}$, and —$N(R^{26})_2$,
or $R^{24}$ and $R^{25}$ are taken together to form the group =S, =N—$R^{26}$, or =N—$OR^{26}$,
or $R^{24}$ is —$OR^{27}$ or —O(C=O)$R^{27}$ and $R^{25}$ and $R^8$ or $R^{25}$ and $R^9$ are taken together to form a bond;

$R^{26}$ is H, alkyl, alkenyl, alkynyl, aryl, cycloalkyl, heterocycloalkyl, aralkyl, heteroaryl, heteroaralkyl, —C(=O)$R^{27}$, —C(=O)O$R^{27}$ or —C(=O)N($R^{28}$)$_2$, or any two occurrences of $R^{26}$ are taken together to form a 4-8 membered optionally substituted ring;

$R^{27}$ is alkyl, alkenyl, alkynyl, aryl, cycloalkyl, heterocycloalkyl, aralkyl, heteroaryl, or heteroaralkyl; and $R^{28}$ is H, alkyl, alkenyl, alkynyl, aryl, cycloalkyl, heterocycloalkyl, aralkyl, heteroaryl, or heteroaralkyl; or any two occurrences of $R^{28}$ on the same substituent are taken together to form a 4-8 membered optionally substituted ring.

In certain embodiments, a compound of formula (I-DD) or a salt thereof, is a hydrate, an acetal or a hemiacetal.

In certain embodiments, a compound of formula (I-DD) or a salt thereof, is a hydrate, an acetal or a hemiacetal of the formula (I-EE):

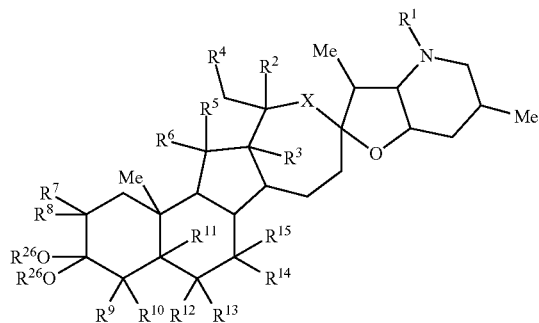

(I-EE)

or a salt thereof,
wherein:

$R^{26}$ is H, alkyl, alkenyl, alkynyl, aryl, cycloalkyl, heterocycloalkyl, aralkyl, heteroaryl, heteroaralkyl, —C(=O)$R^{27}$, —C(=O)O$R^{27}$ or —C(=O)N($R^{28}$)$_2$, or any two occurrences of $R^{26}$ are taken together to form a 4-8 membered optionally substituted ring;

$R^{27}$ is alkyl, alkenyl, alkynyl, aryl, cycloalkyl, heterocycloalkyl, aralkyl, heteroaryl, or heteroaralkyl; and $R^{28}$ is H, alkyl, alkenyl, alkynyl, aryl, cycloalkyl, heterocycloalkyl, aralkyl, heteroaryl, or heteroaralkyl; or any two occurrences of $R^{28}$ on the same substituent are taken together to form a 4-8 membered optionally substituted ring.

In certain embodiments, a compound of formula (I-DD) or a salt thereof, is a aminal or hemiaminal.

In certain embodiments, a compound of formula (I-DD), or a salt thereof, is a aminal or hemiaminal of the formula (I-FF):

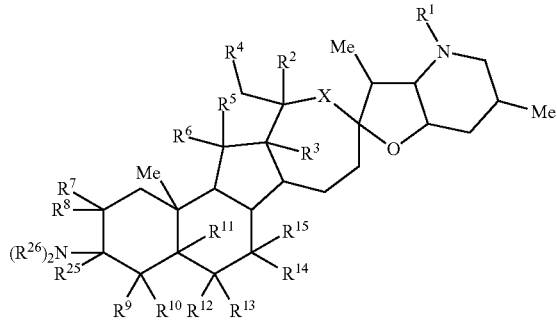

(I-FF)

or a salt thereof,
wherein:

$R^{25}$ is —O$R^{26}$ or —N($R^{26}$)$_2$;

$R^{26}$ is H, alkyl, alkenyl, alkynyl, aryl, cycloalkyl, heterocycloalkyl, aralkyl, heteroaryl, heteroaralkyl, —C(=O)$R^{27}$, —C(=O)O$R^{27}$ or —C(=O)N($R^{28}$)$_2$, or any two occurrences of $R^{26}$ are taken together to form a 4-8 membered optionally substituted ring;

$R^{27}$ is alkyl, alkenyl, alkynyl, aryl, cycloalkyl, heterocycloalkyl, aralkyl, heteroaryl, or heteroaralkyl; and $R^{28}$ is H, alkyl, alkenyl, alkynyl, aryl, cycloalkyl, heterocycloalkyl, aralkyl, heteroaryl, or heteroaralkyl; or any two occurrences of $R^{28}$ on the same substituent are taken together to form a 4-8 membered optionally substituted ring.

In certain embodiments, a compound of formula (I-DD) or a salt thereof, is a thioacetal or thiohemiacetal.

In certain embodiments, a compound of formula (I-DD) or a salt thereof, is a thioacetal or thiohemiacetal of the formula (I-GG):

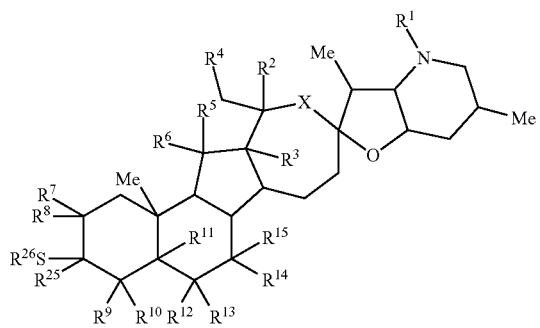

(I-GG)

or a salt thereof,
wherein:

$R^{25}$ is —O$R^{26}$ or —S$R^{26}$;

$R^{26}$ is H, alkyl, alkenyl, alkynyl, aryl, cycloalkyl, heterocycloalkyl, aralkyl, heteroaryl, heteroaralkyl, —C(=O)$R^{27}$, —C(=O)O$R^{27}$ or —C(=O)N($R^{28}$)$_2$, or any two occurrences of $R^{26}$ are taken together to form a 4-8 membered optionally substituted ring;

$R^{27}$ is alkyl, alkenyl, alkynyl, aryl, cycloalkyl, heterocycloalkyl, aralkyl, heteroaryl, or heteroaralkyl; and $R^{28}$ is H, alkyl, alkenyl, alkynyl, aryl, cycloalkyl, heterocycloalkyl, aralkyl, heteroaryl, or heteroaralkyl; or any two occurrences of $R^{28}$ on the same substituent are taken together to form a 4-8 membered optionally substituted ring.

In certain embodiments, a compound of formula (I-DD) or a salt thereof, is an imine.

In certain embodiments, a compound of formula (I-DD) or a salt thereof, is an imine of the formula (I-HH):

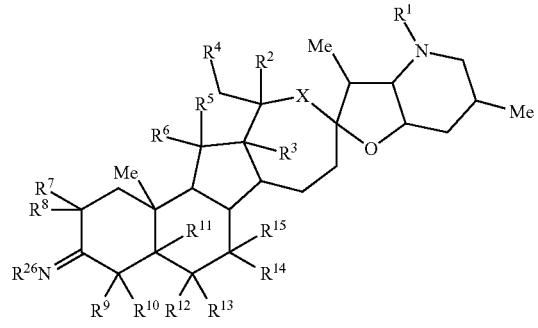

(I-HH)

or, a salt thereof,
wherein:

$R^{26}$ is H, alkyl, alkenyl, alkynyl, aryl, cycloalkyl, heterocycloalkyl, aralkyl, heteroaryl, heteroaralkyl, —C(=O)$R^{27}$, —C(=O)O$R^{27}$ or —C(=O)N($R^{28}$)$_2$;

$R^{27}$ is alkyl, alkenyl, alkynyl, aryl, cycloalkyl, heterocycloalkyl, aralkyl, heteroaryl, or heteroaralkyl; and $R^{28}$ is H, alkyl, alkenyl, alkynyl, aryl, cycloalkyl, heterocycloalkyl, aralkyl, heteroaryl, or heteroaralkyl; or any two occurrences of $R^{28}$ on the same substituent are taken together to form a 4-8 membered optionally substituted ring.

In certain embodiments, a compound of formula (I-DD) or a salt thereof, is an oxime.

In certain embodiments, a compound of formula (I-DD) or a salt thereof, is an oxime of the formula (I-JJ):

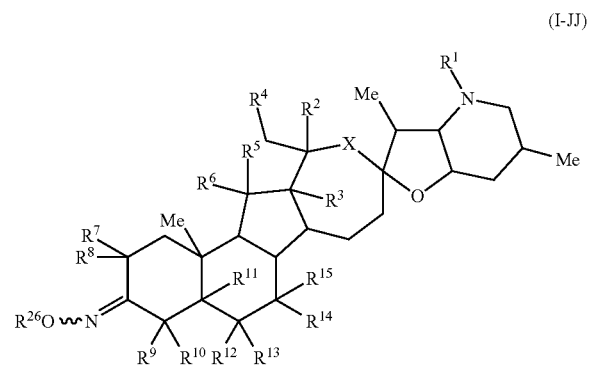

(I-JJ)

or a salt thereof,
wherein:

$R^{26}$ is H, alkyl, alkenyl, alkynyl, aryl, cycloalkyl, heterocycloalkyl, aralkyl, heteroaryl, heteroaralkyl, —C(=O)OR$^{27}$, —C(=O)OR$^{27}$ or —C(=O)N(R$^{28}$)$_2$;

$R^{27}$ is alkyl, alkenyl, alkynyl, aryl, cycloalkyl, heterocycloalkyl, aralkyl, heteroaryl, or heteroaralkyl; and $R^{28}$ is H, alkyl, alkenyl, alkynyl, aryl, cycloalkyl, heterocycloalkyl, aralkyl, heteroaryl, or heteroaralkyl; or any two occurrences of $R^{28}$ on the same substituent are taken together to form a 4-8 membered optionally substituted ring:

In certain embodiments, a compound of formula (I-DD) or a salt thereof, is a thiocarbonyl.

In certain embodiments, a compound of formula (I-DD) or a salt thereof, is a thiocarbonyl of the formula (I-KK):

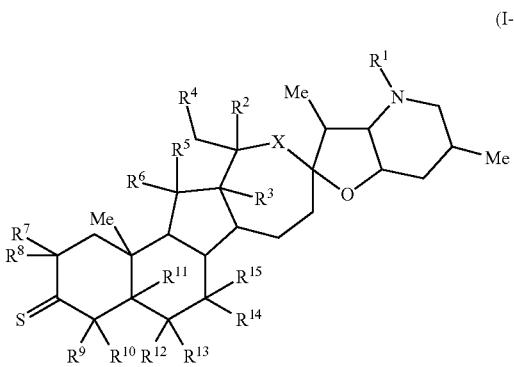

(I-KK)

or a salt thereof.

In certain embodiments, a compound of formula (I-DD) or a salt thereof, is an enol ether.

In certain embodiments, a compound of formula (I-DD) or a salt thereof, is an enol ether of the formulae (I-LL) or (I-MM):

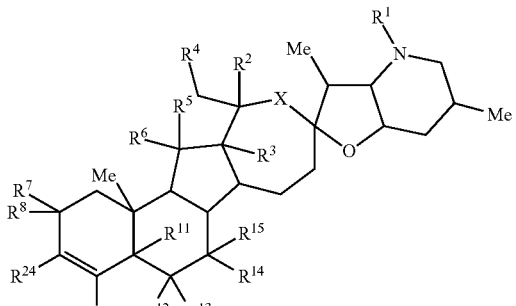

(I-LL)

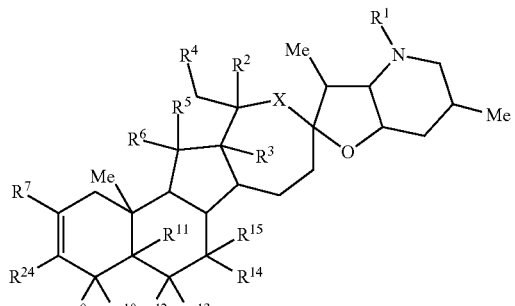

(I-MM)

or a mixture thereof and/or a salt thereof, wherein $R^{24}$ is —OR$^{27}$ or —O(C=O)R$^{27}$ and $R^{27}$ is alkyl, alkenyl, alkynyl, aryl, cycloalkyl, heterocycloalkyl, aralkyl, heteroaryl, or heteroaralkyl.

Amino Donor Molecule

An "amino donor molecule" is a compound having an —NH$_2$ group which, during the course of the reaction, is transferred to the compound of formula (I). Amino donor molecules include both amines and amino acids.

In certain embodiments, the amino donor molecule is an amine or salt thereof (e.g., a primary amine). Exemplary amine include, but are not limited to, pyridoxamine, methylbenzylamine, 2-aminobutane, propyl amine, isopropyl amine, 1,1,1-trifluoropropan-2-amine, 1,1,1,3,3,3-hexafluoropropan-2-amine, benzyl amine, 2-amino-1-butanol, 1-amino-1-phenylethane, 1-amino-1-(2-methoxy-5-fluorophenyl)ethane, 1-amino-1-phenylpropane, 1-amino-1-(4-hydroxyphenyl)propane, 1-amino-1-(4-bromophenyl)propane, nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, dimethoxy-4-methylphenyl)-2-aminobutane, 1-phenyl-3-aminobutane, 1-(4-hydroxyphenyl)-3-aminobutane, 1-amino-1-(2-naphthyl)ethane, cis-2-methylcyclopentanamine, trans-2-methylcyclopentanamine, cis-3-methylcyclopentanamine, trans-3-methylcyclopentanamine, cis-2-ethylcyclopentanamine, trans-2-ethylcyclopentanamine, cis-3-ethylcyclopentanamine, trans-3-ethylcyclopentanamine, cis-2-methylcyclohexanamine, trans-2-methylcyclohexanamine, cis-3-methylcyclohexanamine, trans-3-methylcyclohexanamine, cis-2-ethylcyclohexanamine, trans-2-ethylcyclohexanamine, cis-3-ethylcyclohexanamine; trans-3-ethylcyclohexanamine, 1-aminotetralin, 2-aminotetralin, 2-amino-5-methoxytetralin, 1-aminoindane, 2-aminoindane, 2-amino-1-propanol, cis-1-amino-2-indanol, trans-1-amino-2-indanol, 1-amino-6-hydroxyindanamine, taurine, and salts thereof.

In certain embodiments, the amino donor molecule is an amino acid or a polypeptide thereof and/or a salt thereof. A polypeptide, as used herein, refers to two or more amino acids joined by a peptide bond. In certain embodiments, the polypeptide is a dipeptide (e.g., two amino acids joined by a peptide bond).

In certain embodiments, the amino acid is selected from glycine, alanine, aspartic acid, phenylalanine, 2-aminopentanedioic acid, 3-aminobutyrate, γ-aminobutyrate, β-alanine, asparagine, cysteine, glutamic acid, glutamine, proline, selenocysteine, serine, tyrosine, arginine, histidine, ornithine, isoleucine, leucine, lysine, methionine, threonine, tryptophan, valine, and polypeptides thereof and/or salts thereof.

In certain embodiments, the amino donor molecule is a chiral amino donor molecule or a salt thereof, e.g., an amino donor molecule containing at least one asymmetric center. In certain embodiments, the amino group (—NH$_2$) to be transferred is attached to a chiral carbon. In certain embodiments, the chiral carbon has (R)-stereochemistry. In certain embodiments, the chiral carbon has (S)-stereochemistry.

In certain embodiments, the chiral amino donor molecule is a chiral amine or a salt thereof, e.g., an amine containing at least one asymmetric center. Exemplary chiral amines include, but are not limited to, (R)-methylbenzylamine, (S)-methylbenzylamine, (S)-2-aminobutane, (R)-2-aminobutane, (S)-1-amino indane, (R)-1-aminoindane, (R)-1,1,1-trifluoropropan-2-amine, (S)-1,1,1-trifluoropropan-2-amine, (R)-2-amino-1-propanol, (S)-2-amino-1-propanol, (1R,2S)-cis-1-amino-2-indanol, (1R,2R)-trans-1-amino-2-indanol, 1-(R)-amino-6-hydroxyindanamine, 1-(S)-amino-6-hydroxyindanamine, (R)-2-amino-1-butanol, (S)-2-amino-1-butanol, (R)-1-amino-1-phenylethane, (S)-1-amino-1-phenyl ethane, (R)-1-amino-1-(2-methoxy-5-fluorophenyl) ethane, (S)-1-amino-1-(2-methoxy-5-fluorophenyl)ethane, (R)-1-amino-1-phenylpropane, (S)-1-amino-1-phenylpropane, (R)-1-amino-1-(4-hydroxyphenyl)-propane, (S)-1-amino-1-(4-hydroxyphenyl)-propane, (R)-1-amino-1-(4-bromophenyl)propane, (S)-1-amino-1-(4-bromophenyl) propane, (R)-1-amino-1-(4-nitrophenyl)propane, (S)-1-amino-1-(4-nitrophenyl)propane, (R)-1-phenyl-2-aminopropane, (S)-1-phenyl-2-aminopropane, (R)-1-(3-trifluoromethylphenyl)-2-aminopropane, (S)-1-(3-trifluoromethylphenyl)-2-aminopropane (R)-1-amino-1-phenylbutane, (S)-1-amino-1-phenylbutane, (R)-1-phenyl-2-aminobutane, (S)-1-phenyl-2-aminobutane, (R)-1-(2,5-dimethoxy-4-methylphenyl)-2-aminobutane, (S)-1-(2,5-dimethoxy-4-methylphenyl)-2-aminobutane, (R)-1-phenyl-3-aminobutane, (S)-1-phenyl-3-aminobutane, (R)-1-(4-hydroxyphenyl)-3-aminobutane, (S)-1-(4-hydroxyphenyl)-3-aminobutane, (R)-1-amino-1-(2-naphthyl)ethane, (S)-1-amino-1-(2-naphthyl)ethane (R)-1-aminotetralin, (S)-1-aminotetralin, (R)-2-aminotetralin, (S)-2-aminotetralin, (R)-2-amino-5-methoxytetralin, (S)-2-amino-5-methoxytetralin, (1R,2S)-cis-2-methylcyclopentanamine, (1S,2R)-cis-2-methylcyclopentanamine, (1R,2R)-trans-2-methylcyclopentanamine, (1S,2S)-trans-2-methylcyclopentanamine, (1R,3S)-cis-3-methylcyclopentanamine, (1S,3R)-cis-3-methylcyclopentanamine, (1R,3R)-trans-3-methylcyclopentanamine, (1S,3S)-trans-3-methylcyclopentanamine, (1R,2S)-cis-2-ethylcyclopentanamine, (1S,2R)-cis-2-ethylcyclopentanamine, (1R,2R)-trans-2-ethylcyclopentanamine, (1S,2S)-trans-2-ethylcyclopentanamine, (1R,3S)-cis-3-ethylcyclopentanamine, (1S,3R)-cis-3-ethylcyclopentanamine, (1R,3R)-trans-3-ethylcyclopentanamine, (1S,3S)-trans-3-ethylcyclopentanamine, (1R,2S)-cis-2-methylcyclohexanamine, (1S,2R)-cis-2-methylcyclohexanamine, (1R,2R)-trans-2-methylcyclohexanamine, (1S,2S)-trans-2-methylcyclohexanamine, (1R,3S)-cis-3-methylcyclohexanamine, (1S,3R)-cis-3-methylcyclohexanamine, (1R,3R)-trans-3-methylcyclohexanamine, (1S,3S)-trans-3-methylcyclohexanamine, (1R,2S)-cis-2-ethylcyclohexanamine, (1S,2R)-cis-2-ethylcyclohexanamine; (1R,2R)-trans-2-ethylcyclohexanamine, (1S,2S)-trans-2-ethylcyclohexanamine, (1R,3S)-cis-3-ethylcyclohexanamine, (1S,3R)-cis-3-ethylcyclohexanamine, (1R,3R)-trans-3-ethylcyclohexanamine, (1S,3S)-trans-3-ethylcyclohexanamine, and salts thereof.

In certain embodiments, the chiral amino donor molecule is a chiral amino acid or a polypeptide thereof and/or a salt thereof, e.g., containing at least one asymmetric center. Exemplary chiral amino acids include, but are not limited to, (L)-alanine, (D)-alanine, (L)-aspartic acid, (D)-aspartic acid, (L)-phenylalanine, (D)-phenylalanine, (2S)-2-aminopentanedioic acid, (L)-asparagine, (D)-asparagine, (L)-cysteine, (D)-cysteine, (L)-glutamine, (D)-glutamine, (L)-glutamic acid, (D)-glutamic acid, (L)-proline, (D)-proline, (L)-selenocysteine, (D)-selenocysteine, (L)-serine, (D)-serine, (L)-tyrosine, (D)-tyrosine, (L)-arginine, (D)-arginine, (L)-histidine, (D)-histidine, (L)-isoleucine, (D)-isoleucine, (L)-leucine, (D)-leucine, (L)-lysine, (D)-lysine, (L)-methionine, (D)-methionine, (L)-threonine, (D)-threonine, (L)-tryptophan, (D)-tryptophan, (L)-valine, (D)-valine, (L)-ornithine, (D)-ornithine, (3R)-aminobutyrate, (3S)-aminobutyrate and polypeptides thereof and/or salts thereof.

In certain embodiments, the chiral amino donor molecule is (R)-methylbenzylamine or a salt thereof. In other embodiments, the chiral amino donor molecule is (S)-methylbenzylamine or a salt thereof.

In certain embodiments, the chiral amino donor molecule is (L)-alanine or a salt thereof. In certain embodiments, the chiral amino donor molecule is (D)-alanine or a salt thereof.

In certain embodiments, the chiral amino donor molecule is (S)-1-aminoindane. In certain embodiments, the chiral amino donor molecule is (R)-1-aminoindane.

In certain embodiments, the process comprises contacting a compound of formula (I), a chiral amino donor molecule, and an amine transaminase enzyme in a solution to provide a compound of formula (II), or a salt thereof, with the newly-formed amino group having (S) stereochemistry.

In certain embodiments, the process comprises contacting a compound of formula (I), or a salt thereof, a chiral amino donor molecule, and an amine transaminase enzyme in a solution to provide a compound of formula (II), or a salt thereof, with the newly-formed amino group having (R) stereochemistry.

Amine Transaminase (ATA) Enzyme

An amine transaminase (ATA) enzyme catalyzes the transfer of the —NH$_2$ group from the amino donor molecule to a compound having a ketone functional group, e.g., a compound of formula (I), in order to provide a compound of formula (II).

In certain embodiments, the amine transaminase enzyme preferentially generates a compound of formula (II), or a salt thereof, with the newly-formed amino group having (R) or (S) stereochemistry. As used herein, "preferentially generates" refers to the production of one stereoisomer of a compound of formula (II) in excess over the other stereoisomer.

In certain embodiments, the amine transaminase enzyme preferentially generates a compound of formula (II), or a salt thereof, with the newly-formed amino group having (R) stereochemistry.

In certain embodiments, the amine transaminase enzyme preferentially generates a compound of formula (II), or a salt thereof, with the newly-formed amino group having (S) stereochemistry.

In certain embodiments, the amine transaminase enzyme preferentially generates a compound of formula (II), or a salt thereof, with the newly-formed amino group having (R) or (S) stereochemistry, in greater than 40% diastereomeric excess (de), greater than 50% de, greater than 60% de, greater than 70% de, greater than 75% de, greater than 80% de, greater than 85% de, greater than 90% de, greater than 95% de, greater than 98% de, or greater than 99% de, as determined by HPLC.

In certain embodiments, the amine transaminase enzyme preferentially generates an enantiomerically pure compound of formula (II), or salt thereof.

In certain embodiments, the amine transaminase enzyme is an omega amine transaminase enzyme, a broad-range transaminase, a glutamate-pyruvate transaminase or a glutamate-oxaloacetic transaminase.

In certain embodiments, the amine transaminase enzyme is an omega amine transaminase enzyme.

Exemplary omega amine transaminase enzymes include, but are not limited to, omega amine transaminase enzymes from Codexis, Inc. (Redwood City, Calif.), such as ATA-101, ATA-102, ATA-103, ATA-104, ATA-105, ATA-106, ATA-107, ATA-108, ATA-109, ATA-110, ATA-113, ATA-114, ATA-115, ATA-116, ATA-117 and ATA-124; omega amine transaminases from *Vibrio fluvialis, Alcaligenes denitrificans, Klebsiella pneumoniae*, or *Bacillus thuringiensis*, such as is described in WO 2007093372, incorporated herein by reference; omega amine transaminases from *Chromobacterium violaceum*, such as is described in Smithies et al., *Tetrahedron Asymmetry* (2009) 570-574, incorporated herein by reference, omega amine transaminases from *Bacillus cereus*, such as is described in Nakano et al., J. Biochem. (1977) 81:1375-1381, incorporated herein by reference, and omega amine transaminases from *Arthrobactercitreus*, such as described in Cassimjee et al., *ChemComm* (2010) 46:5569-5571, incorporated herein by reference.

Other suitable exemplary omega amine transaminases which may be used according to the present invention are described in Iwa-saki et al., *Biotechnol. Lett.* (2003) 25:1843-1846; Shin et al., *Biotechnol. Bioeng.* (1997) 55:348-358; Shin and Kim, *Biosc. Biotechnol. Biochem.* (2001) 65:1782-1788; Koszelewski et al., *Trends in Biotechnology* (2010) 28:324-332, and Shin and Kim, *Biotechnol. Bioeng.* (1998) 60:534-540, each of which is incorporated herein by reference.

Immobilization of the amine transaminase enzyme can also be effective to improve the stability of the enzyme which in turn will allow its re-use, thereby making the process more economical. Immobilization of the enzymes has been achieved by a simple adsorption onto a hydrophobic resin or by intermolecular covalent cross-linking of enzymes with a variety of functional groups or finally by incorporating enzymes into the lattice of a polymer matrix or a membrane. Covalent immobilization of the omega amine transaminase from *Vibrio fluvialis* JS17 has been reported by Lee and co-workers where the authors adsorb the enzyme on chitosan beads and subsequently cross linked with glutaraldehyde (Yi et al., *Proc. Biochem.* (2007) 42:895-898, incorporated herein by reference). The immobilized amine transaminase enzyme on chitosan beads retained ca. 77% of its activity after five consecutive reactions with the substrate indicating the utility of the process.

In certain embodiments, the omega amine transaminase enzyme is an amine transaminase enzyme from Codexis, Inc.

In certain embodiments, the omega amine transaminase enzyme is ATA-113.

In certain embodiments, the omega amine transaminase enzyme is ATA-117.

In certain embodiments, the omega amine transaminase enzyme is an omega amine transaminase from *Vibrio fluvialis*.

In certain embodiments, the omega amine transaminase enzyme is an omega amine transaminase from *Alcaligenes denitrificans*.

In certain embodiments, the omega amine transaminase enzyme is an omega amine transaminase from *Arthrobactercitreus*.

In certain embodiments, the omega amine transaminase enzyme is an omega amine transaminase from *Klebsiella pneumoniae*.

In certain embodiments, the omega amine transaminase enzyme is an omega amine transaminase from *Bacillus thuringiensis*.

In certain embodiments, the omega amine transaminase enzyme is an omega amine transaminase from *Bacillus cereus*.

In certain embodiments, the omega amine transaminase enzyme is an omega amine transaminase from *Chromobacterium violaceum*.

In certain embodiments, the omega amine transaminase enzyme is an immobilized omega amine transaminase enzyme.

Co-Factors

In certain embodiments, the process further comprises adding a co-factor to the solution. Co-factors include prosthetic groups which are bound to an enzyme during the enzymatic reaction, and co-enzymes which act to transfer chemical groups during the enzymatic reaction.

Exemplary co-factors include the prosthetic group pyridoxal phosphate (PLP) and co-enzymes such as L-alanine dehydrogenase (LADH), lactate dehydrogenase (LDH), nicotinamide adenine dinucleotide phosphate (NADPH), nicotinamide adenine dinucleotide (NAD), formate dehydrogenase (FDH) and glucose dehydrogenase (GDH).

In certain embodiments, the process further comprises adding the co-factor pyridoxal phosphate (PLP) to the solution.

In certain embodiments, the amine transaminase enzyme and the co-factor pyridoxal phosphate added to the solution are pre-complexed before contacting with the compound of formula I. In other embodiments, the amine transaminase (ATA) enzyme and pyridoxal phosphate added to the solution are not pre-complexed before contacting with the compound of formula I (i.e., each is individually added to the solution).

In certain embodiments, the process further comprises adding a co-enzyme to the solution. In certain embodiments, the process further comprises adding one or more co-enzymes selected from L-alanine dehydrogenase (LADH), lactate dehydrogenase (LDH), nicotinamide adenine dinucleotide phosphate (NADPH), nicotinamide adenine dinucleotide (NAD), formate dehydrogenase (FDH), and glucose dehydrogenase (GDH) to the solution.

In certain embodiments, the process further comprises adding the co-enzyme LADH to the solution.

In certain embodiments, the process further comprises adding the co-enzyme FDH to the solution.

In certain embodiments, the process further comprises adding the co-enzyme NAD to the solution.

In certain embodiments, the process further comprises adding the co-enzyme LDH to the solution.

In certain embodiments, the process further comprises adding the co-enzyme GDH to the solution.

In certain embodiments, the process further comprises adding a mixture of LADH, FDH and NAD to the solution.

In certain embodiments, the process further comprises adding a mixture of co-enzymes LDH, GDH and NAD to the solution.

In certain embodiments, the process further comprises adding a sugar to the solution. In certain embodiments, the sugar is glucose.

In certain embodiments, process further comprises adding a pyruvate reductase mix to the solution. In certain embodiments, the process further comprises adding a mixture of co-enzymes LDH, GDH, NAD, and the sugar glucose (e.g., for example, pyruvate reductase mix PRM-102, available from Codexis, Inc.) to the solution.

In certain embodiments, the process further comprises adding ammonia or an ammonium salt to the solution. In certain embodiments, the ammonium salt is ammonium formate ($NH_4CO_2H$). Ammonium formate can be obtained in situ from the combination of formic acid and ammonia.

Other Reaction Conditions

In certain embodiments, the solution comprises an aqueous solution.

In certain embodiments, the aqueous solution is a buffered aqueous solution. Exemplary buffers include, but are not limited to, 3-{[tris(hydroxymethyl)methyl]amino}propanesulfonic acid (TAPS), N,N-bis(2-hydroxyethyl)glycine (Bicine), tris(hydroxymethyl)methylamine (Tris), N-tris(hydroxymethyl)methylglycine (Tricine), 4-2-hydroxyethyl-1-piperazineethanesulfonic acid (HEPES), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), 2-(N-morpholino)ethanesulfonic acid (MES), carbonic acid, phosphate buffered saline (PBS), acetate, sodium phosphate, and salts thereof.

In certain embodiments, the buffered aqueous solution is a sodium phosphate buffered solution.

In certain embodiments, the solution further comprises a co-solvent. In certain embodiments, the co-solvent is an organic solvent.

In certain embodiments, the organic solvent is water miscible. In certain embodiments, the organic solvent is water immicible.

In certain embodiments, the solution is a monophasic system, e.g., comprising an aqueous solution and one or more water miscible organic solvents. Suitable water miscible organic solvents include, but are not limited to, organic alcohols (e.g., methanol (MeOH), ethanol (EtOH), isopropanol (iPrOH) and 2,2,2-trifluoroethanol ($CF_3CH_2OH$)), dimethylsulfoxide (DMSO), dimethylformamide (DMF), glycols (e.g., ethylene glycol and propylene glycol), and mixtures thereof.

In certain embodiments, the solution comprises an aqueous solution and an organic alcohol. In certain embodiments, the solution comprises an aqueous solution and methanol.

However, in other embodiments, the solution is a biphasic system, e.g., comprising an aqueous solution and one or more water immicible organic solvents. Suitable water immicible organic solvents include, but are not limited to, alkanes (e.g., hexane, heptane, perfluorohexane), esters (e.g., ethyl acetate (EtOAc), isopropyl acetate (iPrOAc)), ketones (e.g., cyclohexanone), ethers (e.g., 2-methyl tetrahydrofuran), and aromatic hydrocarbon's (e.g., toluene, xylenes, benzene).

In certain embodiments, the pH of the solution is between about 5 and about 9, between about 5 and about 8, between about 6 and about 8, between about 7 and about 8, between about 7 and about 7.5, or between about 7.5 and about 8.

In certain embodiments, the pH is of the solution is less than about 9, less than about 8.5, or less than about 8. In certain embodiments, the pH of the solution is about 7. In certain embodiments, the pH of the solution is about 7.5. In certain embodiments, the pH of the solution is about 8.

In certain embodiments, the temperature of the solution is at least about 20° C., at least about 25° C., at least about 30° C., or at least about 35° C. In certain embodiments, the temperature of the solution is between about 20° C. and about 50° C.

In certain embodiments, the process further comprises a resin. Adsorption of the ketone starting material (I) or the product amine (II) to the resin reduces their respective concentration in the reaction medium, and thus reduces their propensity to inhibit the enzyme. Exemplary resins include, but are not limited to, Amberlite™, Amberlyst™ and Dowex™ resins.

In certain embodiments, the process further comprises a solubilizer such as a cyclodextrin or a surfactant. Exemplary cyclodextrins include, but are not limited to, β-cyclodextrins and γ-cyclodextrins. Exemplary surfactants include, but are not limited to sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), polyoxyethylene ethers, (e.g. polyoxyethylene lauryl ether [Brij 30]), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, and/or combinations thereof.

In certain embodiments, the process further comprises a sulfate (e.g., for example, sodium bisulfate). For example, when benzylamine is used as the amino donor molecule, sodium bisulfate reacts with the by-product benzaldehyde to form an insoluble bisulfite adduct.

In certain embodiments, the process further comprises a dehydrogenase enzyme (e.g., a yeast alcohol dehydrogenase (YADH) such as from *Saccharomyces cerevisiae*). For example, when isopropyl amine is used as the amino donor molecule, a YADH enzyme converts the acetone by-product to isopropanol, thereby shifting the equilibrium and driving the reaction to completion (see Cassimjee et al., *Chem Comm* (2010) 46:5569-5571, incorporated herein by reference).

Additional Embodiments

In certain embodiments, provided is a process for preparing a compound of formula (R)-(II-a):

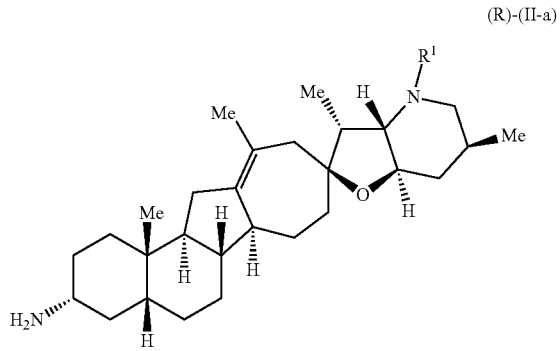

(R)-(II-a)

or a salt thereof;

from a compound of formula (I-a):

(I-a)

or a salt thereof;
wherein:
$R^1$ is H, aralkyl, or $-CO_2R^{16}$;
$R^{16}$ is H, alkyl, alkenyl, alkynyl, aryl, cycloalkyl, heterocycloalkyl, aralkyl, heteroaryl, heteroaralkyl or $-[C(R^{20})_2]_p-R^{21}$ wherein p is 0-6;
$R^{20}$ is H, alkyl, alkenyl, alkynyl, aryl, cycloalkyl, heterocycloalkyl, aralkyl, heteroaryl, or heteroaralkyl; or any two occurrences of $R^{20}$ on the same substituent are taken together to form a 4-8 membered optionally substituted ring;
$R^{21}$ is $-OR^{22}$, $-N(R^{22})C(=O)R^{22}$, $-N(R^{22})C(=O)OR^{22}$, $-N(R^{22})SO_2(R^{22})$, $-C(=O)R^{22}N(R^{22})_2$, $-OC(=O)R^{22}N(R^{22})(R^{22})$, $-SO_2N(R^{22})(R^{22})$, $-N(R^{22})(R^{22})$, $-C(=O)OR^{22}$, $-C(=O)N(OH)(R^{22})$, $-OS(O)_2OR^{22}$, $-S(O)_2OR^{22}$, $-OP(=O)(OR^{22})(OR^{22})$, $-N(R^{22})P(O)(OR^{22})(OR^{22})$, or $-P(=O)(OR^{22})(OR^{22})$; and
$R^{22}$ is H, alkyl, alkenyl, alkynyl, aryl, cycloalkyl, heterocycloalkyl, aralkyl, heteroaryl, heteroaralkyl; or any two occurrences of $R^{22}$ on the same substituent are taken together to form a 4-8 membered optionally substituted ring;
the process comprising contacting a compound of formula (I-a) or a salt thereof, an amino donor molecule, and an amine transaminase enzyme in a solution to provide a compound of formula (R)-(II-a) or a salt thereof.

In certain embodiments, $R^1$ is H, aralkyl, or $-CO_2R^{16}$.
In certain embodiments, $R^1$ is H.
In certain embodiments, $R^1$ is aralkyl.
In certain embodiments, $R^1$ is $-CO_2R^{16}$. In certain embodiments, $R^1$ is $-CO_2R^{16}$ and $R^{16}$ is alkyl, alkenyl, alkynyl, aryl, cycloalkyl, heterocycloalkyl, aralkyl, heteroaryl or heteroaralkyl. In certain embodiments, $R^1$ is a -Boc group (e.g., wherein $R^1$ is $-CO_2R^{16}$ and $R^{16}$ is t-butyl). In certain embodiments, $R^1$ is a -CBz group (e.g., wherein $R^1$ is $-CO_2R^{16}$ and $R^{16}$ is benzyl).

In certain embodiments, the amino donor molecule is a chiral amino donor molecule. In certain embodiments, the chiral amino donor molecule is (R)-methylbenzylamine or a salt thereof. In other embodiments, the chiral amino donor molecule is (S)-methylbenzylamine or a salt thereof.

In certain embodiments, the chiral amino donor molecule is (L)-alanine or a salt thereof. In certain embodiments, the chiral amino donor molecule is (D)-alanine or a salt thereof.

In certain embodiments, the amine transaminase enzyme is an omega amine transaminase enzyme. In certain embodiments, the omega amine transaminase enzyme is ATA-113 from Codexis, Inc. In certain embodiments, the omega amine transaminase enzyme is ATA-117 from Codexis, Inc. In certain embodiments, the omega amine transaminase enzyme is an omega amine transaminase from *Vibrio fluvialis*.

Additional Steps

In certain embodiments, the process further comprises contacting a compound of formula (II):

(II)

or a salt thereof,
wherein $R^1$, $R^2$, $R^3$, $R^4$, $R^5$, $R^6$, $R^7$, $R^8$, $R^9R^{10}$, $R^{11}$, $R^{12}$, $R^{13}$, $R^{14}$, $R^{15}$ and X are as defined herein,
with a sulfonylating agent to provide a compound of formula (III):

(III)

or a salt thereof,
wherein $R^1$, $R^2$, $R^3$, $R^4$, $R^5$, $R^6$, $R^7$, $R^8$, $R^9$, $R^{19}$, $R^{11}$, $R^{12}$, $R^{13}$, $R^{14}$, $R^{15}$ and X are as defined herein, and
$R^{23}$ is alkyl or aryl.

Exemplary sulfonylating agents include, but are not limited to, benzenesulfonyl chloride, benzenesulfonyl anhydride, p-toluenesulfonyl chloride, p-toluenesulfonyl anhydride, methanesulfonyl chloride, and methanesulfonyl anhydride.

In certain embodiments, the sulfonylating agent is benzenesulfonyl chloride or benzenesulfonyl anhydride, and $R^{23}$ is benzenyl (i.e., $-C_6H_5$).

In certain embodiments, the sulfonylating agent is p-toluenesulfonyl chloride or p-toluenesulfonyl anhydride, and $R^{23}$ is toluenyl (i.e., $-C_6H_4(p-CH_3)$).

In certain embodiments, the sulfonylating agent is methanesulfonyl chloride or methanesulfonyl anhydride, and $R^{23}$ is methyl (i.e., $-CH_3$).

In certain embodiments, the compound of formula (II) is:

(II-a)

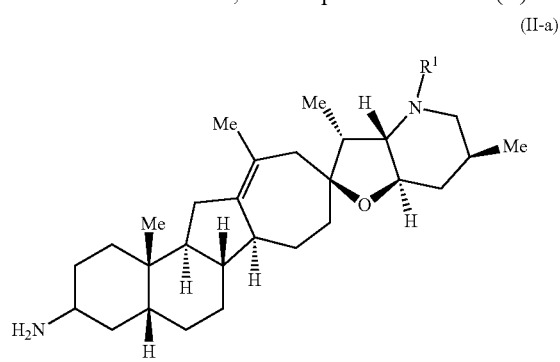

or a salt thereof,
and the compound of formula (III) is:

(III-a)

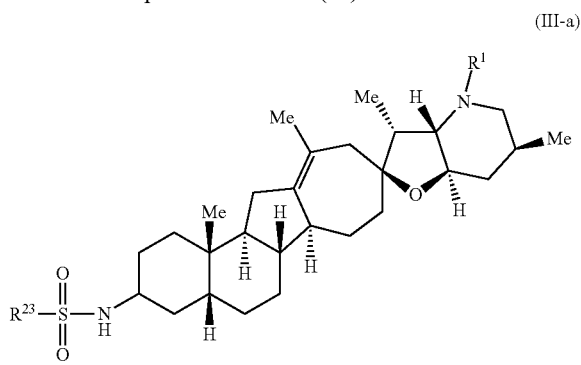

or a salt thereof,
wherein $R^1$ and $R^{23}$ are as defined herein.
In certain embodiments, the compound of formula (II) is:

(R)-(II-a)

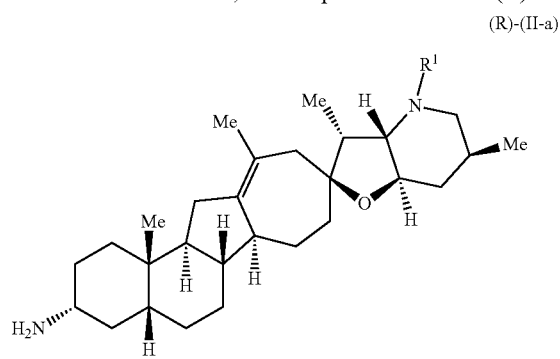

or a salt thereof,
and the compound of formula (III) is:

(R)-(III-a)

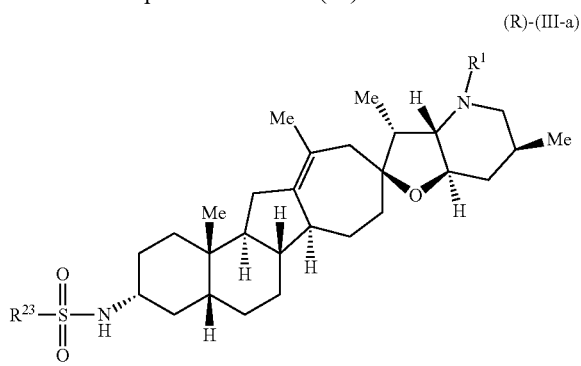

or a salt thereof,
wherein $R^1$ and $R^{23}$ are as defined herein.
In certain embodiments, $R^1$ is H.
In certain embodiments, $R^1$ is aralkyl.
In certain embodiments, $R^1$ is $-CO_2R^{16}$.

In certain embodiments wherein $R^1$ is aralkyl or $-CO_2R^{16}$, the process further comprises deprotecting the compound of formula (III) wherein $R^1$ is aralkyl or $-CO_2R^{16}$ to provide a compound of formula (III) wherein $R^1$ is H. Exemplary deprotection methods include, but are not limited to, reducing conditions, such as hydrogenation.

For example, in certain embodiments, the process further comprises deprotecting the compound of formula (R)-(III-a):

(R)-(III-a)

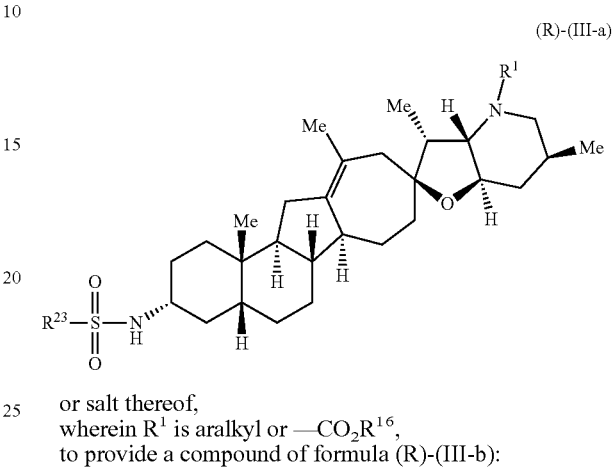

or salt thereof,
wherein $R^1$ is aralkyl or $-CO_2R^{16}$,
to provide a compound of formula (R)-(III-b):

(R)-(III-b)

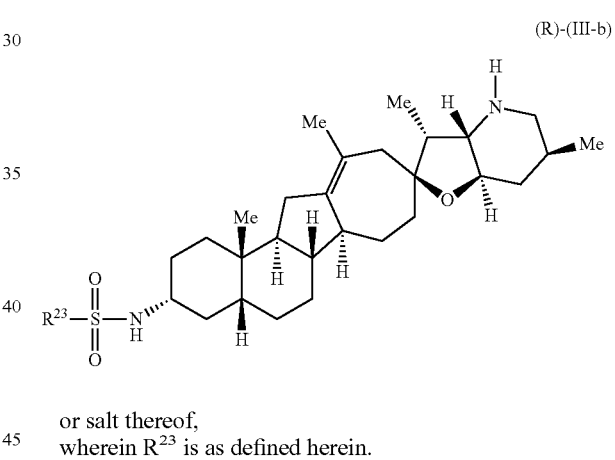

or salt thereof,
wherein $R^{23}$ is as defined herein.

EXEMPLIFICATION

The present disclosure now being generally described, it will be more readily understood by reference to the following examples, which are included merely for purposes of illustration and are not intended to limit the disclosure herein.

Enzymatic Transamination of Compound (I-a)

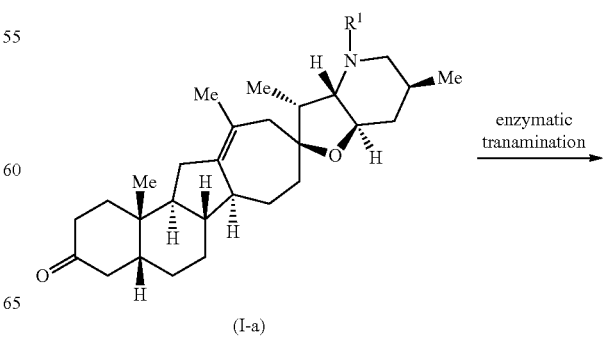

(I-a)

(R)-(II-a)

and/or (S)-(II-a)

Materials and Methods

Enzymes.

Amine transaminase enzymes were purchased from commercially available sources, stored at −20° C., and used as received: ATA-113 (Codexis, Redwood City, Calif.; Lot no. 104020902); ATA-117 (Codexis, Redwood City, Calif.; Lot no. 104020902); omega-transaminase from *Vibrio fluvialis* (Fluka; cat, no 08374); glutamate pyruvate transaminase (Fluka); broad range transaminase (Fluka).

Co-Enzymes.

Co-enzymes utilized during the investigation include: L-alanine dehydrogenase (LADH, Sigma, no. A7653-100U), formate dehydrogenase (FDH, Codexis, FDH-101) and pyruvate reductase mix (PRM-102, Codexis), which is a mixture lactate dehydrogenase (LDH), glucose dehydrogenase (GDH), glucose and $NAD^+$.

pH.

The following buffers were used during the investigation: 100 mM sodium phosphate buffer (pH 7; Fluka no. 82637); 20 mM sodium phosphate buffer (pH 7.5; Fluka, no. 82592); 20 mM sodium phosphate buffer (pH 8; Fluka, no. 82593).

HPLC Method 1.

Symmetry C18 column 4.6×150 mm; flow rate 1.5 mL/min; mobile phase A=0.1% TFA in water; mobile phase B=0.1% TFA in acetonitrile; 10 µL injection; 40° C. column temperature; detection wavelength=215 nm (all species). Retention time of compound (II-a) ($R^1$=H: S-(II-a)=5.9 min; R-(II-a), =6.8 min).

HPLC Method 1 Gradient:

| Time (minutes) | % mobile phase A | % mobile phase B |
|---|---|---|
| 0 | 90 | 10 |
| 1.0 | 90 | 10 |
| 10.0 | 40 | 60 |
| 11.0 | 5 | 95 |
| 12.0 | 5 | 95 |
| 13.0 | 90 | 10 |
| 15.0 | 90 | 10 |

HPLC Method 2.

XBridge C8 column 4.6×75 mm; flow rate 1.0 mL/min; mobile phase A=10 mM ammonium formate buffer, pH 3.8; mobile phase B=0.05% formic acid in acetonitrile; 5 µL injection; 40° C. column temperature; detection wavelength=215 nm (all species), Retention time of compound (II-a) ($R^1$=Bn: S-(II-a)=7.0 min; R-(II-a)=7.5 min).

HPLC Method 2 Gradient:

| Time (minutes) | % mobile phase A | % mobile phase B |
|---|---|---|
| 0 | 80 | 20 |
| 2 | 80 | 20 |
| 16 | 5 | 95 |
| 18 | 5 | 95 |
| 18.1 | 80 | 20 |
| 20 | 80 | 20 |

HPLC Method 3.

Eclipse XDB-C8 column 4.6×50 mm; flow rate 1.5 mL/min; mobile phase A=0.1% TFA in water; mobile phase B=0.1% TFA in acetonitrile; 10 µL injection; 40° C. column temperature; detection wavelength=215 nm (all species). Retention time of compound (II-a) ($R^1$=Cbz: S-(II-a)=6.0 min; R-(II-a)=6.1 min).

HPLC Method 3 Gradient:

| Time (minutes) | % mobile phase A | % mobile phase B |
|---|---|---|
| 0 | 70 | 30 |
| 2.0 | 70 | 30 |
| 8.0 | 0 | 100 |
| 10.0 | 0 | 100 |
| 12.0 | 70 | 30 |
| 15.0 | 70 | 30 |

General Experimental Methods

Method A:

Compound (I-a), a sodium phosphate buffered solution, 1 mM pyridoxal phosphate (PLP), an amine transaminase enzyme, an amino donor molecule, PRM-102 and, optionally, a co-solvent, were added to a vial. The vial was capped and the reaction stirred at 30° C. for 72 hours. The reaction mixture was then lyophilized and the residue was re-dissolved in methanol (2 mL). A 100 µL portion of the methanol solution was filtered and analyzed by HPLC. The results of Experiments 1-8 using Method A are summarized in Table 6.

Method B:

Compound (I-a), a sodium phosphate buffered solution, 1 mM pyridoxal phosphate (PLP), amine transaminase enzyme, D-alanine, ammonium formate ($NH_4CO_2H$), L-alanine dehydrogenase (LADH) solution (8.05 U/mL), formate dehydrogenase (FDH) solution (10 U/mL), NAD (1 mM) and a co-solvent were added to a vial. The vial was capped and the reaction stirred at 30° C. for 72 hours. The reaction mixture was then lyophilized and the residue was re-dissolved in methanol (2 mL). A 100 µL portion of the methanol solution was filtered and analyzed by HPLC. The results of Experiments 1-10 using Method B are summarized in Table 7.

Method C:

Compound (I-a), a sodium phosphate buffered solution, pyridoxal phosphate (PLP) (0.5 mM to 1 mM), an amine transaminase enzyme, an amino donor molecule, and, optionally, a co-solvent and PRM-102, were added to a vial. The vial was capped and the reaction stirred at 37° C. for 24 hours to about 6 days (144 hours). The reaction mixture was then lyophilized and the residue was re-dissolved in methanol (2 mL). A 100 μL portion of the methanol solution was filtered and analyzed by HPLC. The results of Experiments 1-28 using Method C are summarized in Table 8.

Method D:

Compound (I-a), a sodium phosphate buffered solution, pyridoxal phosphate (PLP) (0.5 mM), an amine transaminase enzyme, an amino donor molecule (5 equivalents), PRM-102, and, optionally, a co-solvent, were added to a vial. The vial was capped and the reaction stirred at 37° C. for 24 hours to about 7 days (168 hours). A 100 μL portion of the reaction mixture was diluted with 1 volume of MeOH and analyzed by HPLC. The results of Experiments 1-13 using Method D are summarized in Table 9.

Method E:

Compound (I-a), a sodium phosphate buffered solution, pyridoxal phosphate (PLP) (0.5 mM), an amine transaminase enzyme, L-alanine (5 equivalents), PRM-102, and methanol (10% v/v) were added to a vial. The vial was capped and the reaction stirred at 37° C. for 24 hours to about 7 days (168 hours). A 100 μL portion of the reaction mixture was diluted with 1 volume of MeOH and analyzed by HPLC. The results of Experiments 1-5 using Method E are summarized in Table 10.

Method F:

Compound (I-a), a sodium phosphate buffered solution (pH=7.5), pyridoxal phosphate (PLP) (0.5 mM), an amine transaminase enzyme, L-alanine (5 equivalents), PRM-102, and methanol (10% v/v) were added to a vial. The vial was capped and the reaction stirred at 37° C. for 24 hours to about 7 days (168 hours). The pH of the aqueous layer was monitored at the onset and during the course of the reaction and if necessary, it was readjusted to 7.5 using 0.1 M NaOH solution. A 100 μL portion of the reaction mixture was diluted with 1 volume of MeOH and analyzed by HPLC. The results of Experiments 1-9 using Method F are summarized in Table 11.

Method G:

Compound (I-a), a sodium phosphate buffered solution (pH=7.5), pyridoxal phosphate (PLP) (0.5 mM), an amine transaminase enzyme, L-alanine (5 equivalents), PRM-102, an additive (100% wt/wt) and methanol (10% v/v) were added to a vial. The vial was capped and the reaction stirred at 37° C. for 24 hours to about 7 days (168 hours). A 100 μL portion of the reaction mixture was diluted with 1 volume of MeOH and analyzed by HPLC. The results of Experiments 1-5 using Method G are summarized in Table 12.

Method H:

Compound (I-a), a sodium phosphate buffered solution (pH=7.5), pyridoxal phosphate (PLP) (0.5 mM), an amine transaminase enzyme, L-alanine (5 equivalents), PRM-102, a co-solvent (10 to 20% v/v) were added to a vial. The vial was capped and the reaction stirred at 37° C. for 24 hours to about 7 days (168 hours). A 100 μL portion of the reaction mixture was diluted with 1 volume of MeOH and analyzed by HPLC. The results of Experiments 1-12 using Method H are summarized in Table 13.

TABLE 6

Method A

| | (I-a) | Buffer | pH | Co-solvent | PLP (mM) | Enzyme | Amine donor | PRM-102 (mg) | Time (hrs) | 2 | % Conversion |
|---|---|---|---|---|---|---|---|---|---|---|---|
| 1 | 6.5 mg ($R^1$ = H, citrate salt) | 100 mM (0.85 mL) | 7 | MeOH (0.15 mL) | 1 | ATA-117 (3 mg) | D-alanine (4.5 mg) | 39 | 72 | (S) | 3% |
| 2 | 6.5 mg ($R^1$ = H, citrate salt) | 100 mM (0.85 mL) | 7 | $CF_3CH_2OH$ (0.15 mL) | 1 | ATA-117 (3 mg) | D-alanine (4.5 mg) | 39 | 72 | — | n/a |
| 3 | 20 mg ($R^1$ = H, citrate salt) | 100 mM (2 mL) | 7 | none | 1 | ATA-117 (3 mg) | D-alanine (9.5 mg) | 60 | 72 | (S) | 3% |
| 4 | 20 mg ($R^1$ = H, citrate salt) | 100 mM (1.8 mL) | 7 | MeOH (0.2 mL) | 1 | ATA-117 (10 mg) | D-alanine (11 mg) | 60 | 72 | (S) | 2% |
| 5 | 20 mg ($R^1$ = H, citrate salt) | 100 mM (1.8 mL) | 7 | MeOH (0.2 mL) | 1 | broad-range transaminase (1.7 mg) | D-alanine (11 mg) | 60 | 72 | — | n/a |
| 6 | 20 mg ($R^1$ = H, citrate salt) | 100 mM (1.8 mL) | 7 | MeOH (0.2 mL) | 1 | glutamate pyruvate transaminase (1 mg) | D-alanine (11 mg) | 60 | 72 | — | n/a |
| 7 | 20 mg ($R^1$ = H, citrate salt) | 100 mM (2 mL) | 7 | none | 1 | ATA-113 (10 mg) | L-alanine (9.5 mg) | 60 | 72 | (S) | 15% |
| 8 | 20 mg ($R^1$ = H, citrate salt) | 100 mM (1.8 mL) | 7 | MeOH (0.2 mL) | 1 | ATA-113 (10 mg) | L-alanine (11 mg) | 60 | 72 | (S) | 5% |

TABLE 7

Method B

| | (I-a) | Buffer | pH | co-solvent | PLP (mM) | enzyme | donor | $NH_4CO_2H$ (mg) | FDH (μL) | LADH (μL) | NAD (mM) | 2 | % |
|---|---|---|---|---|---|---|---|---|---|---|---|---|---|
| 1 | 3.5 mg ($R^1$ = H, citrate salt) | 100 mM (0.85 mL) | 7 | DMSO (0.15 mL) | 1 | ATA-117 (3 mg) | D-alanine (9.5 mg) | 4 | 25 | 10 | 1 | — | n/a |

TABLE 7-continued

Method B

| (I-a) | Buffer | pH | co-solvent | PLP (mM) | enzyme | donor | NH₄CO₂H (mg) | FDH (μL) | LADH (μL) | NAD (mM) | 2 | % |
|---|---|---|---|---|---|---|---|---|---|---|---|---|
| 2 | 3.5 mg (R¹ = H, citrate salt) | 100 mM (0.85 mL) | 7 | MeOH (0.15 mL) | 1 | ATA-117 (3 mg) | D-alanine (9.5 mg) | 4 | 25 | 10 | 1 | (S) | 1% |
| 3 | 3.5 mg (R¹ = H, citrate salt) | 20 mM (0.85 mL) | 7.5 | DMSO (0.15 mL) | 1 | ATA-117 (3 mg) | D-alanine (9.5 mg) | 4 | 25 | 10 | 1 | — | n/a |
| 4 | 3.5 mg (R¹ = H, citrate salt) | 20 mM (0.85 mL) | 7.5 | MeOH (0.15 mL) | 1 | ATA-117 (3 mg) | D-alanine (9.5 mg) | 4 | 25 | 10 | 1 | — | n/a |
| 5 | 6.5 mg (R¹ = H, citrate salt) | 100 mM (0.85 mL) | 7 | CF₃CH₂OH (0.15 mL) | 1 | ATA-117 (3 mg) | D-alanine (13 mg) | 6 | 50 | 20 | 1 | — | n/a |
| 6 | 6.5 mg (R¹ = H, citrate salt) | 100 mM (0.85 mL) | 7 | MeOH (0.15 mL) | 1 | ATA-117 (3 mg) | D-alanine (22 mg) | 9 | 50 | 20 | 1 | (S) | 5% |
| 7 | 3.5 mg (R¹ = H, citrate salt) | 100 mM (0.85 mL) | 7 | MeOH (0.15 mL) | 1 | ATA-113 (1.3 mg) | D-alanine (9.5 mg) | 4 | 22 | 8.8 | 1 | (S) | 8% |
| 8 | 3.5 mg (R¹ = H, citrate salt) | 100 mM (0.85 mL) | 7 | DMSO (0.15 mL) | 1 | ATA-113 (1.3 mg) | D-alanine (9.5 mg) | 4 | 22 | 8.8 | 1 | (S) | 37% |
| 9 | 10 mg (R¹ = H, citrate salt) | 100 mM (8.5 mL) | 7 | DMSO (1.5 mL) | 1 | ATA-113 (13 mg) | D-alanine (95 mg) | 40 | 216 | 86 | 1 | (S) | 12% |
| 10 | 3.5 mg (R¹ = H, citrate salt) | 100 mM (0.85 mL) | 7 | DMSO (1.3 mL); Et₂O (0.2 mL) | 1 | ATA-113 (1.3 mg) | D-alanine (12 mg) | 5 | 22 | 8.8 | 1 | (S) | 10% |

TABLE 8

Method C

| (I-a) | Buffer | pH | Co-solvent | PLP (mM) | Enzyme | Amine donor | PRM-102 (mg) | Time (hrs) | 2 | % Conversion |
|---|---|---|---|---|---|---|---|---|---|---|
| 1 | 15 mg (R¹ = H) | 100 mM (1.8 mL) | 7 | MeOH (0.2 mL) | 1 | ATA-117 (10 mg) | D-alanine (13 mg) | 60 | 24 | (S) | 2% |
| 2 | 15 mg (R¹ = H) | 100 mM (1.8 mL) | 7 | MeOH (0.2 mL) | 1 | ATA-113 (10 mg) | L-alanine (13 mg) | 60 | 24 | (S) | 10% |
| 3 | 1 mg (R¹ = H) | 20 mM (1.2 mL) | 7.5 | MeOH (0.12 mL) | 0.5 | ATA-113 (2 mg) | (S)-methyl benzyl amine (1.4 μL) | none | 72 | (S) | 9% |
| 4 | 1 mg (R¹ = H) | 20 mM (1.2 mL) | 7.5 | MeOH (0.12 mL) | 0.5 | ATA-113 (2 mg) | (S)-methyl benzyl amine (1.4 μL) | 30 | 72 | (S) | 41% |
| 5 | 8.5 mg (R¹ = H) | 20 mM (10 mL) | 7.5 | MeOH (1 mL) | 1 | ATA-113 (20 mg) | (S)-methyl benzyl amine (13 μL) | 300 | 72 | (S) | 42% |
| 6 | 1 mg (R¹ = H) | 20 mM (1.2 mL) | 7.5 | MeOH (0.12 mL) | 0.5 | ATA-117 (2 mg) | (S)-methyl benzyl amine (1.4 μL) | none | 72 | — | n/a |
| 7 | 1 mg (R¹ = H) | 20 mM (1.2 mL) | 7.5 | MeOH (0.12 mL) | 0.5 | ATA-117 (2 mg) | (S)-methyl benzyl amine (1.4 μL) | 30 | 72 | — | n/a |
| 8 | 1 mg (R¹ = H) | 20 mM (1.2 mL) | 7.5 | MeOH (0.12 mL) | 0.5 | ATA-117 (4 mg) | (S)-methyl benzyl amine (1.4 μL) | 60 | 72 | — | n/a |
| 9 | 8.5 mg (R¹ = H) | 20 mM (10 mL) | 7.5 | MeOH (1 mL) | 0.5 | ATA-117 (10 mg) | (S)-methyl benzyl amine (13 μL) | 150 | 72 | — | n/a |
| 10 | 8.5 mg (R¹ = H) | 20 mM (9 mL) | 8 | MeOH (1 mL) | 0.5 | ATA-117 (20 mg) | (S)-methyl benzyl amine (13 μL) | 300 | 72 | — | n/a |
| 11 | 6.4 mg (R¹ = H) | 20 mM (9 mL) | 8 | MeOH (1 mL) | 0.5 | ATA-117 (20 mg) | (S)-methyl benzyl amine (13 μL) | 300 | 72 | — | n/a |
| 12 | 4.3 mg (R¹ = H) | 20 mM (9 mL) | 8 | MeOH (1 mL) | 0.5 | ATA-117 (20 mg) | (S)-methyl benzyl amine (13 μL) | 300 | 72 | — | n/a |

TABLE 8-continued

Method C

| (I-a) | Buffer | pH | Co-solvent | PLP (mM) | Enzyme | Amine donor | PRM-102 (mg) | Time (hrs) | 2 | % Conversion |
|---|---|---|---|---|---|---|---|---|---|---|
| 13 | 2.1 mg (R¹ = H) | 20 mM (9 mL) | 8 | MeOH (1 mL) | 0.5 | ATA-117 (20 mg) | (S)-methyl benzyl amine (13 µL) | 300 | 72 | — | n/a |
| 14 | 1.6 mg (R¹ = H) | 20 mM (1.2 mL) | 7.5 | none | 1 | Vibrio fluvialis (55 µL) | (S)-methyl benzyl amine (13 µL) | none | 72 | (R) | 2% |
| 15 | 1 mg (R¹ = H) | 20 mM (1.2 mL) | 7.5 | MeOH (0.12 mL) | 0.5 | Vibrio Fluvialis (100 µL) | (R)-methyl benzyl amine (1.4 µL) | none | 72 | (R) | 10% |
| 16 | 4.3 mg (R¹ = H) | 20 mM (4.95 mL) | 7.5 | MeOH (0.55 mL) | 0.5 | Vibrio Fluvialis (155 µL) | (R)-methyl benzyl amine (6.5 µL) | 140 | 72 | (R) | 15% |
| 17 | 1.6 mg (R¹ = H) | 20 mM (2 mL) | 7.5 | none | 0.5 | Vibrio Fluvialis (100 µL) | (S)-methyl benzyl amine (1.4 µL) | none | 72 | (R) | 3% |
| 18 | 8.5 mg (R¹ = H) | 20 mM (10 mL) | 7.5 | MeOH (1 mL) | 0.5 | Vibrio Fluvialis (100 µL) | (R)-methyl benzyl amine (13 µL) | none | 72 | (R) | 10% |
| 19 | 8.5 mg (R¹ = H) | 20 mM (10 mL) | 7.5 | MeOH (1 mL) | 0.5 | Vibrio Fluvialis (310 µL) | (S)-methyl benzyl amine (13 µL) | none | 72 | (R) | 10% |
| 20 | 8.5 mg (R¹ = H) | 20 mM (10 mL) | 7.5 | MeOH (1 mL) | 0.5 | Vibrio Fluvialis (310 µL) | (S)-methyl benzyl amine (13 µL) | 275 | 72 | (R) | 10% |
| 21 | 14 mg (R¹ = H, citrate salt) | 20 mM (10 mL) | 7.5 | MeOH (1 mL) | 0.5 | Vibrio Fluvialis (310 µL) | (R)-methyl benzyl amine (13 µL) | 300 | 72 | (R) | 17% |
| 22 | 7 mg (R¹ = H, citrate salt) | 20 mM (5 mL) | 7.5 | MeOH (0.5 mL) | 0.5 | Vibrio Fluvialis (155 µL) | (R)-methyl benzyl amine (7 µL) | 150 | 144 | (R) | 28% |
| 23 | 5.5 mg (R¹ = Bn) | 20 mM (5 mL) | 7.5 | EtOAc (0.5 mL) | 1 | Vibrio Fluvialis (150 µL) | (R)-methyl benzyl amine (7 µL) | 150 | 72 | — | n/a |
| 24 | 5.5 mg (R¹ = Bn) | 20 mM (5 mL) | 7.5 | cyclohexanone (0.5 mL) | 1 | Vibrio Fluvialis (150 µL) | (R)-methyl benzyl amine (7 µL) | 150 | 72 | — | n/a |
| 25 | 8.5 mg (R¹ = Bn) | 20 mM (10 mL) | 7 | MeOH (1 mL) | 0.5 | ATA-113 (20 mg) | (S)-methyl benzyl amine (13 µL) | 300 | 72 | (S) | 1.7% |
| 26 | 8.5 mg (R¹ = CBz) | 20 mM (10 mL) | 7 | MeOH (1 mL) | 0.5 | ATA-113 (20 mg) | (S)-methyl benzyl amine (13 µL) | 300 | 72 | (S) | 2% |
| 27 | 8.5 mg (R¹ = Bn) | 20 mM (10 mL) | 7 | MeOH (1 mL) | 0.5 | ATA-117 (20 mg) | (S)-methyl benzyl amine (13 µL) | 300 | 72 | — | n/a |
| 28 | 8.5 mg (R¹ = Cbz) | 20 mM (10 mL) | 7 | MeOH (1 mL) | 0.5 | ATA-117 (20 mg) | (S)-methyl benzyl amine (13 µL) | 300 | 72 | — | n/a |

TABLE 9

Method D

| (I-a) | Buffer | pH | Co-solvent | PLP (mM) | Enzyme | Amine Donor (5 equiv.) | PRM-102 (mg) | Time (hrs) | 2 | % Conversion |
|---|---|---|---|---|---|---|---|---|---|---|
| 1 | 14 mg (R¹ = H, citrate salt) | 20 mM (9 mL) | 7.0 | MeOH (1.0 mL) | 0.5 | Vibrio Fluvialis (310 µL) | L-alanine | 300 mg | 168 | (R) | 16.1% |
| 2 | 14 mg (R¹ = H, citrate salt) | 20 mM (9 mL) | 7.0 | MeOH (1.0 mL) | 0.5 | Vibrio Fluvialis (310 µL) | D-alanine | 300 mg | 168 | (R) | 12.7% |
| 3 | 14 mg (R¹ = H, citrate salt) | 20 mM (9 mL) | 7.0 | MeOH (1.0 mL) | 0.5 | Vibrio Fluvialis (310 µL) | R-Methylbenzylamine | 300 mg | 168 | (R) | 14.1% |
| 4 | 14 mg (R¹ = H, citrate salt) | 20 mM (9 mL) | 7.0 | MeOH (1.0 mL) | 0.5 | Vibrio Fluvialis (310 µL) | S-Methyl benzylamine | 300 mg | 168 | (R) | 7.6% |
| 5 | 14 mg (R¹ = H, citrate salt) | 20 mM (9 mL) | 7.0 | MeOH (1.0 mL) | 0.5 | Vibrio Fluvialis (310 µL) | 2-aminoindane | 300 mg | 168 | (R) | 4.1% |

TABLE 9-continued

Method D

| | (I-a) | Buffer | pH | Co-solvent | PLP (mM) | Enzyme | Amine Donor (5 equiv.) | PRM-102 (mg) | Time (hrs) | 2 | % Conversion |
|---|---|---|---|---|---|---|---|---|---|---|---|
| 6 | 14 mg (R¹ = H, citrate salt) | 20 mM (9 mL) | 7.0 | MeOH (1.0 mL) | 0.5 | Vibrio Fluvialis (310 μL) | S-1-Aminoindane | 300 mg | 168 | — | n/a |
| 7 | 14 mg (R¹ = H, citrate salt) | 20 mM (9 mL) | 7.0 | MeOH (1.0 mL) | 0.5 | Vibrio Fluvialis (310 μL) | R-1-Aminoindane | 300 mg | 168 | (R) | 5.1% |
| 8 | 14 mg (R¹ = H, citrate salt) | 20 mM (9 mL) | 7.0 | MeOH (1.0 mL) | 0.5 | Vibrio Fluvialis (310 μL) | R-2-Amino-1-propanol | 300 mg | 168 | (R) | 3.8% |
| 9 | 14 mg (R¹ = H, citrate salt) | 20 mM (9 mL) | 7.0 | MeOH (1.0 mL) | 0.5 | Vibrio Fluvialis (310 μL) | S-2-Amino-1-propanol | 300 mg | 168 | (R) | 4.6% |
| 10 | 14 mg (R¹ = H, citrate salt) | 20 mM (9 mL) | 7.0 | MeOH (1.0 mL) | 0.5 | Vibrio Fluvialis (310 μL) | (1R,2S)-cis-1-Amino-2-indanol | 300 mg | 168 | — | n/a |
| 11 | 14 mg (R¹ = H, citrate salt) | 20 mM (9 mL) | 7.0 | MeOH (1.0 mL) | 0.5 | Vibrio Fluvialis (310 μL) | (1R,2R)-trans-1-Amino-2-indanol | 300 mg | 168 | — | n/a |
| 12 | 14 mg (R¹ = H, citrate salt) | 20 mM (9 mL) | 7.0 | MeOH (1.0 mL) | 0.5 | Vibrio Fluvialis (310 μL) | 1-R-Amino-6-hydroxyindanamine | 300 mg | 168 | — | n/a |
| 13 | 14 mg (R¹ = H, citrate salt) | 20 mM (9 mL) | 7.0 | MeOH (1.0 mL) | 0.5 | Vibrio Fluvialis (310 μL) | Isopropylamine | 300 mg | 168 | (R) | 8.4% |

TABLE 10

Method E

| | (I-a) | Buffer | pH | Co-solvent | PLP (mM) | Enzyme | Amine donor | PRM-102 (mg) | Time (hrs) | 2 | % Conversion |
|---|---|---|---|---|---|---|---|---|---|---|---|
| 1 | 14 mg (R¹ = H, citrate salt) | 20 mM (9 mL) | 7.0 | MeOH (1.0 mL) | 0.5 | Vibrio Fluvialis (155 μL) | L-alanine (10 mg) | 300 mg | 168 | (R) | 6.4% |
| 2 | 14 mg (R¹ = H, citrate salt) | 20 mM (9 mL) | 8.0 | MeOH (1.0 mL) | 0.5 | Vibrio Fluvialis (155 μL) | L-alanine (10 mg) | 300 mg | 168 | (R) | 14.9% |
| 3 | 14 mg (R¹ = H, citrate salt) | 20 mM (9 mL) | 9.0 | MeOH (1.0 mL) | 0.5 | Vibrio Fluvialis (155 μL) | L-alanine (10 mg) | 300 mg | 168 | (R) | 10.2% |
| 4 | 14 mg (R¹ = H, citrate salt) | 100 mM (9 mL) | 8.1 | MeOH (1.0 mL) | 0.5 | Vibrio Fluvialis (155 μL) | L-alanine (10 mg) | 300 mg | 168 | (R) | 3.6% |
| 5 | 14 mg (R¹ = H, citrate salt) | 100 mM (9 mL) | 7.1 | MeOH (1.0 mL) | 0.5 | Vibrio Fluvialis (155 μL) | L-alanine (10 mg) | 300 mg | 168 | (R) | 7.9% |

TABLE 11

Method F

| | (I-a) | Buffer | pH | Co-solvent | PLP (mM) | Enzyme | Amine donor | PRM-102 (mg) | Time (hrs) | 2 | % Conversion |
|---|---|---|---|---|---|---|---|---|---|---|---|
| 1 | 14 mg (R¹ = H, citrate salt) | 20 mM (9 mL) | 7.5 | MeOH (1.0 mL) | 0.5 | Vibrio Fluvialis (155 μL) | D-alanine (10 mg) | 300 mg | 168 | (R) | 12.7% |
| 2 | 14 mg (R¹ = H, citrate salt) | 20 mM (9 mL) | 7.5 | MeOH (1.0 mL) | none | Vibrio Fluvialis (155 μL) | D-alanine (10 mg) | 300 mg | 168 | — | n/a |
| 3 | 14 mg (R¹ = H, citrate salt) | 20 mM (9 mL) | 7.5 | MeOH (1.0 mL) | 0.5 | Vibrio Fluvialis (155 μL) | L-alanine (10 mg) | 300 mg | 168 | (R) | 16.1% |
| 4 | 14 mg (R¹ = H, citrate salt) | 20 mM (9 mL) | 7.5 | MeOH (1.0 mL) | none | Vibrio Fluvialis (155 μL) | L-alanine (10 mg) | 300 mg | 168 | — | n/a |

TABLE 11-continued

Method F

| | (I-a) | Buffer | pH | Co-solvent | PLP (mM) | Enzyme | Amine donor | PRM-102 (mg) | Time (hrs) | 2 | % Conversion |
|---|---|---|---|---|---|---|---|---|---|---|---|
| 5 | 14 mg ($R^1$ = H, citrate salt) | 20 mM (9 mL) | 7.5 | MeOH (1.0 mL) | 0.5 | Vibrio Fluvialis (310 µL) | L-alanine (10 mg) | 300 mg | 168 | (R) | 31% |
| 6 | 14 mg ($R^1$ = H, citrate salt) | 20 mM (9 mL) | 7.5 | MeOH (1.0 mL) | 0.5 | Vibrio Fluvialis (310 µL on day 1, 155 µL on day 4) | L-alanine (10 mg) | 300 mg | 168 | (R) | 41.1% |
| 7 | 14 mg ($R^1$ = H, citrate salt) | 20 mM (9 mL) | 7.5 | MeOH (1.0 mL) | 0.5 | Vibrio Fluvialis, NEW BATCH (310 µL on day 1, 155 µL on day 6) | L-alanine (10 mg) | 300 mg | 168 | (R) | 48.7% |
| 8 | 14 mg ($R^1$ = H, citrate salt) | 20 mM (9 mL) | 7.5 | MeOH (1.0 mL) | 0.5 | Vibrio Fluvialis NEW BATCH (310 µL) | L-alanine (10 mg) | 300 mg | 168 | (R) | 8.6% |
| 9 | 14 mg ($R^1$ = H, citrate salt) | 20 mM (9 mL) | 7.5 | MeOH (1.0 mL) | 0.5 | Vibrio Fluvialis, NEW BATCH (310 µL) | L-alanine (20 mg) | 300 mg | 168 | (R) | 14.5% |

TABLE 12

Method G

| | (I-a) | Buffer | Additives | Co-solvent | PLP (mM) | Enzyme | Amine donor | PRM-102 (mg) | Time (hrs) | 2 | % Conversion |
|---|---|---|---|---|---|---|---|---|---|---|---|
| 1 | 14 mg ($R^1$ = H, citrate salt) | 20 mM (9 mL) | Amberlite Resin (100 wt %) | MeOH (1.0 mL) | 0.5 | Vibrio Fluvialis (310 µL) | L-alanine (10 mg) | 300 mg | 96 | (R) | 3.7% |
| 2 | 14 mg ($R^1$ = H, citrate salt) | 20 mM (9 mL) | Dowex Resin (100 wt %) | MeOH (1.0 mL) | 0.5 | Vibrio Fluvialis (310 µL) | L-alanine (10 mg) | 300 mg | 96 | — | n/a |
| 3 | 14 mg ($R^1$ = H, citrate salt) | 20 mM (9 mL) | β-Cyclodextrin (100 wt %) | MeOH (1.0 mL) | 0.5 | Vibrio Fluvialis (310 µL) | L-alanine (10 mg) | 300 mg | 96 | (R) | 14.0 |
| 4 | 14 mg ($R^1$ = H, citrate salt) | 20 mM (9 mL) | γ-Cyclodextrin (100 wt %) | MeOH (1.0 mL) | 0.5 | Vibrio Fluvialis (310 µL) | L-alanine (10 mg) | 300 mg | 96 | (R) | 11.4 |
| 5 | 14 mg ($R^1$ = H, citrate salt) | 20 mM (9 mL) | Sodium Bisulfate (100 wt %) | MeOH (1.0 mL) | 0.5 | Vibrio Fluvialis (310 µL) | benzylamine (10 mg) | 300 mg | 96 | — | n/a |

TABLE 13

Method H

| | (I-a) | Buffer | pH | Co-solvent | PLP (mM) | Enzyme | Amine donor | PRM-102 (mg) | Time (hrs) | 2 | % Conversion |
|---|---|---|---|---|---|---|---|---|---|---|---|
| 1 | 14 mg ($R^1$ = H, citrate salt) | 20 mM (9 mL) | 7.5 | none | 0.5 | Vibrio Fluvialis (155 µL) | L-alanine (10 mg) | 300 mg | 168 | (R) | 6.4% |
| 2 | 14 mg ($R^1$ = H) | 20 mM (9 mL) | 7.5 | MeOH (1.0 mL) | 0.5 | Vibrio Fluvialis (155 µL) | L-alanine (10 mg) | 300 mg | 168 | (R) | 14.9% |
| 3 | 14 mg ($R^1$ = H) | 20 mM (9 mL) | 7.5 | DMSO (1.0 mL) | 0.5 | Vibrio Fluvialis (155 µL) | L-alanine (10 mg) | 300 mg | 168 | (R) | 8.2% |
| 4 | 14 mg ($R^1$ = H) | 100 mM (9 mL) | 7.5 | Heptane (2.0 mL) | 0.5 | Vibrio Fluvialis (155 µL) | L-alanine (10 mg) | 300 mg | 168 | — | n/a |

TABLE 13-continued

Method H

| (I-a) | Buffer | pH | Co-solvent | PLP (mM) | Enzyme | Amine donor | PRM-102 (mg) | Time (hrs) | % 2 | Conversion |
|---|---|---|---|---|---|---|---|---|---|---|
| 5 14 mg ($R^1$ = H) | 100 mM (9 mL) | 7.5 | Heptane (2.0 mL) | 0.5 | Vibrio Fluvialis (155 µL) | R-Methyl benzylamine | 300 mg | 168 | — | n/a |
| 6 14 mg ($R^1$ = H) | 100 mM (9 mL) | 7.5 | Toluene (2.0 mL) | 0.5 | Vibrio Fluvialis (155 µL) | L-alanine (10 mg) | 300 mg | 168 | — | n/a |
| 7 14 mg ($R^1$ = H) | 100 mM (9 mL) | 7.5 | Toluene (2.0 mL) | 0.5 | Vibrio Fluvialis (155 µL) | R-Methyl benzylamine | 300 mg | 168 | — | n/a |
| 8 14 mg ($R^1$ = H) | 100 mM (9 mL) | 7.5 | 2-Methyl tetrahydrofuran (2.0 mL) | 0.5 | Vibrio Fluvialis (155 µL) | L-alanine (10 mg) | 300 mg | 168 | — | n/a |
| 9 14 mg ($R^1$ = H) | 100 mM (9 mL) | 7.5 | 2-Methyl tetrahydrofuran (2.0 mL) | 0.5 | Vibrio Fluvialis (155 µL) | R-Methyl benzylamine | 300 mg | 168 | — | n/a |
| 10 14 mg ($R^1$ = H) | 100 mM (9 mL) | 7.5 | Ethylacetate (2.0 mL) | 0.5 | Vibrio Fluvialis (155 µL) | L-alanine (10 mg) | 300 mg | 168 | (R) | 12.9% (aq. layer) 1.1% (organic layer) |
| 11 14 mg ($R^1$ = H) | 100 mM (9 mL) | 7.5 | Hexanes (2.0 mL) | 0.5 | Vibrio Fluvialis (155 µL) | L-alanine (10 mg) | 300 mg | 168 | (R) | 4.2% (aq. layer) 1.6% (organic layer) |
| 12 14 mg ($R^1$ = H) | 100 mM (9 mL) | 7.5 | Perfluorohexane (2.0 mL) | 0.5 | Vibrio Fluvialis (155 µL) | L-alanine (10 mg) | 300 mg | 168 | — | n/a |

Discussion

| Table Legend | |
|---|---|
| PLP | pyridoxal phosphate |
| PRM 102 | pyruvate reductase mix available from Codexis, Inc. |
| (R) | (R) isomer preferentially generated |
| (S) | (S) isomer preferentially generated |
| % | percent conversion of the preferred isomer as determined by HPLC |
| n/a | no product detected by HPLC |
| Me | methyl, —$CH_3$ |
| Bn | benzyl, —$CH_2C_6H_5$ |
| Cbz | carbobenzyloxy, —C(=O)O$CH_2C_6H_5$ |
| DMSO | dimethylsulfoxide |
| MeOH | methanol |
| EtOAc | ethyl acetate |

Example

Evaluation of Candidate Transaminases

Candidate transaminases were evaluated using the reaction conditions described in Method A above (see Table 6). These experiments were carried out using PRM-102 (powder form) as the co-enzyme system and D-alanine or L-alanine as the amino donor molecule. In all but two of the runs, a water miscible co-solvent (methanol or trifluoroethanol ($CF_3CH_2OH$)) was employed. As shown in Table 6, % conversions of 5% and 15% were observed when the tranamination was conducted in the presence of omega amine transaminase enzyme ATA-113, and % conversions of 2% and 3% were observed when the tranamination was conducted in the presence of omega amine transaminase enzyme ATA-117. Omega amine transaminase enzymes ATA-117, known generally to be an (R)-selective transaminase, produced the compound (S)-(II-a) rather than compound (R)-(II-a). ATA-113, known generally to be an (S)-selective transaminase, produced the compound (S)-(II-a). The descriptor "n/a" indicates that the transamination product (II-a) was not detected by HPLC in the reaction mixture.

Example

Evaluation of FDH/LADH/NAD Coenzyme Mixtures

Candidate mixtures of the co-enzymes FDH, LADH and NAD were evaluated using the reaction conditions described in Method B above (see Table 7). These experiments were carried out using ATA-117 and ATA-113 as the amine transferase enzyme; D-alanine as the amino donor molecule; and DMSO, methanol or trifluoroethanol as the co-solvent. As shown in Table 7, % conversions of from 1% to 37% were observed using this co-enzyme system. Further, transamination was achieved using either ATA-117 or ATA-113 as the transaminase enzyme. The descriptor "n/a" indicates that the transamination product (II-a) was not detected by HPLC in the reaction mixture.

Example

Comparison of Omega Transaminase from *Vibrio fluvialis* with ATA-117 and ATA-113

The activity of the omega transaminase from *Vibrio fluvialis* was compared with the activities of ATA-117 and ATA-113 using the reaction conditions described in Method C above (see Table 8). These experiments were carried out using PRM-102 as the co-enzyme system and one of the following amino donor molecule: D-alanine, L-alanine, (S)-methyl benzylamine and (R)-methyl benzylamine. When ATA-117 or ATA-113 was employed as the transaminase enzyme, compound (S)-(II-a) was produced. As indicated in Table 8, this product stereochemistry (S) was obtained with amino donor molecules D-alanine, L-alanine, and (S)-methyl benzylamine. In contrast, when the omega amine transaminase from *Vibrio* fluvialis was employed as the amine transaminase enzyme, compound (R)-(II-a) was produced. As indicated in Table 8, this product stereochemistry was obtained when either (R) or (S)-methyl benzylamine was used as the amino donor molecule. The descriptor "n/a" indicates that the transamination product (II-a) was not detected by HPLC in the reaction mixture.

Example

Evaluation of Candidate Amino Donor Molecules

Candidate amino donor molecules were evaluated using the reaction conditions described in Method D above (see Table 9). These experiments were carried out using the omega transaminase from *Vibrio fluvialis*; a 20 mM phosphate buffer (pH=7.0); and methanol as the co-solvent. L-alanine, D-alanine, (R)-methylbenzylamine, (S)-methylbenzylamine, 2-aminoindane, (R)-1-aminoindane, (R)-2-amino-1-propanol, (S)-2-amino-1-propanol, (1R,2S)-cis-1-amino-2-indanol, (1R,2R)-trans-1-amino-2-indanol, 1-(R)-amino-6-hydroxyindanamine and isopropylamine were tested. As indicated in Table 9, only compound (R)-(II-a) was observed. L-alanine as amino donor molecule provided a % conversion of 16.1% over a period of 7 days. The descriptor "n/a" indicates that the transamination product (II-a) was not detected by HPLC in the reaction mixture.

Example

Evaluation of Candidate Reaction pH and Buffer Strengths

Candidate reaction pH and buffer strengths were evaluated using the reaction conditions described in Method E above (see Table 10). These experiments were carried out using buffers with different pH's and molarities. As shown in Table 10, a 20 mM phosphate buffer (maintaining a pH=8.0) was found to provide a % conversion of 14.9%. Increasing the molarity of the buffer (100 mM) was found to cause precipitation of the starting material (I-a) and reduce conversion to the product (R)-(II-a). The descriptor "n/a" indicates that the transamination product (II-a) was not detected by HPLC in the reaction mixture.

Table 11 shows the results for transamination reactions conducted at pH=7.5. These reactions were monitored for any change in the pH, and any change in the pH of the reaction mixture was adjusted using 0.1 N sodium hydroxide solution (Method F). However, it was also found that the conversion was dependent on the age of the enzyme. A fresh bottle of enzyme was found to increase % conversion up to 31% using L-alanine over a period of 7 days and 2 units/mg of the substrate compound (I-a). When the reaction mixture was charged with an additional unit of fresh enzyme at the end of day 6, the conversion improved to 48.7%. The descriptor "n/a" indicates that the transamination product (II-a) was not detected by HPLC in the reaction mixture.

Example

Evaluation of Candidate Additives

Candidate additives were evaluated using the reaction conditions described in Method G above (see Table 12). These experiments were carried out using additives, such as resins, cyclodextrins and sulfites. Resins capable of adsorbing the starting material compound (I-a) as well as the product compound (II-a) were screened. In addition, β- and γ-cyclodextrins that are known to solubilize organic compounds were also tested (% conversions of 14.0% and 11.4% were observed for β- and γ-cyclodextrin, respectively). The descriptor "n/a" indicates that the transamination product (II-a) was not detected by HPLC in the reaction mixture.

Example

Evaluation of Candidate Co-Colvents

Candidate co-colvents were evaluated using the reaction conditions described in Method H above (see Table 13). For monophasic systems, it was found that using methanol as the co-solvent provided the highest % conversion of those tested. For biphasic systems, it was found that using ethyl acetate as the co-solvent provided the highest % conversion of those tested. The descriptor "n/a" indicates that the transamination product (II-a) was not detected by HPLC in the reaction mixture.

Exemplary Sulfonylation of a Compound of Formula (II)

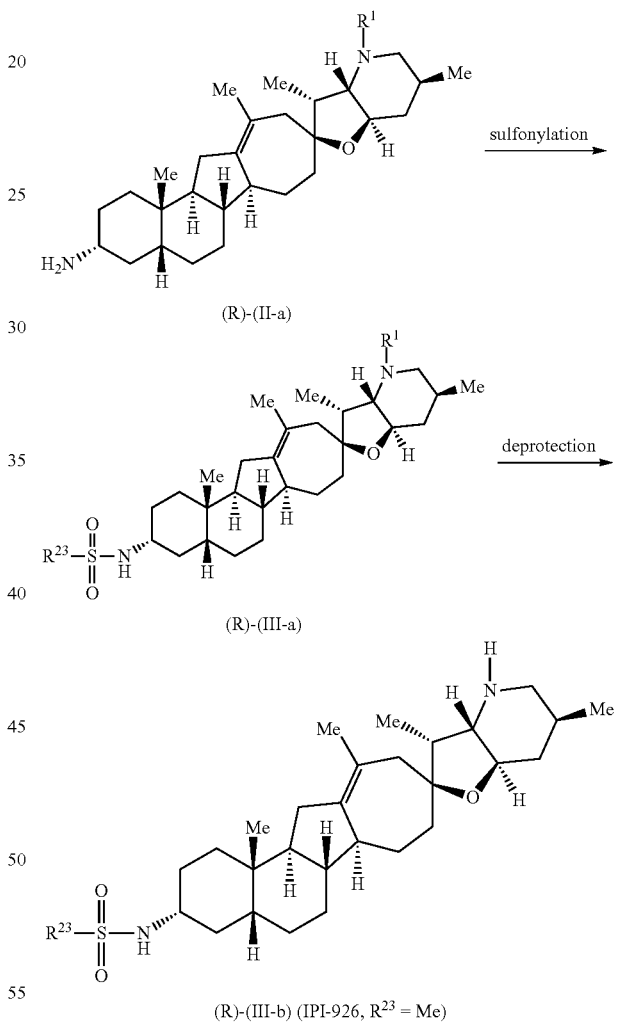

Procedure described in Tremblay et al., "Discovery of a Potent and Orally Active Hedgehog Pathway Antagonist (IPI-926)" *J. Med. Chem.* (2009) 52:4400-4418, incorporated herein by reference.

A solution of amine ($R^1$=CBz) (5.10 g, 9.09 mmol, 1 equiv) in dichloromethane (60 mL) was treated with diisopropylethylamine (5.88 g, 45.5 mmol, 5.0 equiv), cooled to 0° C., and treated with methanesulfonyl chloride (2.08 g, 18.2 mmol, 2.0 equiv). The reaction mixture was stirred for 30 min and partitioned between saturated aqueous sodium bicarbonate and ethyl acetate. The organic layer was separated, dried over sodium sulfate, and concentrated to dryness to provide a crude residue. The residue was purified using silica gel chromatography (10-30% EtOAc/hexanes) to provide the N-Cbz sulfonylated product. A suspension of the isolated product and 10% palladium on carbon (1.0 g) in 2-propanol (50 mL) was placed under hydrogen atmosphere and stirred for 4 h at room temperature. The reaction mixture was then filtered on Celite and the filtrate concentrated to dryness. The residue was then purified using silica gel chromatography (0-5% DCM/MeOH) to give IPI-926 (4.06 g, 8.05 mmol, 95% for two steps). NMR δH (400 MHz, CDCl3) 6.90 (br s, 1H), 3.31 (dt, J=10.6, 3.8 Hz, 1H), 3.20 (br s, 1H), 3.10 (dd, J=13.7, 4.5 Hz, 1H), 2.91 (s, 3H), 2.62 (dd, J=9.9, 7.6 Hz, 1H), 2.33 (br d, J=14.5 Hz, 1H), 2.27-2.15 (m, 1H), 2.10 (dd, J=14.5, 6.9 Hz, 1H), 1.99-1.17 (m, 28H), 1.05 (q, J=11.6 Hz, 1H), 0.93 (d, J=7.4 Hz, 3H), 0.88 (d, J=6.6 Hz, 3H), 0.86 (s, 3H); NMR δC (100 MHz, CDCl3) 140.47, 124.53, 82.48, 76.97, 63.73, 54.08, 53.87, 50.12, 49.98, 47.19, 44.73, 42.27, 42.10, 40.24, 37.55, 37.44, 36.04, 34.44, 31.87, 31.33, 30.46, 29.79, 28.37, 27.94, 26.26, 24.19, 22.70, 18.92, 10.19; m/z=505.29 [M+H]+; HPLC 99.1 a/a % at 215 nm.

EQUIVALENTS

Those skilled in the art will recognize, or be able to ascertain using no more than routine experimentation, many equivalents to the specific embodiments described herein. Such equivalents are intended to be encompassed by the following claims.

We claim:

1. A process for preparing a compound of formula (II):

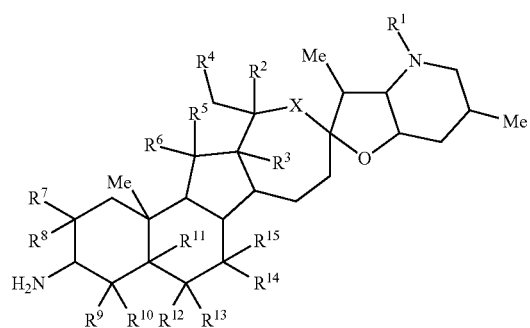

(II)

or a salt thereof;
from a compound of formula (I):

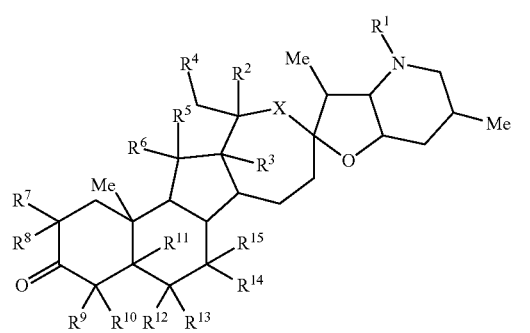

(I)

or a salt thereof;
wherein:
$R^1$ is H, alkyl, alkenyl, alkynyl, aryl, cycloalkyl, heterocycloalkyl, aralkyl, heteroaryl, heteroaralkyl, haloalkyl, —$OR^{16}$, —$C(O)R^{16}$, —$CO_2R^{16}$, —$SO_2R^{16}$, —$C(O)N(R^{17})(R^{17})$, —$[C(R^{16})_2]_q$—$R^{16}$, —$[(W)$—$N(R^{17})C(O)]_qR^{16}$, —$[(W)$—$C(O)]_qR^{16}$, —$[(W)$—$C(O)O]_qR^{16}$, —$[(W)$—$CO(O)]_qR^{16}$, —$[(W)$—$SO_2]_qR^{16}$, —$[(W)$—$N(R^{17})SO_2]_qR^{16}$, —$[(W)$—$C(O)N(R^{17})]_qR^{17}$, —$[(W)$—$O]_qR^{16}$, —$[(W)$—$N(R^{17})]_qR^{16}$, or —$[(W)$—$S]_qR^{16}$; wherein W is a diradical and q is 1, 2, 3, 4, 5, or 6;

each $R^2$ and $R^3$ is, independently, H, alkyl, alkenyl, alkynyl, aryl, cycloalkyl, heterocycloalkyl, aralkyl, heteroaryl, heteroaralkyl, haloalkyl, halo, —$OR^{16}$, —$OR^{16}$, —$N(R^{17})_2$, or —$SR^{16}$, or $R^2$ and $R^3$ taken together form a double bond or form a group

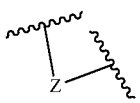

wherein Z is $NR^{17}$, O, or $C(R^{18})_2$;
$R^4$ is independently H, halo, —$OR^{16}$, —$N(R^{17})_2$, or —$SR^{16}$;
each $R^5$ and $R^6$, is, independently, H, alkyl, alkenyl, alkynyl, aryl, cycloalkyl, heterocycloalkyl, aralkyl, heteroaryl, heteroaralkyl, halo, —$OR^{16}$, —$N(R^{17})_2$, or —$SR^{16}$; or $R^5$ and $R^6$ taken together with the carbon to which they are bonded form C=O, C=S, C=N—$OR^{17}$, C=N—$R^{17}$, C=N—$N(R^{17})_2$, or form an optionally substituted 3-8 membered ring;
each $R^7$, $R^8$, $R^9$, $R^{10}$, $R^{11}$, $R^{12}$ and $R^{13}$ is, independently, H, alkyl, alkenyl, alkynyl, aryl, cycloalkyl, heterocycloalkyl, aralkyl, heteroaryl, heteroaralkyl, halo, —$OR^{16}$, —$N(R^{17})_2$, or —$SR^{16}$;
or $R^{10}$ and $R^{11}$ taken together, or $R^{11}$ and $R^{12}$ taken together, form a double bond or form a group

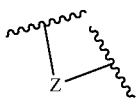

wherein Z is $NR^{17}$, O, or $C(R^{18})_2$;
each $R^{14}$ and $R^{15}$ is, independently, H, halo, —$OR^{16}$, —$N(R^{17})_2$, or —$SR^{16}$; or $R^{14}$ and $R^{15}$ taken together with the carbon to which they are bonded form C=O or C=S;
X is a bond or the group —$C(R^{19})_2$—; wherein each $R^{19}$ is, independently, H, alkyl, aralkyl, halo, —CN, —$OR^{16}$, or —$N(R^{17})_2$;
$R^{16}$ is H, alkyl, alkenyl, alkynyl, aryl, cycloalkyl, heterocycloalkyl, aralkyl, heteroaryl, heteroaralkyl or —$[C(R^{20})_2]_p$—$R^{21}$ wherein p is 0-6; or any two occurrences of $R^{16}$ on the same substituent are taken together to form a 4-8 membered optionally substituted ring;
$R^{17}$ is H, alkyl, alkenyl, alkynyl, aryl, cycloalkyl, heterocycloalkyl, aralkyl, heteroaryl, heteroaralkyl, —C(=O)$R^{20}$, —C(=O)$OR^{20}$, —$SO_2R^{20}$, —C(=O)$N(R^{20})_2$, or —$[C(R^{20})_2]_p$—$R^{21}$ wherein p is 0-6; or any two occurrences of $R^{17}$ on the same substituent are taken together to form a 4-8 membered optionally substituted ring;
$R^{18}$ is H, alkyl, alkenyl, alkynyl, aryl, cycloalkyl, heterocycloalkyl, aralkyl, heteroaryl, heteroaralkyl, halo, —CN, —$OR^{20}$, —$OSi(R^{20})_3$, —C(=O)$R^{20}$, —C(=O)$OR^{20}$, —$SO_2R^{20}$ or —C(=O)$N(R^{20})_2$;
$R^{20}$ is H, alkyl, alkenyl, alkynyl, aryl, cycloalkyl, heterocycloalkyl, aralkyl, heteroaryl, or heteroaralkyl; or any two occurrences of $R^{20}$ on the same substituent are taken together to form a 4-8 membered optionally substituted ring;

$R^{21}$ is —$OR^{22}$, —$N(R^{22})C(=O)R^{22}$, —$N(R^{22})C(=O)OR^{22}$, —$N(R^{22})SO_2(R^{22})$, —$C(=O)R^{22}N(R^{22})_2$, —$OC(=O)R^{22}N(R^{22})(R^{22})$, —$SO_2N(R^{22})(R^{22})$, —$N(R^{22})(R^{22})$, —$C(=O)OR^{22}$, —$C(=O)N(OH)(R^{22})$, —$OS(O)_2OR^{22}$, —$S(O)_2OR^{22}$, —$OP(=O)(OR^{22})(OR^{22})$, —$N(R^{22})P(O)(OR^{22})(OR^{22})$, or —$P(=O)(OR^{22})(OR^{22})$; and $R^{22}$ is H, alkyl, alkenyl, alkynyl, aryl, cycloalkyl, heterocycloalkyl, aralkyl, heteroaryl, heteroaralkyl; or any two occurrences of $R^{22}$ on the same substituent are taken together to form a 4-8 membered optionally substituted ring;

said process comprising contacting a compound of formula (I) or a salt thereof, an amino donor molecule, an amine transaminase enzyme and a cofactor in a solution to provide a compound of formula (II) or a salt thereof.

2. The process according to claim 1, wherein the co-factor is pyridoxal phosphate (PLP).

3. The process according to claim 1, wherein the co-factor is a co-enzyme.

4. The process according to claim 3, wherein the co-enzyme is selected from L-alanine dehydrogenase (LADH), lactate dehydrogenase (LDH), nicotinamide adenine dinucleotide phosphate (NADPH), nicotinamide adenine dinucleotide (NAD), formate dehydrogenase (FDH), and glucose dehydrogenase (GDH).

5. The process according to claim 1, wherein the process further comprises adding a pyruvate reductase mix to the solution.

6. The process according to claim 1, wherein the enzyme preferentially generates a compound of formula (II) or a salt thereof wherein the newly-formed amino group has (R) stereochemistry or (S) stereochemistry.

7. The process according to claim 1, wherein the enzyme preferentially generates an enantiomerically pure compound of formula (II) or salt thereof.

8. The process according to claim 1, wherein the enzyme is an omega amine transaminase, a broad-range transaminase, a glutamate-pyruvate transaminase or a glutamate-oxaloacetic transaminase.

9. The process according to claim 8, wherein the enzyme is an omega amine transaminase.

10. The process according to claim 9, wherein the omega amine transaminase is selected from the group consisting of ATA-101, ATA-102, ATA-103, ATA-104, ATA-105, ATA-106, ATA-107, ATA-108, ATA-109, ATA-110, ATA-113, ATA-114, ATA-115, ATA-116, ATA-117, ATA-124, an omega amine transaminase from *Chromobacterium violaceum*, an omega amine transaminase from *Alcaligenes denitrificans*, an omega amine transaminase from *Arthrobactercitreus*, an omega amine transaminase from *Klebsiella pneumoniae*, an omega amine transaminase from *Bacillus thuringiensis*, an omega amine transaminase from *Bacillus cereus*, and an omega amine transaminase from *Vibrio fluvialis*.

11. The process according to claim 1, wherein the amino donor molecule is an amine or salt thereof.

12. The process according to claim 1, wherein the amino donor molecule is an amino acid, a polypeptide and/or a salt thereof.

13. The process according to claim 1, wherein the amino donor molecule is selected from pyridoxamine, methylbenzylamine, 2-aminobutane, propyl amine, isopropyl amine, 1,1,1-trifluoropropan-2-amine, 1,1,1,3,3,3-hexafluoropropan-2-amine, benzyl amine, 2-amino-1-butanol, 1-amino-1-phenylethane, 1-amino-1-(2-methoxy-5-fluorophenyl)ethane, 1-amino-1-phenylpropane, 1-amino-1-(4-hydroxyphenyl)propane, 1-amino-1-(4-bromophenyl)propane, 1-amino-1-(4-nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-1-(2-naphthyl)ethane, cis-2-methylcyclopentanamine, trans-2-methylcyclopentanamine, cis-3-methylcyclopentanamine, trans-3-methylcyclopentanamine, cis-2-ethylcyclopentanamine, trans-2-ethylcyclopentanamine, cis-3-ethylcyclopentanamine, trans-3-ethylcyclopentanamine, cis-2-methylcyclohexanamine, trans-2-methylcyclohexanamine, cis-3-methylcyclohexanamine, trans-3-methylcyclohexanamine, cis-2-ethylcyclohexanamine, trans-2-ethylcyclohexanamine, cis-3-ethylcyclohexanamine, trans-3-ethylcyclohexanamine, 1-aminotetralin, 2-aminotetralin, 2-amino-5-methoxytetralin, 1-aminoindane, 2-aminoindane, 2-amino-1-propanol, cis-1-amino-2-indanol, trans-1-amino-2-indanol, 1-amino-6-hydroxyindanamine, taurine, and salts thereof.

14. The process according to claim 1, wherein the amino donor molecule is selected from glycine, alanine, aspartic acid, phenylalanine, 2-aminopentanedioic acid, 3-aminobutyrate, γ-aminobutyrate, β-alanine, asparagine, cysteine, glutamic acid, glutamine, proline, selenocysteine, serine, tyrosine, arginine, histidine, ornithine, isoleucine, leucine, lysine, methionine, threonine, tryptophan, valine, and polypeptides thereof and/or salts thereof.

15. The process according to claim 1, wherein the amino donor molecule is a chiral amino donor molecule.

16. The process according to claim 1, wherein the solution is a buffered solution.

17. The process according to claim 1, wherein the pH of the solution is between about 5 and about 9.

18. The process according to claim 1, wherein $R^1$ is H, aralkyl or —$CO_2R^{16}$.

19. The process according to claim 1, wherein $R^2$ and $R^3$ taken together form a double bond or form a group:

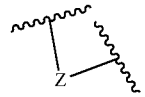

wherein Z is $NR^{17}$, O, or $C(R^{18})_2$.

20. The process according to claim 1, wherein $R^2$ and $R^3$ taken together form a double bond.

21. The process according to claim 1, wherein X is a bond.

22. The process according to claim 1, wherein X is the group —$C(R^{19})_2$—.

23. The process according to claim 1, wherein $R^4$ is H.

24. The process according to claim 1, wherein each of $R^5$ and $R^6$ is independently H, or $R^5$ and $R^6$ taken together with the carbon to which they are bonded form C=O.

25. The process according to claim 1, wherein $R^7$ and $R^8$ are each H.

26. The process according to claim 1, wherein $R^9$ and $R^{10}$ are each H.

27. The process according to claim 1, wherein $R^{11}$ is a H.

28. The process according to claim 1, wherein $R^{12}$ and $R^{13}$ are each H.

29. The process according to claim 1, wherein $R^9$ is H and $R^{10}$ and $R^{11}$ taken together form a double bond.

30. The process according to claim 1, wherein $R^{13}$ is H, and $R^{11}$ and $R^{12}$ taken together form a double bond.

31. The process according to claim 1, wherein each of $R^9$, $R^{10}$, $R^{11}$, $R^{12}$ and $R^{13}$ is H.

32. The process according to claim 1, wherein $R^{14}$ and $R^{15}$ are each H.

33. The process according to claim 1, wherein the compound of formula (I) or a salt thereof and a compound of formula (II) or a salt thereof are selected from the compounds provided in Tables 1, 2, 3, 4 or 5.

34. The process according to claim 1, wherein the compound of formula (I) is a compound of formula (I-a):

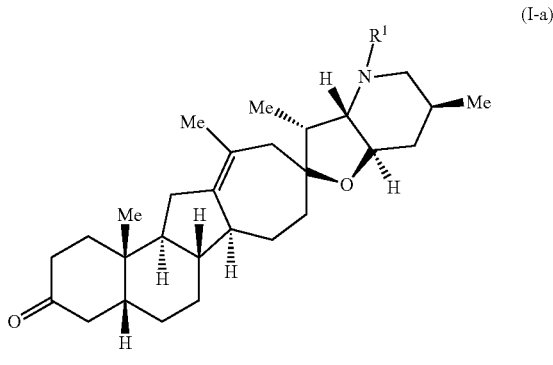

(I-a)

or salt thereof,
and the compound of formula (II) is a compound of formula (R)-(II-a):

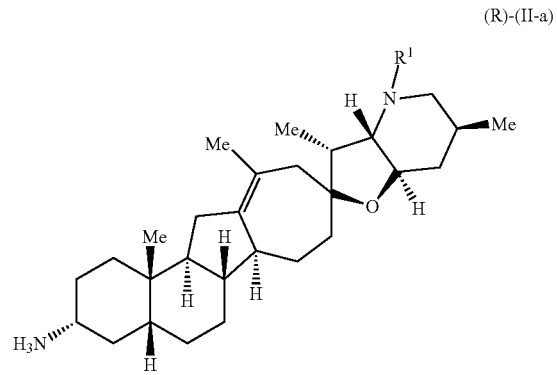

(R)-(II-a)

or a salt thereof.

35. The process according to claim 1, further comprising contacting a compound of formula (II) or a salt thereof with a sulfonylating agent to provide a compound of formula (III):

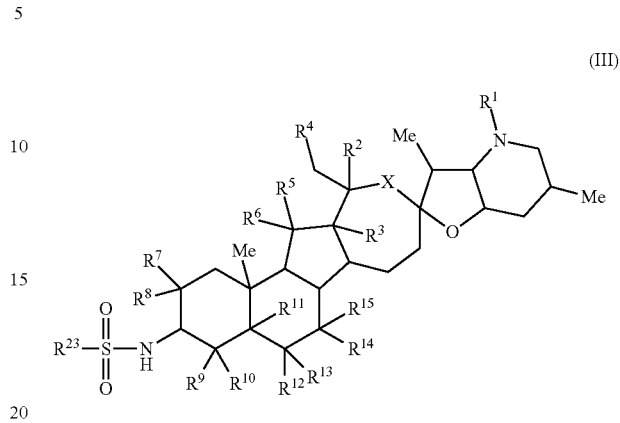

(III)

or a salt thereof, wherein $R^{23}$ is alkyl or aryl.

36. The process according to claim 35, wherein the sulfonylating agent is selected from benzenesulfonyl chloride, benzenesulfonyl anhydride, p-toluenesulfonyl chloride, p-toluenesulfonyl anhydride, methanesulfonyl chloride, and methanesulfonyl anhydride.

37. The process according to claim 36, wherein the sulfonylating agent is methanesulfonyl chloride or methanesulfonyl anhydride, and $R^{23}$ is —$CH_3$.

* * * * *